United States Patent
Shah et al.

(10) Patent No.: US 8,026,364 B2
(45) Date of Patent: Sep. 27, 2011

(54) NK₁ ANTAGONISTS

(75) Inventors: Sapna S. Shah, Jamesburg, NJ (US);
Anandan Palani, Bridgewater, NJ (US);
Xianhai Huang, Warren, NJ (US); Dong Xiao, Warren, NJ (US); Sunil Paliwal, Monroe Township, NJ (US);
Hon-Chung Tsui, East Brunswick, NJ (US); Michelle Laci Wrobleski, Whitehouse Station, NJ (US); Ashwin U. Rao, Avenel, NJ (US); Cheng Wang, King of Prussia, PA (US); Neng-Yang Shih, Warren, NJ (US)

(73) Assignee: OPKO Health, Inc., Miami, FL (US)

( * ) Notice: Subject to any disclaimer, the term of this patent is extended or adjusted under 35 U.S.C. 154(b) by 0 days.

(21) Appl. No.: 12/750,420

(22) Filed: Mar. 30, 2010

(65) Prior Publication Data
US 2010/0190759 A1  Jul. 29, 2010

Related U.S. Application Data

(62) Division of application No. 11/172,289, filed on Jun. 30, 2005, now Pat. No. 7,709,641.

(60) Provisional application No. 60/584,502, filed on Jul. 1, 2004.

(51) Int. Cl.
| C07F 7/02 | (2006.01) |
| C07D 215/12 | (2006.01) |
| C07D 215/16 | (2006.01) |
| C07D 213/02 | (2006.01) |
| C07D 211/02 | (2006.01) |
| C07D 405/00 | (2006.01) |

(52) U.S. Cl. .......... 546/14; 548/176; 548/178; 548/194; 548/199; 548/209

(58) Field of Classification Search ............ 546/14, 546/176, 178, 194, 199, 209, 210, 212, 214, 546/229, 236
See application file for complete search history.

(56) References Cited

U.S. PATENT DOCUMENTS

| 5,620,989 A | 4/1997 | Harrison et al. |
| 5,661,162 A | 8/1997 | MacLeod et al. |
| 5,760,018 A | 6/1998 | Baker et al. |
| 6,329,401 B1 | 12/2001 | Mendel et al. |
| 6,436,928 B1 | 8/2002 | Shih et al. |
| 7,049,320 B2 | 5/2006 | Paliwal et al. |
| 7,122,677 B2 | 10/2006 | Reichard et al. |
| 7,709,641 B2* | 5/2010 | Shah et al. .............. 546/14 |

FOREIGN PATENT DOCUMENTS

| WO | 03/042173 A1 | 5/2003 |
| WO | 03/051840 A1 | 6/2003 |

OTHER PUBLICATIONS

Harrison, T. et al., "Gem-Disubstituted Amino-Ether Based Substance P Antagonists", Bioorganic & Medicinal Chemistry Letters. vol. 4, No. 23; 1994; pp. 2733-2734.

International Search Report corresponding to PCT/US2005/023427 dated Jan. 26, 2006.

Rogiers, et al., "Stereoselective Conversion of 2H-1,4-Oxazin-2-ones into 2,5,5-Substituted Piperidine-2-Carboxamides and 2-Methanamines and Related Octahydro-2H-Pyrido[1,2-a]pyrazines. Potential Substance P Antagonists", Tetrahendron, vol. 57; 2001; 8971-8981.

Rombouts, et al., "Synthesis and Conformational Analysis of Substance P Antagonist Analogues Based on a 1,7-naphthyridine Scaffold", Tetrahedron, vol. 59; 2003; 4721-4731.

Wu, X., et al., "Generation of Cyclopenta[c]piperidines and Pyrrolo[3,4-c]piperidines—Potential Substance P Anatagonists—from Adducts of Cyclic Dienophiles and 5-Chloro-6-Methyl-3-Phenyl-2H-1,4-Oxazin-2-one", Tetrahendron, vol, 56; 2000; 6279-6290.

Wu, X., et al., "Stereoselective Transformation of 2H-1, 4 Oxazin-2-ones into 2, (2), 5, 5-Tri- and Tetrasubmitted Analogues of cis-5-Hydroxy-2-piperidinemethanol and cis-5-Hydroxy-6-oxo-2-piperidinecarboxylic Acid", Tetrahedron, vol. 56; 2000; pp. 3043-3051.

* cited by examiner

*Primary Examiner* — Nizal Chandrakumar
(74) *Attorney, Agent, or Firm* — Brenda Herschbach Jarrell; Kristen C. Buteau; Choate, Hall & Stewart LLP

(57) ABSTRACT

A compound having the general structure shown in Formula I:

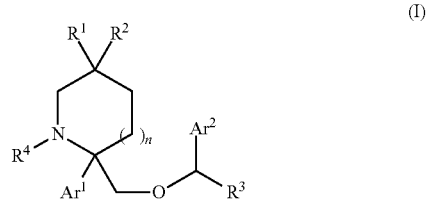

(I)

or pharmaceutically acceptable salt and/or solvates thereof are useful in treating diseases or conditions mediated by NK₁ receptors, for example various physiological disorders, symptoms or diseases, including emesis, depression, anxiety and cough.

39 Claims, No Drawings

NK₁ ANTAGONISTS

This application is a divisional of U.S. Ser. No. 11/172,289 which was filed on Jun. 30, 2005 and based upon Provisional Application No. 60/584,502 filed on Jul. 1, 2004.

FIELD OF THE INVENTION

The present invention relates to novel neurokinin-1 ($NK_1$ or NK-1) receptor antagonists, pharmaceutical compositions comprising such compounds, and methods of treatment using such compounds, to treat $NK_1$ receptor mediated diseases and conditions, including, for example, emesis, depression, anxiety and cough.

BACKGROUND OF THE INVENTION

Tachykinins are peptide ligands for neurokinin receptors. Neurokinin receptors, such as $NK_1$, $NK_2$ and $NK_3$, are involved in a variety of biological processes. They can be found in a mammal's nervous and circulatory systems, as well as in peripheral tissues. Consequently, the modulation of these types of receptors has been studied to potentially treat or prevent various mammalian disease states. For instance, $NK_1$ receptors have been reported to be involved in microvascular leakage and mucus secretion. Representative types of neurokinin receptor antagonists and the disorders that can be treated with them include, for example, sleep, pain, migraine, emesis, nociception and inflammation; see, for example, U.S. Pat. Nos. 6,329,401, 5,760,018, 5,620,989, WO 95/19344, WO 94/13639, WO 94/10165, Wu et al., *Tetrahedron*, 56, 6279-6290 (2000), Rombouts et al., *Tetrahedron*, 59, 4721-4731 (2003), and Rogiers et al., *Tetrahedron*, 57, 8971-8981 (2001).

It would be beneficial to provide a $NK_1$ antagonist that is potent, selective, and possesses beneficial therapeutic and pharmacological properties, and good metabolic stability. It would further be beneficial to provide a $NK_1$ antagonist that is effective for treating a variety of physiological disorders, symptoms and diseases, while minimizing side effects. This invention provides such $NK_1$ antagonists.

SUMMARY OF THE INVENTION

In one embodiment, the present invention is directed to a compound of Formula I:

(I)

or pharmaceutically acceptable salts and/or solvates thereof, wherein:

$R^1$ and $R^2$ are each independently selected from the group consisting of H, alkyl, haloalkyl, alkyl substituted with one or more hydroxyl groups, —CN, alkynyl, —N($R^6$)$_2$, —N($R^6$)—S($O_2$)-alkyl, —N($R^6$)—C(O)—N($R^9$)$_2$, -alkylene-CN, -cycloalkylene-CN, -alkylene-O-alkyl, —C(O)-alkyl, —C(=N—OR$^5$)-alkyl, —C(O)—N($R^9$)$_2$, —C(O)—O-alkyl, -alkylene-C(O)-alkyl, -alkylene-C(O)—O-alkyl, -alkylene-C(O)—N($R^9$)$_2$, with the proviso that at least one of $R^1$ and $R^2$ is —CN, W is =C($R^8$)— or =N—;
X is —C(O)— or —S($O_2$)—;
Y is selected from the group consisting of —$CH_2$—, —O—, and —N($R^6$)—C(O)—, with the proviso that:
(a) the nitrogen atom of —N($R^6$)—C(O)— is bonded to X, and
(b) if $R^1$ and/or $R^2$ is and Y is —O—, X is not —S($O_2$)—;
Z is —C($R^7$)$_2$—, —N($R^6$)—, or —O—;
$R^3$ is selected from the group consisting of H, —$CH_2$O$R^5$, and alkyl;
$R^4$ is selected from the group consisting of H, alkyl, cycloalkyl, heterocycloalkyl, heteroaryl, aryl, acyl, aroyl, alkylsulfonyl, and arylsulfonyl;
$R^5$ is H or alkyl;
$R^6$ is selected from the group consisting of H, alkyl, cycloalkyl, and aryl;
each $R^7$ is independently H or alkyl; or
each $R^7$, together with the ring carbon to which they are shown attached, form a cycloalkylene ring;
$R^8$ is selected from the group consisting of H, alkyl, alkyl substituted with one or more hydroxyl groups, —N($R^6$)$_2$, —N($R^6$)—S($O_2$)-alkyl, —N($R^6$)—S($O_2$)-aryl, —N($R^6$)—C(O)-alkyl, —N($R^6$)—C(O)-aryl, alkylene-O-alkyl, and —CN;

$R^9$ is selected from the group consisting of H, alkyl, and aryl, or each $R^9$, together with the nitrogen to which they are shown attached, form a heterocycloalkyl ring;

$Ar^1$ and $Ar^2$ are each independently selected from the group consisting of unsubstituted aryl and aryl substituted with 0 to 3 substituents selected from the group consisting of halogen, alkyl, alkoxy, haloalkyl, haloalkoxy, —CN, —OH, and —NO$_2$;

n is 0, 1, or 2; and m is 1, 2, or 3.

In another embodiment, the present invention is directed to a pharmaceutical composition comprising a therapeutically effective amount of at least one compound of Formula I, or a pharmaceutically acceptable salt and/or solvate thereof, and at least one pharmaceutically acceptable carrier.

In another embodiment, the present invention is directed to a kit comprising two or more containers in a single package, wherein each container in the package comprises a pharmaceutical composition. At least one container of the package comprises an effective amount of the compound of Formula I, or a pharmaceutically acceptable salt and/or solvate thereof in a pharmaceutically acceptable carrier, and at least one other container of the package comprises another therapeutic agent in a pharmaceutically acceptable carrier. The pharmaceutical compositions of the kit may be used in combination.

In another embodiment, the present invention is directed to a method for affecting an $NK_1$ receptor in a patient. The method comprises administering to the patient an effective amount of at least one compound of Formula I or a pharmaceutically acceptable salt and/or solvate thereof.

In another embodiment, the present invention is directed to a method for treating an $NK_1$ receptor mediated condition or disease (i.e., a disease associated with an $NK_1$ receptor, or a disease involving an $NK_1$ receptor in part of the disease process) in a patient in need of such treatment. The method comprises administering to the patient an effective amount of at least one compound of Formula I or a pharmaceutically acceptable salt and/or solvate thereof.

Other features and advantages of the invention will be apparent from the following detailed description, and from the claims.

DETAILED DESCRIPTION OF THE INVENTION

In a first embodiment, the present invention is directed to a compound of Formula I, or a solvate and/or salt thereof, as described herein.

In yet another embodiment, the compounds of Formula I have the following structure IA:

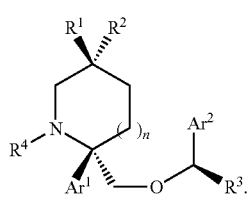

(IA)

In yet another embodiment of the compounds of Formula I, $R^3$ is $C_{1-6}$ alkyl;

$R^4$ is H;

$Ar^1$ is phenyl;

$Ar^2$ is a phenyl substituted with 1 to 3 substituents selected from the group consisting of halogen, $C_{1-6}$ alkyl, $C_{1-6}$ alkoxy, $C_{1-6}$ haloalkyl, $C_{1-6}$ haloalkoxy, —CN, and —NO$_2$; and n is 1.

In yet another embodiment of the compounds of Formula I, $R^3$ is alkyl;

$R^4$ is H;

$Ar^1$ is phenyl;

$Ar^2$ is phenyl substituted with 1 to 3 substituents selected from the group consisting of halogen, $C_{1-6}$ alkyl, $C_{1-6}$ alkoxy, $C_{1-6}$ haloalkyl, $C_{1-6}$ haloalkoxy, —CN, and —NO$_2$; and n is 1.

In yet another embodiment, the compounds of Formula I have the following structure IA:

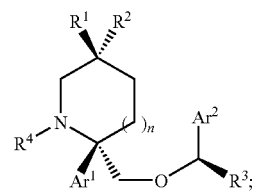

(IA)

$R^3$ is $C_{1-6}$ alkyl;

$R^4$ is H;

$Ar^1$ is phenyl;

$Ar^2$ is phenyl substituted with 1 to 3 substituents selected from the group consisting of halogen, $C_{1-6}$ alkyl, $C_{1-6}$ alkoxy, $C_{1-6}$ haloalkyl, $C_{1-6}$ haloalkoxy, —CN, and —NO$_2$; and n is 1.

In yet another embodiment, the compounds of Formula I have the following structure IA:

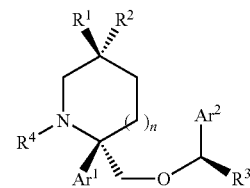

(IA)

wherein $R^1$ and $R^2$ are each independently selected from the group consisting of H, —CH$_3$, —CH$_2$CH$_2$CH$_3$, —CH$_2$Cl, —CH$_2$F, —CHCl$_2$, —CHF$_2$, —CF$_3$, —CH$_2$OH, —CH$_2$CH$_2$OH, —CH$_2$CH(OH)CH$_3$, —CH$_2$C(OH)(CH$_3$)$_2$, —CN, —CH$_2$CN, —NH$_2$, —NH—S(O$_2$)—CH$_3$, —NH—C(O)—NH$_2$, —CH$_2$OCH$_3$, —C(O)—CH$_3$, —C(O)—CH$_2$CH$_3$, —C(=N—OH)—CH$_3$, —C(=N—OH)—CH$_2$CH$_3$, —C(=N—OCH$_3$)—CH$_3$, —C(O)—NH$_2$, —C(O)—NH(CH$_3$), —C(O)—O—CH$_3$ or —C(O)—O—CH$_2$CH$_3$, —CH$_2$—C(O)—CH$_3$, —CH$_2$—C(O)O—CH$_3$, —CH$_2$—C(O)O—CH$_2$CH$_3$, —CH$_2$C(O)—NH(CH$_2$CH$_3$), —CH$_2$C(O)—NH$_2$,

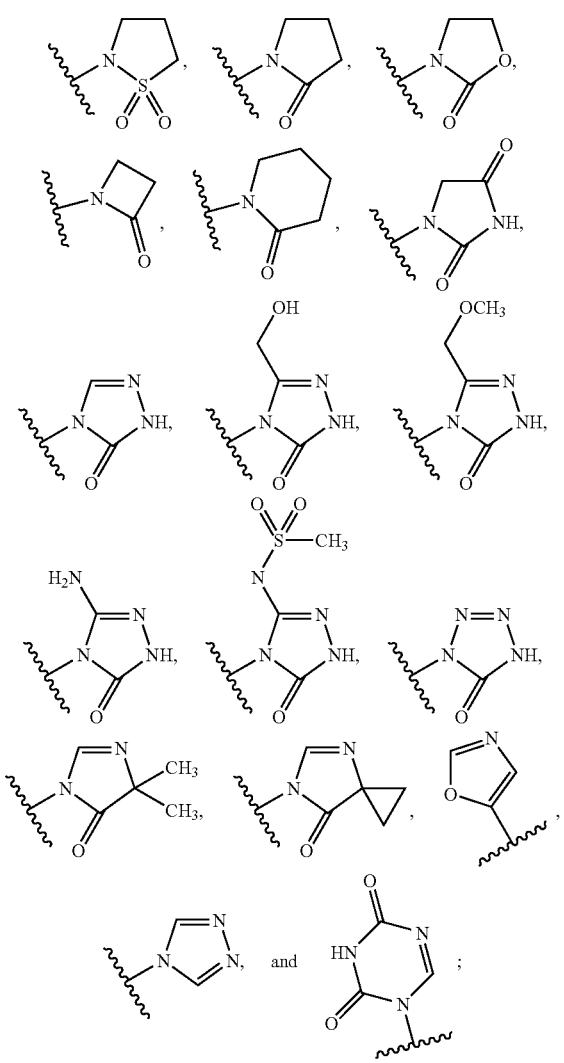

R³ is —CH₃;
R⁴ is H;
Ar¹ is phenyl;
Ar² is phenyl substituted with 1 to 3 substituents selected from the group consisting of halogen, $C_{1-6}$ alkyl, $C_{1-6}$ alkoxy, $C_{1-6}$ haloalkyl, $C_{1-6}$ haloalkoxy, —CN, and —NO₂; and
n is 1.

In yet another embodiment of the compounds of Formula I, Ar¹ is unsubstituted phenyl or phenyl substituted with 1 to 3 substituents selected from the group consisting of Cl, F, Er, —OH, $C_{1-6}$ alkyl, $C_{1-6}$ alkoxy, $C_{1-6}$ haloalkyl, $C_{1-6}$ haloalkoxy, —CN, and —NO₂.

In yet another embodiment of the compounds of Formula I, Ar¹ is unsubstituted phenyl.

In yet another embodiment of the compounds of Formula I, Ar² is unsubstituted phenyl or phenyl substituted with 1 to 3 substituents selected from the group consisting of Cl, F, Er, —OH, $C_{1-6}$ alkyl, $C_{1-6}$ alkoxy, $C_{1-6}$ haloalkyl, $C_{1-6}$ haloalkoxy, —CN, and —NO₂.

In yet another embodiment of the compounds of Formula I, Ar² is substituted phenyl.

In yet another embodiment of the compounds of Formula I, Ar² is 3,5-bis(trifluoromethyl)phenyl.

In yet another embodiment of the compounds of Formula I, R¹ is H.

In yet another embodiment of the compounds of Formula I, R¹ is a $C_{1-6}$ alkyl, for example methyl, ethyl, n-propyl, iso-propyl, n-butyl, sec-butyl, t-butyl, n-pentyl, or n-hexyl.

In yet another embodiment of the compounds of Formula I, R¹ is a $C_{1-6}$ haloalkyl, for example —CH₂Cl, —CH₂F, —CHCl₂, —CHF₂, —CF₃.

In yet another embodiment of the compounds of Formula I, R¹ is a $C_{2-6}$ alkynyl, for example —C≡C—H, —C≡C—CH₃, —C≡C—CH₂CH₃, etc.

In yet another embodiment of the compounds of Formula I, R¹ is a $C_{1-6}$ alkyl substituted with one or more hydroxy groups, for example —CH₂OH, —CH₂CH₂OH, —CH₂CH(OH)CH₃, or —CH₂C(OH)(CH₃)₂.

In yet another embodiment of the compounds of Formula I, R¹ is —CN or —$C_{1-6}$ alkylene-CN, for example —CH₂CN.

In yet another embodiment of the compounds of Formula I, R¹ is —NH₂.

In yet another embodiment of the compounds of Formula I, R¹ is —NH—S(O₂)—$C_{1-6}$ alkyl, for example —NH—S(O₂)—CH₃.

In yet another embodiment of the compounds of Formula I, R¹ is —NH—C(O)—NH₂.

In yet another embodiment of the compounds of Formula I, R¹ is —$C_{1-6}$ alkylene-O—$C_{1-6}$ alkyl, for example —CH₂OCH₃.

In yet another embodiment of the compounds of Formula I, R¹ is —C(O)—$C_{1-6}$ alkyl, for example —C(O)—CH₃ or —C(O)—CH₂CH₃.

In yet another embodiment of the compounds of Formula I, R¹ is —C(=N—OH)—$C_{1-6}$ alkyl or —C(=N—O—$C_{1-6}$ alkyl)-$C_{1-6}$ alkyl, for example —C(=N—OH)—CH₃, —C(=N—OH)—CH₂CH₃, or —C(=N—OCH₃)—CH₃.

In yet another embodiment of the compounds of Formula I, R¹ is —C(O)—NH($C_{1-6}$ alkyl), —C(O)—N($C_{1-6}$ alkyl)₂, —C(O)—NH($C_{6-10}$ aryl), —C(O)—N($C_{6-10}$ aryl)₂, —C(O)—N($C_{1-6}$ alkyl)($C_{6-10}$ aryl), or —C(O)—NH₂, for example —C(O)—NH₂ or —C(O)—NH(CH₃).

In yet another embodiment of the compounds of Formula I, R¹ is —C(O)—O—CH₃ alkyl, for example —C(O)—O—CH₃ or —C(O)—O—CH₂CH₃.

In yet another embodiment of the compounds of Formula I, R¹ is —$C_{1-6}$ alkylene-C(O)—$C_{1-6}$ alkyl, for example —CH₂—C(O)—CH₃.

In yet another embodiment of the compounds of Formula I, R¹ is —$C_{1-6}$ alkylene-C(O)—O—$C_{1-6}$ alkyl, for example —CH₂—C(O)O—CH₃ or —CH₂—C(O)O—CH₂CH₃.

In yet another embodiment of the compounds of Formula I, R¹ is —$C_{1-6}$ alkylene-C(O)—NH₂, —$C_{1-6}$ alkylene-C(O)—NH($C_{1-6}$ alkyl), —$C_{1-6}$ alkylene-C(O)—N($C_{1-6}$ alkyl)₂, —$C_{1-6}$ alkylene-C(O)—NH($C_{6-10}$ aryl), —$C_{1-6}$ alkylene-C(O)—N($C_{6-10}$ aryl)₂, or —$C_{1-6}$ alkylene-C(O)—N($C_{1-6}$ alkyl)($C_{6-10}$ aryl), for example —CH₂C(O)—NH(CH₂CH₃) or —CH₂C(O)—NH₂.

In yet another embodiment of the compounds of Formula I, R¹ is one of:

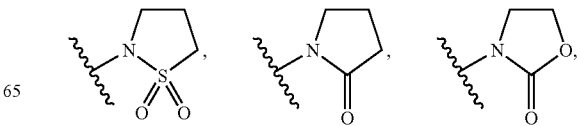

-continued

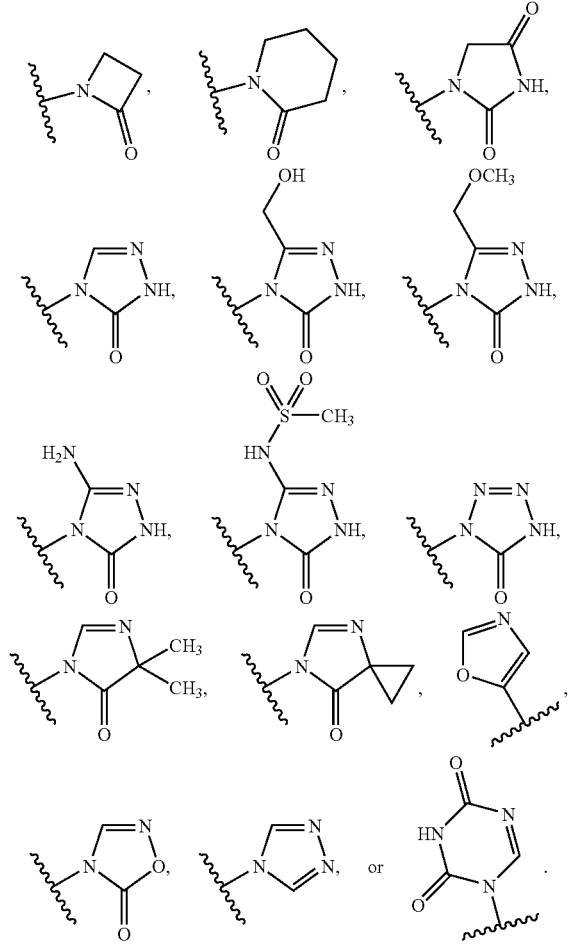

In yet another embodiment of the compounds of Formula I, $R^2$ is H.

In yet another embodiment of the compounds of Formula I, $R^2$ is a $C_{1-6}$ alkyl, for example methyl, ethyl, n-propyl, iso-propyl, n-butyl, sec-butyl, t-butyl, n-pentyl, or n-hexyl.

In yet another embodiment of the compounds of Formula I, $R^2$ is a $C_{1-6}$ haloalkyl, for example —$CH_2Cl$, —$CH_2F$, —$CHCl_2$, —$CHF_2$, —$CF_3$.

In yet another embodiment of the compounds of Formula I, $R^2$ is a $C_{2-6}$ alkynyl, for example —C≡C—H, —C≡C—$CH_3$, —C≡C—$CH_2CH_3$, etc.

In yet another embodiment of the compounds of Formula I, $R^2$ is a $C_{1-6}$ alkyl substituted with one or more hydroxy groups, for example —$CH_2OH$, —$CH_2CH_2OH$, —$CH_2CH(OH)CH_3$, or —$CH_2C(OH)(CH_3)_2$.

In yet another embodiment of the compounds of Formula I, $R^2$ is —CN or —$C_{1-6}$ alkylene-CN, for example —$CH_2CN$ or —$C(CH_3)_2CN$.

In yet another embodiment of the compounds of Formula I, $R^2$ is —$C_{3-6}$ cycloalkylene-CN, for example

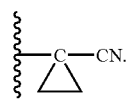

In yet another embodiment of the compounds of Formula I, $R^2$ is —$NH_2$.

In yet another embodiment of the compounds of Formula I, $R^2$ is NH—S($O_2$)—$C_{1-6}$ alkyl, —N($C_{1-6}$ alkyl)-S($O_2$)—$C_{1-6}$ alkyl or —N($C_{6-10}$ aryl)-S($O_2$)—$C_{1-6}$ alkyl for example —NH—S($O_2$)—$CH_3$.

In yet another embodiment of the compounds of Formula I, $R^2$ is —NH—C(O)—$NH_2$.

In yet another embodiment of the compounds of Formula I, $R^2$ is —$C_{1-6}$ alkylene-O—$C_{1-6}$ alkyl, for example —$CH_2OCH_3$.

In yet another embodiment of the compounds of Formula I, $R^2$ is —C(O)—$C_{1-6}$ alkyl, for example —C(O)—$CH_3$ or —C(O)—$CH_2CH_3$.

In yet another embodiment of the compounds of Formula I, $R^2$ is —C(=N—OH)—$C_{1-6}$ alkyl or —C(=N—O—$C_{is}$ alkyl)-$C_{1-6}$ alkyl, for example —C(=N—OH)—$CH_3$, —C(=N—OH)—$CH_2CH_3$, or —C(=N—$OCH_3$)—$CH_3$.

In yet another embodiment of the compounds of Formula I, $R^2$ is —C(O)—NH($C_{1-6}$ alkyl), —C(O)—N($C_{1-6}$ alkyl)$_2$, —C(O)—NH($C_{6-10}$ aryl), —C(O)—N($C_{6-10}$ aryl)$_2$, —C(O)—N($C_{1-6}$ alkyl)($C_{6-10}$ aryl), or —C(O)—$NH_2$, for example —C(O)—$NH_2$ or —C(O)—NH($CH_3$).

In yet another embodiment of the compounds of Formula I, $R^2$ is —C(O)—O—$C_{1-6}$ alkyl, for example —C(O)—O—$CH_3$ or —C(O)—O—$CH_2CH_3$.

In yet another embodiment of the compounds of Formula I, $R^2$ is —$C_{1-6}$ alkylene-C(O)—$C_{1-6}$ alkyl, for example —$CH_2$—C(O)—$CH_3$.

In yet another embodiment of the compounds of Formula I, $R^2$ is —$C_{1-6}$ alkylene-C(O)—O—$C_{1-6}$ alkyl, for example —$CH_2$—C(O)O—$CH_3$ or —$CH_2$—C(O)O—$CH_2CH_3$.

In yet another embodiment of the compounds of Formula I, $R^2$ is —$C_{1-6}$ alkylene-C(O)—$NH_2$, —$C_{1-6}$ alkylene-C(O)—NH($C_{1-6}$ alkyl), —$C_{1-6}$ alkylene-C(O)—N($C_{1-6}$ alkyl)$_2$, —$C_{1-6}$ alkylene-C(O)—NH($C_{6-10}$ aryl), —$C_{1-6}$ alkylene-C(O)—N($C_{6-10}$ aryl)$_2$, or —$C_{1-6}$ alkylene-C(O)—N($C_{1-6}$ alkyl)($C_{6-10}$ aryl), for example —$CH_2C$(O)—NH($CH_2CH_3$) or —$CH_2C$(O)—$NH_2$.

In yet another embodiment of the compounds of Formula I, $R^2$ is one of:

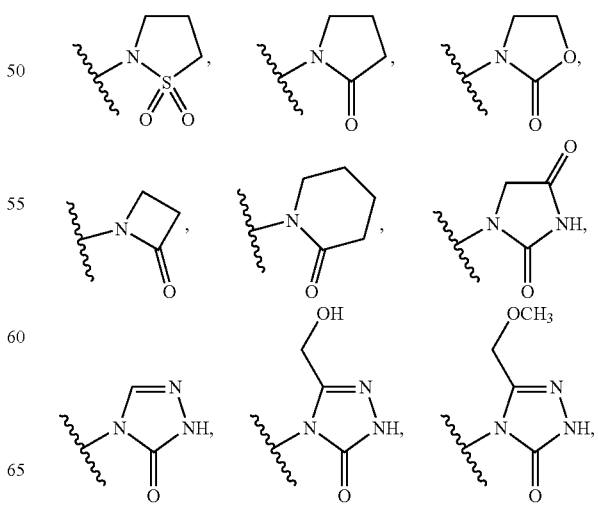

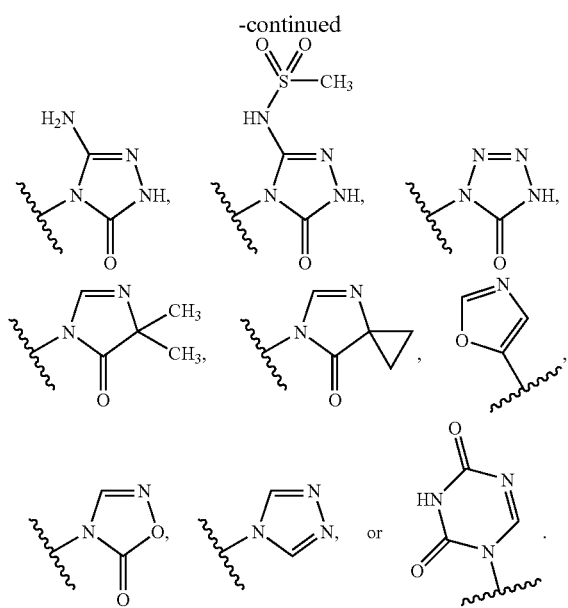

In yet another embodiment of the compounds of Formula I, $R^3$ is a $C_{1-6}$ alkyl, for example methyl, ethyl, n-propyl, isopropyl, n-butyl, sec-butyl, t-butyl, n-pentyl, or n-hexyl.

In yet another embodiment of the compounds of Formula I, $R^4$ is H.

In yet another embodiment of the compounds of Formula I, $R^4$ is $C_{1-6}$ alkyl, for example methyl, ethyl, n-propyl, isopropyl, n-butyl, sec-butyl, t-butyl, n-pentyl, or n-hexyl.

In yet another embodiment of the compounds of Formula I, $R^4$ is $C_{3-6}$ cycloalkyl, for example cyclopropyl, cyclobutyl, cyclopentyl, or cyclohexyl.

In yet another embodiment of the compounds of Formula I, $R^4$ is $C_{3-6}$ heterocycloalkyl, for example pyrrolidinyl, tetrahydrofuranyl, tetrahydrothiophenyl, tetrahydropyranyl, azetidinyl, morpholinyl, piperazinyl, or piperidinyl.

In yet another embodiment of the compounds of Formula I, $R^4$ is $C_{5-12}$ heteroaryl, for example benzimidazolyl, benzofuranyl, benzothiophenyl, furanyl, indolyl, isoquinolyl, pyrazinyl, pyridinyl, pyrimidinyl, pyrrolyl, quinolinyl, quinoxalinyl, quinazolinyl, thiophenyl, isoxazolyl, triazolyl, thiazolyl, or thiadiazolyl.

In yet another embodiment of the compounds of Formula I, $R^4$ is $C_{6-10}$ aryl, for example phenyl or naphthyl.

In yet another embodiment of the compounds of Formula I, $R^4$ is $C_{1-6}$ acyl, for example —C(O)CH$_3$, —C(O)CH$_2$CH$_3$, —C(O)CH$_2$CH$_2$CH$_3$, —C(O)CH(CH$_3$)$_2$, —C(O)C(CH$_3$)$_3$, or —C(O)CH$_2$CH(CH$_3$)$_2$.

In yet another embodiment of the compounds of Formula I, $R^4$ is $C_{6-10}$ aroyl, for example benzoyl or naphthoyl.

In yet another embodiment of the compounds of Formula I, $R^4$ is $C_{1-6}$ alkylsulfonyl, for example —S(O$_2$)CH$_3$ or —S(O$_2$)CH$_2$CH$_3$.

In yet another embodiment of the compounds of Formula I, $R^4$ is $C_{6-10}$ arylsulfonyl, for example —S(O$_2$)-phenyl or —S(O$_2$)-naphthyl.

In yet another embodiment of the compounds of Formula I, $R^5$ is H.

In yet another embodiment of the compounds of Formula I, $R^5$ is $C_{1-6}$ alkyl, for example methyl, ethyl, n-propyl, isopropyl, n-butyl, sec-butyl, t-butyl, n-pentyl, or n-hexyl.

In yet another embodiment of the compounds of Formula I, $R^6$ is H.

In yet another embodiment of the compounds of Formula I, $R^6$ is $C_{1-6}$ alkyl, for example methyl, ethyl, n-propyl, isopropyl, n-butyl, sec-butyl, t-butyl, n-pentyl, or n-hexyl.

In yet another embodiment of the compounds of Formula I, $R^6$ is $C_{3-6}$ cycloalkyl, for example cyclopropyl, cyclobutyl, cyclopentyl, or cyclohexyl.

In yet another embodiment of the compounds of Formula I, $R^6$ is $C_{6-10}$ aryl, for example phenyl or naphthyl.

In yet another embodiment of the compounds of Formula I, $R^7$ is H.

In yet another embodiment of the compounds of Formula I, $R^7$ is $C_{1-6}$ alkyl, for example methyl, ethyl, n-propyl, isopropyl, n-butyl, sec-butyl, t-butyl, n-pentyl, and n-hexyl.

In yet another embodiment of the compounds of Formula I, each $R^7$, together with the carbon atom to which they are shown attached, form a $C_{3-6}$ cycloalkyl ring, for example

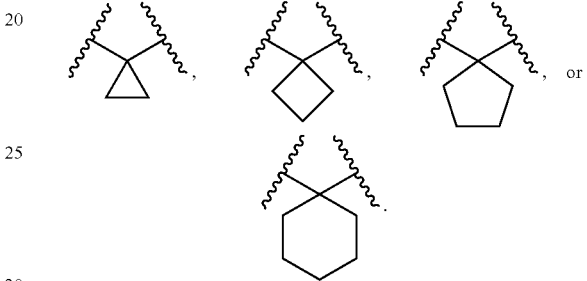

In yet another embodiment of the compounds of Formula I, $R^8$ is H.

In yet another embodiment of the compounds of Formula I, $R^8$ is $C_{1-6}$ alkyl, for example methyl, ethyl, n-propyl, isopropyl, n-butyl, sec-butyl, t-butyl, n-pentyl, and n-hexyl.

In yet another embodiment of the compounds of Formula I, $R^8$ is —NH—S(O$_2$)—C$_{1-6}$ alkyl, —N(C$_{1-6}$ alkyl)-S(O$_2$)—C$_{1-6}$ alkyl or —N(C$_{6-10}$ aryl)-S(O$_2$)—C$_{1-6}$ alkyl for example —NH—S(O$_2$)—CH$_3$.

In yet another embodiment of the compounds of Formula I, $R^8$ is —NH—S(O$_2$)—C$_{6-10}$ aryl, —N(C$_{1-6}$ alkyl)-S(O$_2$)—C$_{6-10}$ aryl or —N(C$_{6-10}$ aryl)-S(O$_2$)—C$_{6-10}$ aryl, for example —NH—S(O$_2$) -phenyl or —NH—S(O$_2$)-4-methylphenyl.

In yet another embodiment of the compounds of Formula I, $R^8$ is —NH—C(O)—C$_{1-6}$ alkyl, —N(C$_{1-6}$ alkyl)-C(O)—C$_{1-6}$ alkyl or —N(C$_{6-10}$ aryl)-C(O)—C$_{1-6}$ alkyl for example —NH—S(O$_2$)—CH$_3$.

In yet another embodiment of the compounds of Formula I, $R^8$ is —NH—C(O)—C$_{6-10}$ aryl, —N(C$_{1-6}$ alkyl)-C(O)—C$_{6-10}$ aryl or —N(C$_{6-10}$ aryl)-C(O)—C$_{6-10}$ aryl, for example —NH—C(O)-phenyl or —NH—C(±)-4-methylphenyl.

In yet another embodiment of the compounds of Formula I, $R^8$ is —C$_{1-6}$ alkylene-O—C$_{1-6}$ alkyl, for example —CH$_2$OCH$_3$.

In yet another embodiment of the compounds of Formula I, $R^8$ is a $C_{1-6}$ alkyl substituted with one or more hydroxy groups, for example —CH$_2$OH, —CH$_2$CH$_2$OH, —CH$_2$CH(OH)CH$_3$, or —CH$_2$C(OH)(CH$_3$)$_2$.

In yet another embodiment of the compounds of Formula I, $R^8$ is —CN.

In yet another embodiment of the compounds of Formula I, $R^8$ is —NH$_2$, —N(C$_{1-6}$ alkyl)$_2$, —NH(C$_{1-6}$ alkyl), —N(C$_{6-10}$ aryl)$_2$, —NH(C$_{6-10}$ aryl), —N(C$_{3-6}$ cycloalkyl)$_2$, —NH(C$_{3-6}$ cycloalkyl), —N(C$_{1-6}$ alkyl)(C$_{6-10}$ aryl), —N(C$_{1-6}$ cycloalkyl)(C$_{6-10}$ aryl), or —N(C$_{1-6}$ cycloalkyl)(C$_{1-6}$ alkyl).

In yet another embodiment of the compounds of Formula I, R⁹ is H.

In yet another embodiment of the compounds of Formula I, R⁹ is $C_{1-6}$ alkyl, for example methyl, ethyl, n-propyl, isopropyl, n-butyl, sec-butyl, t-butyl, n-pentyl, or n-hexyl.

In yet another embodiment of the compounds of Formula I, R⁹ is $C_{6-10}$ aryl, for example phenyl or naphthyl.

In yet another embodiment of the compounds of Formula I, each R⁹ together with the nitrogen atom to which they are shown attached, form a $C_{1-6}$ heterocycloalkyl ring. For example —N(R⁹)₂ forms one of

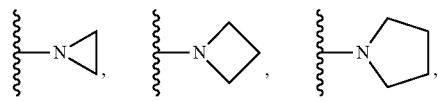

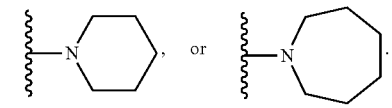

In yet another embodiment of the compounds of Formula I, X is —C(O)—.

In yet another embodiment of the compounds of Formula I, X is —S(O₂)—.

In yet another embodiment of the compounds of Formula I, Y is —CH₂—.

In yet another embodiment of the compounds of Formula I, Y is —O—.

In yet another embodiment of the compounds of Formula I, Y is —N(H)—C(O)—, —N($C_{1-6}$ alkyl)-C(O)—, or —N($C_{6-10}$ aryl)-C(O)—, for example —N(H)—C(O)—, —N(CH₃)—C(O)—, or —N(phenyl)-C(O)—.

In yet another embodiment of the compounds of Formula I, Z is —CH₂—.

In yet another embodiment of the compounds of Formula I, Z is —C($C_{1-6}$ alkyl)₂ or —CH($C_{1-6}$ alkyl), for example —C(CH₃)₂— or —CH(CH₃)—.

In yet another embodiment of the compounds of Formula I, Z is —NH—.

In yet another embodiment of the compounds of Formula I, Z is —N($C_{1-6}$ alkyl)-, for example —N(CH₃)— or —N(CH₂CH₃)—.

In yet another embodiment of the compounds of Formula I, Z is —N($C_{6-10}$ aryl)-, for example —N(phenyl)- or —N(naphthyl)-.

In yet another embodiment of the compounds of Formula I, Z is —O—.

In yet another embodiment of the compounds of Formula I, n is 0.

In yet another embodiment of the compounds of Formula I, n is 1.

In yet another embodiment of the compounds of Formula I, n is 2.

In still yet another embodiment, the compounds of Formula I have the following structure IB:

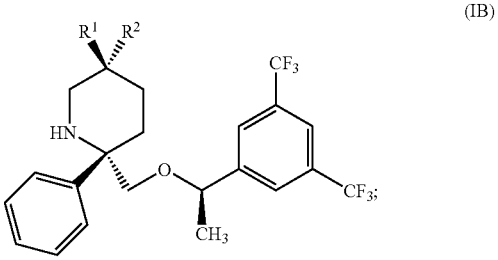

(IB)

wherein each of R¹ and R² are as shown in the following Table I:

| Compound | R¹ | R² |
|---|---|---|
| 1 | 2-oxopiperidin-1-yl | —CN |
| 2 | 2-oxooxazolidin-3-yl | —CN |
| 3 | 5-oxo-4,5-dihydro-1H-1,2,4-triazol-1-yl | —CH₂—C(OH)(H)—CH₃ |
| 4 | 5-oxo-4,5-dihydro-1H-1,2,4-triazol-1-yl | —CH₂—C(OH)(H)—CH₃ |
| 5 | 1H-1,2,4-triazol-1-yl | —CH₂CN |
| 6 | —CH₃ | 1H-1,2,4-triazol-1-yl |
| 7 | —CN | 1H-1,2,4-triazol-1-yl |
| 8 | —C(O)—O—CH₃ | 1H-1,2,4-triazol-1-yl |

-continued
| Compound | R¹ | R² |
|---|---|---|
| 9 | 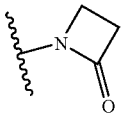 | —CN |
| 10 | —C(O)—NH₂ | 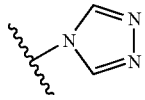 |
| 11 | 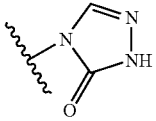 | —CH₂C(OH)(CH₃)₂ |
| 12 | —CH₂OH | 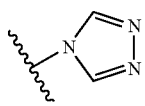 |
| 13 | 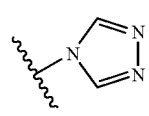 | —CH₂OCH₃ |
| 14 | —CH₂OCH₃ | 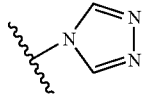 |
| 15 | 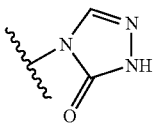 | —CH₂—NH—S(O₂)—CH₃ |
| 16 | 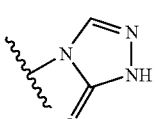 | —CH₂C(O)—NH(CH₂CH₃) |
| 17 | 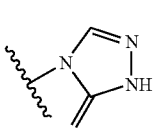 | —CH₂—C(O)O—CH₂CH₃ |
| 18 | 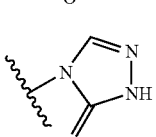 | —C(=N—OH)—CH₂CH₃ |
| 19 | 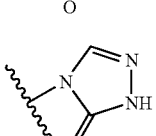 | —C(O)—CH₂CH₃ |
| 20 | 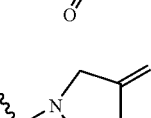 | —CH₂OCH₃ |
-continued
| Compound | R¹ | R² |
|---|---|---|
| 21 | 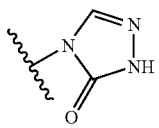 | —C(O)—NH(CH₃) |
| 22 | —C(O)—NH(CH₃) | 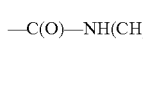 |
| 23 |  | —CH₂OH |
| 24 | 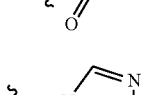 | —CH₂CH₂OH |
| 25 | 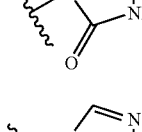 | —CH₂CH₂CH₃ |
| 26 | 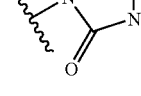 | —CH₂OCH₃ |
| 27 | —CH₂OCH₃ | 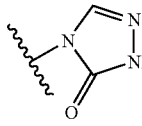 |
| 28 | 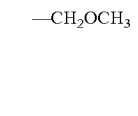 | H |
| 29 | 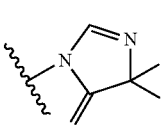 | —CH₂C(O)—NH₂ |
| 30 | 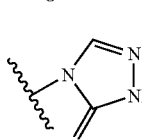 | —CH₂—C(O)—CH₃ |
| 31 | 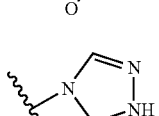 | —CH₂—C(O)O—CH₃ |

-continued
| Compound | R¹ | R² |
|---|---|---|
| 32 | 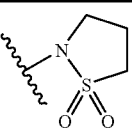 | —CN |
| 33 | 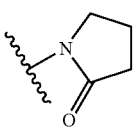 | —CN |
| 34 | —CN | 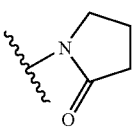 |
| 35 | —CN | 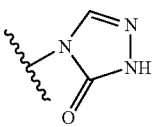 |
| 36 | —NH—S(O₂)—CH₃ | —CN |
| 37 | —CN | —NH—S(O₂)—CH₃ |
| 38 | 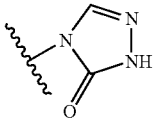 | —CH₂CN |
| 39 | —CN | —NH₂ |
| 40 | —NH₂ | —CN |
| 41 | —NH—C(O)—NH₂ | —CN |
| 42 | 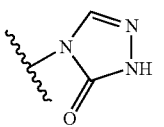 | —CN |
| 43 | 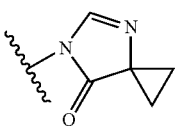 | H |
| 44 | 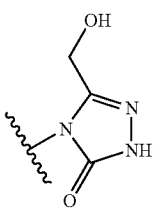 | H |
| 45 | 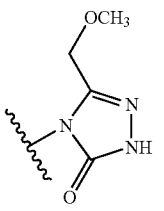 | H |
-continued
| Compound | R¹ | R² |
|---|---|---|
| 46 | H | 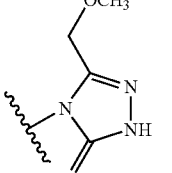 |
| 47 | 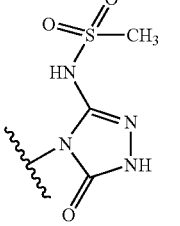 | H |
| 48 | H |  |
| 49 | 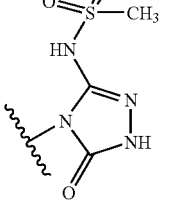 | H |
| 50 | H | 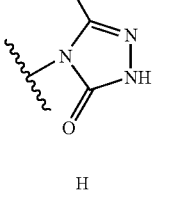 |
| 51 | 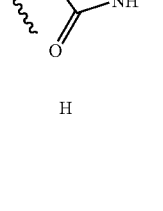 | —C(O)—NH₂ |
| 52 | 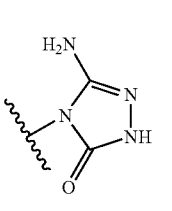 | —C(=N—OCH₃)—CH₃ |
| 53 | 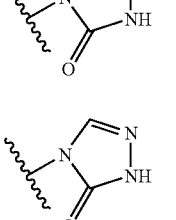 | —C(O)—CH₃ |

-continued

| Compound | R¹ | R² |
|---|---|---|
| 54 | triazolone | —C(=N—OH)—CH₃ |
| 55 | triazolone | —C(O)OCH₃ |
| 56 | triazolone | —CH₂Cl |
| 57 | triazolone | —CH₃ |
| 58 | triazolone | —C(=N—OCH₃)—CH₂CH₃ |
| 59 | —NHC(O)CH₃ | oxazole |
| 60 | H | tetrazolone |
| 61 | tetrazolone | H |

In still an additional embodiment, the present invention is directed to a method of treating a disease (or disorder or condition) in a patient in need of such treatment, wherein the disease is selected from the group consisting of: (1) respiratory diseases (e.g., chronic lung disease, bronchitis, pneumonia, asthma, allergy, cough and bronchospasm), (2) inflammatory diseases (e.g., arthritis and psoriasis), (3) skin disorders (e.g., atopic dermatitis and contact dermatitis), (4) ophthalmological disorders (e.g., retinitis, ocular hypertension and cataracts), (5) central nervous system conditions, such as depressions (e.g., neurotic depression), anxieties (e.g., general anxiety, social anxiety and panic anxiety disorders), phobias (e.g., social phobia), and bipolar disorder, (6) addictions (e.g., alcohol dependence and psychoactive substance abuse), (7) epilepsy, (8) nociception, (9) psychosis, (10) schizophrenia, (11) Alzheimer's disease, (12) AIDS related dementia, (13) Towne's disease, (14) stress related disorders (e.g., post traumatic stress disorder), (15) obsessive/compulsive disorders, (16) eating disorders (e.g., bulimia, anorexia nervosa and binge eating), (17) sleep disorders, (18) mania, (19) premenstrual syndrome, (20) gastrointestinal disorders (e.g., irritable bowel syndrome, Crohn's disease, colitis, and emesis), (21) atherosclerosis, (22) fibrosing disorders (e.g., pulmonary fibrosis), (23) obesity, (24) Type II diabetes, (25) pain related disorders (e.g., headaches, such as migraines, neuropathic pain, post-operative pain, and chronic pain syndromes), (26) bladder and genitourinary disorders (e.g., interstitial cystitis and urinary incontinence), (27) emesis (e.g., chemotherapy-induced (e.g., induced by cisplatin, doxorubicin, and taxane), radiation-induced, motion sickness, ethanol-induced, and post operative nausea and vomiting), and (28) nausea, comprising administering to the patient an effective amount of at least one (e.g., one) compound of Formula I or a pharmaceutically acceptable salt and/or solvate thereof.

In still an additional embodiment, the present invention is directed to a method of treating a disease (or disorder or condition) in a patient in need of such treatment, wherein the disease is selected from the group consisting of: respiratory diseases (e.g., cough), depression, anxiety, phobia, bipolar disorder, alcohol dependence, psychoactive substance abuse, nociception, psychosis, schizophrenia, stress related disorders, obsessive/compulsive disorder, bulimia, anorexia nervosa, binge eating, sleep disorders, mania, premenstrual syndrome, gastrointestinal disorders, obesity, pain related disorders (e.g., headaches, such as migraines, neuropathic pain, post-operative pain, and chronic pain syndromes), bladder disorders, genitourinary disorders, emesis and nausea, comprising administering to the patient an effective amount of at least one compound of Formula I or a pharmaceutically acceptable salt and/or solvate thereof.

In still an additional embodiment, the present invention also is directed to a method of treating a disease (or disorder or condition) wherein there is microvascular leakage and mucus secretion in a patient in need of such treatment, comprising administering to the patient an effective amount of at least one compound of Formula I or a pharmaceutically acceptable salt and/or solvate thereof.

In still an additional embodiment, the present invention also is directed to a method of treating asthma, emesis, nausea, depressions, anxieties, cough and pain related disorders in a patient in need of such treatment comprising administering to the patient an effective amount of at least one compound of Formula I or a pharmaceutically acceptable salt and/or solvate thereof.

In still an additional embodiment, the present invention also is directed to a method of treating emesis, depression, anxiety and cough in a patient in need of such treatment comprising administering to the patient an effective amount of at least one compound of Formula I or a pharmaceutically acceptable salt and/or solvate thereof.

In still an additional embodiment, the present invention also is directed to a method for antagonizing an effect of a Substance P at a neurokinin-1 receptor site in a patient in need of such treatment, comprising administering to the patient at least one compound of Formula I or a pharmaceutically acceptable salt and/or solvate thereof.

In still an additional embodiment, the present invention also is directed to a method for the blockade of NK₁ receptors in a patient in need of such treatment, comprising administering to the patient at least one compound of Formula I or a pharmaceutically acceptable salt and/or solvate thereof.

In still an additional embodiment, the present invention also is directed to a method for treating depression and/or anxiety in a patient in need of such treatment comprising administering to the patient an effective amount of one or more compounds of Formula I or a pharmaceutically acceptable salt and/or solvate thereof, in combination with an effective amount of one or more anti-depressant agents and/or one or more anti-anxiety agents.

In still an additional embodiment, the present invention also is directed to a method of treating an $NK_1$ receptor mediated disease (or disorder or condition) in a patient in need of such treatment comprising administering to the patient an effective amount of one or more compounds of Formula I or a pharmaceutically acceptable salt and/or solvate thereof, in combination with an effective amount of one or more selective serotonin reuptake inhibitors ("SSRIs").

In still an additional embodiment, the present invention also is directed to a method of treating depression and/or anxiety in a patient in need of such treatment comprising administering to the patient an effective amount of one or more compounds of Formula I or a pharmaceutically acceptable salt and/or solvate thereof, in combination with an effective amount of one or more selective serotonin reuptake inhibitors.

In yet an additional embodiment, the present invention also is directed to a method of treating an $NK_1$ receptor mediated disease (or disorder or condition) in a patient in need of such treatment comprising administering to the patient an effective amount of at least one compound of Formula I or a pharmaceutically acceptable salt and/or solvate thereof, in combination with at least one therapeutic agent selected from the group consisting of: other types of $NK_1$ receptor antagonists (e.g., $NK_1$ receptor antagonists other than those according to Formula I of the present invention), prostanoids, $H_1$ receptor antagonists, α-adrenergic receptor agonists, dopamine receptor agonists, melanocortin receptor agonists, endothelin receptor antagonists, endothelin converting enzyme inhibitors, angiotensin II receptor antagonists, angiotensin converting enzyme inhibitors, neutral metalloendopeptidase inhibitors, $ET_A$ antagonists, renin inhibitors, serotonin 5-$HT_3$ receptor antagonists (e.g., ondansetron), serotonin 5-$HT_{2c}$ receptor agonists, nociceptin receptor agonists, glucocorticoids (e.g., dexamethasone), rho kinase inhibitors, potassium channel modulators and inhibitors of multi-drug resistance protein 5.

In yet an additional embodiment, the invention also is directed to a method for treating an $NK_1$ mediated disease (or disorder or condition) in a patient in need of such treatment comprising administering to the patient an effective amount of a compound of Formula I or a pharmaceutically acceptable salt and/or solvate thereof, in combination with at least one therapeutic agent selected from the group consisting of: prostanoids, such as prostaglandin E1; α-adrenergic agonists, such as phentolamine mesylate; dopamine receptor agonists, such as apomorphine; angiotensin II antagonists, such as losartan, irbesartan, valsartan and candesartan; $ET_A$ antagonists, such as bosentan and ABT-627; serotonin 5-$HT_3$ receptor antagonists, such as ondansetron; and glucocorticoids, such as dexamethasone.

In yet an additional embodiment, the invention also is directed to a method for treating an $NK_1$ mediated disease (or disorder or condition) in a patient in need of such treatment comprising administering to the patient an effective amount of at least one compound of Formula I or a pharmaceutically acceptable salt and/or solvate thereof, in combination with an effective amount of at least one therapeutic agent selected from the group consisting of: other types of $NK_1$ receptor antagonists, SSRIs, dopamine receptor agonists, serotonin 5-$HT_3$ receptor antagonists, serotonin 5-$HT_{2c}$ receptor agonists, nociceptin receptor agonists, glucocorticoids and inhibitors of multi-drug resistance protein 5.

In yet an additional embodiment, the invention also is directed to a method for treating emesis, nausea and/or vomiting in a patient in need of such treatment comprising administering to the patient an effective amount of at least one compound of Formula I or a pharmaceutically acceptable salt and/or solvate thereof, in combination with an effective amount of at least one serotonin 5-$HT_3$ receptor antagonist (e.g., ondansetron) and/or at least one glucocorticoid (e.g., dexamethasone).

In still yet an additional embodiment, the present invention also is directed to a kit comprising, in separate containers in a single package, pharmaceutical compositions for use in combination to treat an $NK_1$ receptor mediated disease (or disorder or condition), wherein one container comprises a pharmaceutical composition comprising an effective amount of a compound of Formula I or a pharmaceutically acceptable salt and/or solvate thereof, in a pharmaceutically acceptable carrier, and wherein, a separate container comprises a pharmaceutical composition comprising another therapeutic agent in a pharmaceutically acceptable carrier, the therapeutic agent being selected from the group consisting of: SSRIs, other types of $NK_1$ receptor antagonists, prostanoids, $H_1$ receptor antagonists, α-adrenergic receptor agonists, dopamine receptor agonists, melanocortin receptor agonists, endothelin receptor antagonists, endothelin converting enzyme inhibitors, angiotensin II receptor antagonists, angiotensin converting enzyme inhibitors, neutral metalloendopeptidase inhibitors, $ET_A$ antagonists, renin inhibitors, serotonin 5-$HT_3$ receptor antagonists, serotonin 5-$HT_{2c}$ receptor agonists, nociceptin receptor agonists, glucocorticoids, rho kinase inhibitors, potassium channel modulators and inhibitors of multi-drug resistance protein 5.

In still yet an additional embodiment, the present invention also is directed to a kit comprising, in separate containers in a single package, pharmaceutical compositions for use in combination to treat depression and/or anxiety, wherein one container comprises a pharmaceutical composition comprising an effective amount of a compound of Formula I or a pharmaceutically acceptable salt and/or solvate thereof, in a pharmaceutically acceptable carrier, and wherein, a separate container comprises a pharmaceutical composition comprising an antidepressant agent in a pharmaceutically acceptable carrier, and/or wherein a separate container comprises a pharmaceutical composition comprising an antianxiety agent in a pharmaceutically acceptable carrier.

In still yet an additional embodiment, the present invention also is directed to a kit comprising, in separate containers in a single package, pharmaceutical compositions for use in combination to treat an $NK_1$ receptor mediated disease, wherein one container comprises a pharmaceutical composition comprising an effective amount of a compound of Formula I or a pharmaceutically acceptable salt and/or solvate thereof, in a pharmaceutically acceptable carrier, and wherein, a separate container comprises a pharmaceutical composition comprising an SSRI in a pharmaceutically acceptable carrier.

In still yet an additional embodiment, the present invention also is directed to a kit comprising, in separate containers in a single package, pharmaceutical compositions for use in combination to treat depression and/or anxiety, wherein one container comprises a pharmaceutical composition comprising an effective amount of a compound of Formula I or a pharmaceutically acceptable salt and/or solvate thereof, in a pharmaceutically acceptable carrier, and wherein, a separate container comprises a pharmaceutical composition comprising an SSRI in a pharmaceutically acceptable carrier.

In still yet an additional embodiment, the present invention also is directed to a kit comprising, in separate containers in a single package, pharmaceutical compositions for use in combination to treat emesis and/or nausea, wherein one container comprises a pharmaceutical composition comprising an effective amount of a compound of Formula I or a pharmaceutically acceptable salt and/or solvate thereof, in a pharmaceutically acceptable carrier, and wherein, a separate container comprises a pharmaceutical composition comprising a serotonin 5-HT$_3$ receptor antagonist in a pharmaceutically acceptable carrier, and/or wherein a separate container comprises a pharmaceutical composition comprising a glucocorticoid in a pharmaceutically acceptable carrier.

In still yet an additional embodiment, the present invention also is directed to a kit comprising, in separate containers in a single package, pharmaceutical compositions for use in combination to treat emesis and/or nausea, wherein one container comprises a pharmaceutical composition comprising an effective amount of a compound of Formula I or a pharmaceutically acceptable salt and/or solvate thereof, in a pharmaceutically acceptable carrier, and wherein a separate container comprises ondansetron, and/or wherein a separate container comprises dexamethasone.

Another aspect of the invention is to provide a kit comprising, in separate containers in a single package, pharmaceutical compositions for use in combination to treat an NK$_1$ receptor mediated disease, wherein one container comprises a pharmaceutical composition comprising an effective amount of a compound of Formula I in a pharmaceutically acceptable carrier, and wherein, a separate container comprises a pharmaceutical composition comprising a therapeutic agent in a pharmaceutically acceptable carrier, the therapeutic agent being selected from the group consisting of: other types of NK$_1$ receptor antagonists, SSRIs, dopamine receptor agonists, serotonin 5-HT$_3$ receptor antagonists, serotonin 5-HT$_{2c}$ receptor agonists, nociceptin receptor agonists, glucocorticoids and inhibitors of multi-drug resistance protein 5.

Except where stated otherwise, the following definitions apply throughout the specification and claims. When any variable occurs more than one time in any moiety, its definition on each occurrence is independent of its definition at every other occurrence. Chemical names, common names, and chemical structures may be used interchangeably to describe the same structure. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "alkoxy," etc.

Ac means acetyl.
AcOH (or HOAc) means acetic acid.
Boc means t-butoxycarbonyl.
Bu means butyl.
t-Bu or Bu$^t$ means tertiary-butyl.
Bn means benzyl.
Cbz means carbobenzoxy (i.e., Ph-CH$_2$—O—C(O)—).
DCM means dichloromethane.
DIEA means diisopropylethyl amine.
DMF means dimethylformamide.
DMAP means dimethylaminopyridine.
DMPU means N,NH-dimethyl propylene urea.
DMSO means dimethylsulfoxide.
DPPA means diphenylphosphorazide.
Et means ethyl.
EDC means 1-(3-dimethylaminopropyl)-3-ethylcarbodiimide hydrochloride.
FAB means fast atom bombardment.
HOTs means p-toluene sulfonic acid.
HATU means O-(7-azabenzotriazol-1-yl)-N,N,N',N'-tetramethyluroniumhexafluorophosphate.
HPLC means High Performance Liquid Chromatography.
HRMS means high resolution mass spectroscopy.
LCMS means liquid chromatography/mass spectroscopy
LiHMDS means lithium hexamethyldisilazide.
Me means methyl.
MeOH means methanol.
MS means mass spectroscopy.
Ms or mesyl means methane sulfonyl.
Ni (Ra) means Raney Ni.
OD means optical density.
Ph means phenyl
i-PA (or IPA or iPA) means iso-propyl.
PPTS means pyridinium p-toluenesulfonic acid.
PTSA means p-toluene sulfonic acid.
PYBOP means (benzotriazol-1-yloxy)tripyrrolidino phosphonium hexafluorophosphate.
RT or rt means room temperature.
TBAF means tetrabutylammonium fluoride.
TBAI means tetrabutylammonium iodide.
TFA means trifluoroacetic acid.
THF means tetrahydrofuran.
TLC means Thin Layer Chromatography.
TMS means trimethylsilyl.
TMSCl means trimethylsilyl chloride.
"Tosyl" means toluene sulfonyl.
"Patient" includes both human and animals.
"Mammal" means humans and other mammalian animals.
Portions of chemical formulae enclosed in parentheses and/or brackets denote pendant groups. For example, —C(O)— refers to a carbonyl group

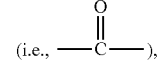

—N(alkyl)- refers to a divalent amine group with a pendant alkyl group (i.e.,

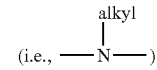

and —C(=NOCH$_3$)—CH, refers to

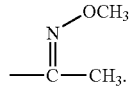

"Alkyl" means an aliphatic hydrocarbon group, which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain that may be straight or branched.

The term "substituted alkyl" means that the alkyl group may be substituted by one or more substituents which may be the same or different, each substituent being independently selected from the group consisting of halo, alkyl, aryl, cycloalkyl, cyano, hydroxy, alkoxy, alkylthio, amino, —NH (alkyl), —NH(cycloalkyl), —N(alkyl)$_2$, carboxy and —C(O)O-alkyl. Non-limiting examples of suitable alkyl groups include methyl, ethyl, n-propyl, isopropyl and t-butyl.

"Alkylene" means a divalent aliphatic hydrocarbon group, which may be straight or branched and comprising about 1 to about 20 carbon atoms in the chain. Preferred alkylene groups contain about 1 to about 12 carbon atoms in the chain. More preferred alkyl groups contain about 1 to about 6 carbon atoms in the chain. Non-limiting examples of an alkylene group include methylene (i.e., —CH$_2$—) and ethylidene (—CH$_2$CH$_2$— or —CH(CH$_3$)—).

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain, which may be straight or branched. The term "alkenyl" includes substituted alkenyl which means that the alkenyl group may be substituted by one or more substituents which may, be the same or different, each substituent being independently selected from the group consisting of halo, alkyl. aryl, cycloalkyl, cyano, alkoxy and —S(alkyl). Non-limiting examples of suitable alkenyl groups include ethenyl (i.e., vinyl), propenyl, n-butenyl, 3-methylbut-2-enyl, n-pentenyl, octenyl and decenyl.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain that may be straight or branched. Non-limiting examples of suitable alkynyl groups include ethynyl, propynyl, 2-butynyl and 3-methylbutynyl. The term "substituted alkynyl" means that the alkynyl group may be substituted by one or more substituents which may be the same or different, each substituent being independently selected from the group consisting of alkyl. aryl and cycloalkyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl, tetrazolyl and the like. The term "heteroaryl" also refers to partially saturated heteroaryl moieties such as, for example, tetrahydroisoquinolyl, tetrahydroquinolyl and the like.

"Aralkyl" or "arylalkyl" means an aryl-alkyl- group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl- group in which the alkyl and aryl are as previously described. Preferred alkylaryls comprise a lower alkyl group. A non-limiting example of a suitable alkylaryl group is tolyl. The bond to the parent moiety is through the aryl.

"Cycloalkyl" means a non-aromatic mono- or multicyclic ring system. comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like, as well as partially saturated species such as, for example, indanyl, tetrahydronaphthyl and the like.

"Cycloalkylene" means a divalent cycloalkyl ring system, comprising about 3 to about 10 carbon atoms, preferably about 5 to about 10 carbon atoms. Preferred cycloalkylene rings contain about 5 to about 7 ring atoms. The cycloalkylene can be optionally substituted with one or more "ring system substituents" which may be the same or different, and are as defined above. Non-limiting example of suitable monocyclic cycloalkylenes includes cyclopropylene (i.e.,

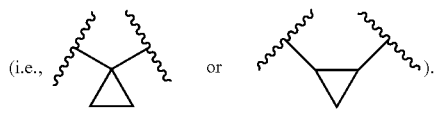

"Halogen" means fluorine, chlorine, bromine, or iodine. Preferred halogens are fluorine, chlorine and bromine. "Halogen" or "halo" substituted groups (e.g., haloalkyl groups) refers to groups substituted with one or more fluorine, chlorine, bromine, and/or iodine atoms.

"Ring system substituent" means a substituent attached to an aromatic or non-aromatic ring system, which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocycloalkyl, —C(=N—CN)—NH$_2$, —C(=NH)—NH$_2$, —C(=NH)—NH(alkyl), Y$_1$Y$_2$N—, Y$_1$Y$_2$N-alkyl-, Y$_1$Y$_2$NC(O)—, Y$_1$Y$_2$NSO$_2$— and —SO$_2$NY$_1$Y$_2$, wherein Y$_1$ and Y$_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such moiety are methylene dioxy, ethylenedioxy, —C(CH$_3$)$_2$— and the like which form moieties such as, for example:

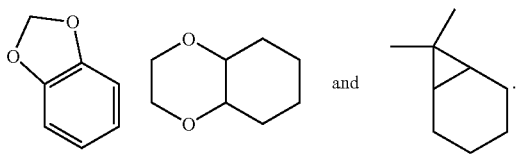

"Heterocycloalkyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocycloalkyls contain about 5 to about 6 ring atoms. The prefix aza, oxa or thia before the heterocycloalkyl root name means that at least a nitrogen, oxygen or sulfur atom respectively is present as a ring atom. Any —NH in a heterocycloalkyl ring may be present in protected form such as, for example, an —N(Boc), —N(CBz), —N(Tos) group and the like; such protected functional groups are also considered part of this invention. The heterocycloalkyl can be optionally substituted by one or more "ring system substituents" which may be the same or different, and are as defined herein. The nitrogen or sulfur atom of the heterocycloalkyl can be optionally oxidized to the corresponding N-oxide, S-oxide or S,S-dioxide. Non-limiting examples of suitable monocyclic heterocycloalkyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like.

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

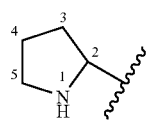

there is no —OH attached directly to carbons marked 2 and 5.

It should also be noted that tautomeric forms such as, for example, the moieties:

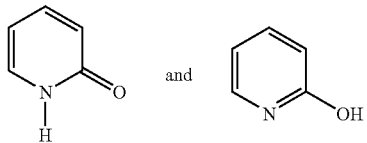

are considered equivalent in certain embodiments of this invention.

"Alkynylalkyl" means an alkynyl-alkyl- group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Heteroaralkyl" means a heteroaryl-alkyl- group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl- group in which alkyl is as previously defined. The "alkyl" portion of the hydroxyalkyl is preferably a lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-S($O_2$)— group. Preferred groups are those in which the alkyl group is lower alkyl. The bond to the parent moiety is through the sulfonyl.

"Arylsulfonyl" means an aryl-S($O_2$)— group. The bond to the parent moiety is through the sulfonyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

The term "isolated" or "in isolated form" for a compound refers to the physical state of said compound after being isolated from a synthetic process or natural source or combination thereof. The term "purified" or "in purified form" for a compound refers to the physical state of said compound after being obtained from a purification process or processes described herein or well known to the skilled artisan, in sufficient purity to be characterizable by standard analytical techniques described herein or well known to the skilled artisan.

It should also be noted that any heteroatom with unsatisfied valences in the text, schemes, examples and Tables herein is assumed to have one or more hydrogen atoms to satisfy the valences.

When a ring system (e.g., cycloalkyl, heterocycloalkyl, aryl, or heteroaryl) is substituted with a number of substituents varying within an expressly defined range, it is understood that the total number of substituents does not exceed the normal available valencies under the existing conditions. Thus, for example, a phenyl ring substituted with "n" substituents (where "n" ranges from 0 to 5) can have 0 to 5 substituents, whereas it is understood that a pyridinyl ring substituted with "n" substituents has a number of substituents ranging from 0 to 4.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in Organic Synthesis* (1991), Wiley, New York, herein incorporated by reference.

When any variable (e.g., aryl, heterocycloalkyl, $R^2$, etc.) occurs more than one time in any constituent or in Formula I, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

"Alkylheteroaryl" means an alkyl group attached to a parent moiety via a heteroaryl group.

"Alkylsulfinyl" means an alkyl-S(O)— group. Preferred groups are those in which the alkyl group is lower alkyl. The bond to the parent moiety is through the sulfinyl.

"Aralkenyl" means an aryl-alkenyl- group in which the aryl and alkenyl are as previously described. Preferred aralkenyls contain a lower alkenyl group. Non-limiting examples of suitable aralkenyl groups include 2-phenethenyl and 2-naphthylethenyl. The bond to the parent moiety is through the alkenyl.

"Aralkylthio" means an aralkyl-S— group in which the aralkyl group is as previously described. Non-limiting example of a suitable aralkylthio group is benzylthio. The bond to the parent moiety is through the sulfur.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Arylsulfinyl" means an aryl-S(O)— group. Non-limiting examples of suitable arylsulfinyl groups include phenylsulfinyl and naphthylsulfinyl. The bond to the parent moiety is through the sulfinyl.

A carbamate group means a —O—C(O)—N(alkyl or aryl)- group, and a urea group means a —N(alkyl or aryl)-C(O)—N(alkyl or aryl)- group. Representative carbamate and urea groups may include the following:

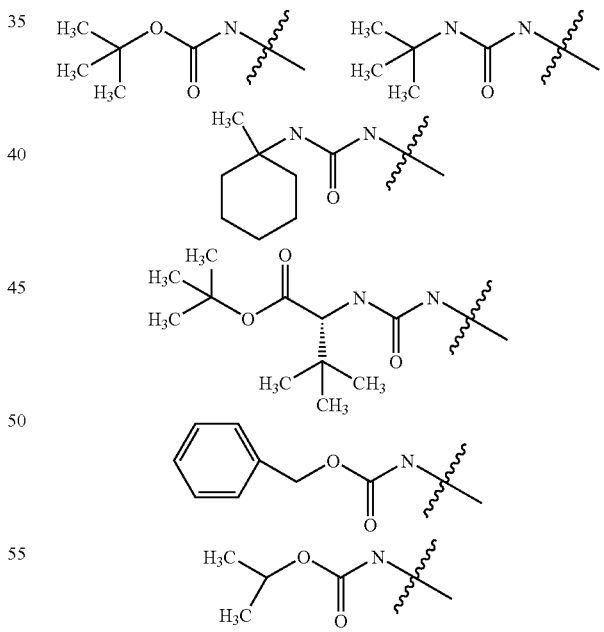

"Cycloalkenyl" means a non-aromatic mono or multicyclic ring system comprising about 3 to about 10 carbon atoms, preferably about 5 to about 10 carbon atoms, which contains at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cycloheptenyl, and the like. Non-limiting example of a suitable multicyclic cycloalkenyl is norbornylenyl.

"Cycloalkylamino" means a cycloalkyl group as defined herein attached to the parent moiety through a nitrogen atom.

"Cycloalkylaminocarbonyl" means a cyclic alkyl group attached to a nitrogen atom, which is attached to a carbonyl group; the whole may be referred to as a substituted amide.

"Heteroalkyl" means an alkyl as defined herein, in which at least one the atoms is an element other than carbon, for example nitrogen, oxygen or sulfur, alone or in combination.

"Heteroaralkenyl" means a heteroaryl-alkenyl- group in which the heteroaryl and alkenyl are as previously described. Preferred heteroaralkenyls contain a lower alkenyl group. Non-limiting examples of suitable heteroaralkenyl groups include 2-(pyrid-3-yl)ethenyl and 2-(quinolin-3-yl)ethenyl. The bond to the parent moiety is through the alkenyl.

"Heteroaralkyl" means a heteroaryl-alkyl- group in which the heteroaryl and alkyl are as previously described. Preferred heteroaralkyls contain a lower alkyl group. Non-limiting examples of suitable aralkyl groups include pyridylmethyl, 2-(furan-3-yl)ethyl and quinolin-3-ylmethyl. The bond to the parent moiety is through the alkyl.

"Heteroaralkylthio" means a heteroaryl-alkyl-S group wherein the group is attached to the parent moiety through the sulfur.

"Heteroarylsulfinyl" means a heteroaryl-S(O)— group wherein the heteroaryl is as defined herein and the heteroarylsulfinyl group is attached to the parent moiety through the sulfinyl.

"Heteroarylsulfonyl" means a heteroaryl-S(O$_2$)— group wherein the heteroaryl is as defined herein and the heteroarylsulfonyl group is attached to the parent moiety through the sulfonyl.

"Heteroarylthio" means a heteroaryl-S— group wherein the heteroaryl is as defined herein and the heteroarylsulfinyl group is attached to the parent moiety through the sulfur.

"Heterocycloalkenyl" means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocycloalkenyl rings contain about 5 to about 6 ring atoms. The prefix aza, oxa or thia before the heterocycloalkenyl root name means that at least a nitrogen, oxygen or sulfur atom respectively is present as a ring atom. The heterocycloalkenyl can be optionally substituted by one or more ring system substituents, wherein "ring system substituent" is as defined above. The nitrogen or sulfur atom of the heterocycloalkenyl can be optionally oxidized to the corresponding N-oxide, S-oxide or S,S-dioxide. Non-limiting examples of suitable monocyclic azaheterocycloalkenyl groups include 1,2,3,4-tetrahydropyridine, 1,2-dihydropyridyl, 1,4-dihydropyridyl, 1,2,3,6-tetrahydropyridine, 1,4,5,6-tetrahydropyrimidine, 2-pyrrolinyl, 3-pyrrolinyl, 2-imidazolinyl, 2-pyrazolinyl, and the like. Non-limiting examples of suitable oxaheterocycloalkenyl groups include 3,4-dihydro-2H-pyran, dihydrofuranyl, fluorodihydrofuranyl, and the like. Non-limiting example of a suitable multicyclic oxaheterocycloalkenyl group is 7-oxabicyclo[2.2.1]heptenyl. Non-limiting examples of suitable monocyclic thiaheterocycloalkenyl rings include dihydrothiophenyl, dihydrothiopyranyl, and the like.

"Heterocyclic" means, in addition to the heteroaryl groups defined below, saturated and unsaturated cyclic organic groups having at least one O, S and/or N atom interrupting a carbocyclic ring structure that consists of one ring or two fused rings, wherein each ring is 5-, 6- or 7-membered and may or may not have double bonds that lack delocalized pi electrons, which ring structure has from 2 to 8, preferably from 3 to 6 carbon atoms, e.g., 2- or 3-piperidinyl, 2- or 3-piperazinyl, 2- or 3-morpholinyl, or 2- or 3-thiomorpholinyl.

"Sulfonamide" means a sulfonyl group attached to a parent moiety through an amide.

As is well known in the art, a bond drawn from a particular atom wherein no moiety is depicted at the terminal end of the bond indicates a methyl group bound through that bond to the atom. For example:

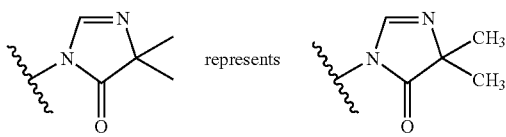

It should also be noted that throughout the specification and Claims appended hereto, that any formula, compound, moiety or chemical illustration with unsatisfied valences is assumed to have the hydrogen atom to satisfy the valences unless the context indicates a bond.

With reference to the number of moieties (e.g., substituents, groups or rings) in a compound, unless otherwise defined, the phrases "one or more" and "at least one" mean that there can be as many moieties as chemically permitted, and the determination of the maximum number of such moieties is well within the knowledge of those skilled in the art.

The wavy line ∼∼∼ as a bond generally indicates a mixture of, or either of, the possible isomers, e.g., containing (R)- and (S)-stereochemistry. For example,

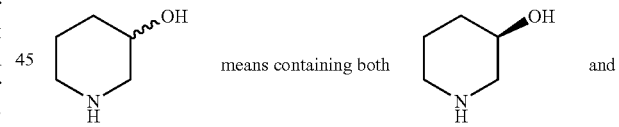

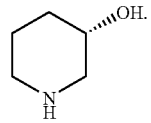

When the stereochemistry in a structure is not expressly indicated, the structure can have a mixture of, or any of the individual possible stereoisomers. Thus, when the stereochemistry is not explicitly indicated in a structure, the structure includes all stereochemical configurations having the indicated connectivity (e.g., all possible enantiomers or diastereomers), as well as mixtures of such stereoisomers (e.g., racemic mixtures). For example,

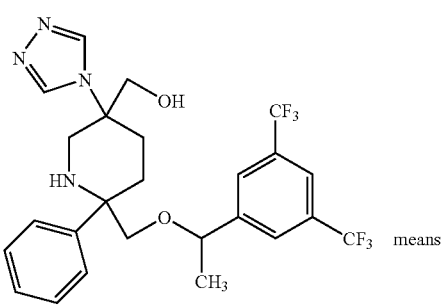 means

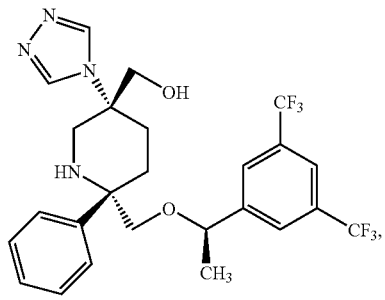

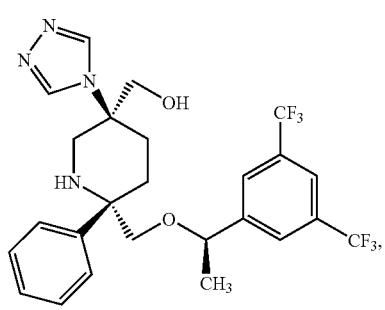

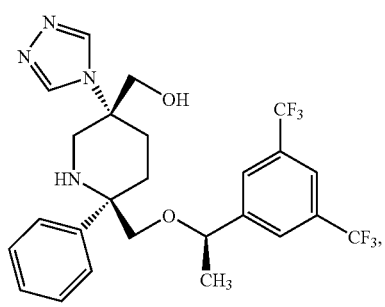

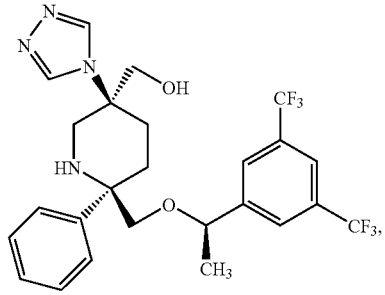

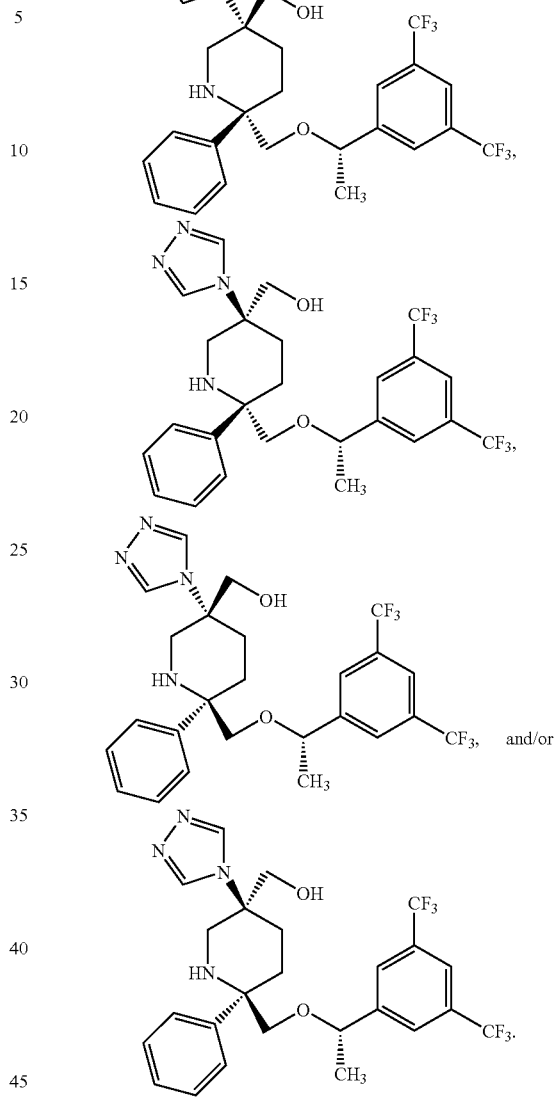

Lines drawn into the ring systems, such as, for example:

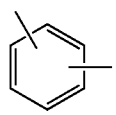

indicate that the indicated line (bond) may be attached to any of the substitutable ring carbon atoms.

Prodrugs and solvates of the compounds of the invention are also contemplated herein. The term "prodrug", as employed herein, denotes a compound that is a drug precursor which, upon administration to a subject, undergoes chemical conversion by metabolic or chemical processes to yield a compound of Formula I or a salt and/or solvate thereof. A discussion of prodrugs is provided in T. Higuchi and V. Stella, *Pro-drugs as Novel Delivery Systems* (1987) Volume 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. A "hydrate" is a solvate wherein the solvent molecule is $H_2O$.

"Effective amount" or "therapeutically effective amount" is meant to describe an amount of compound or a composition of the present invention effective in antagonizing the neurokinin-1 receptor and thus producing the desired therapeutic effect in a suitable patient.

The compounds of Formula I form salts that are also within the scope of this invention. Reference to a compound of Formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula I may be formed, for example, by reacting a compound of Formula I with an amount of acid or base, such as an equivalent amount, in a medium such as one in which the salt precipitates or in an aqueous medium followed by lyophilization.

Exemplary acid addition salts include acetates, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, methyl sulfates, 2-naphthalenesulfonates, nicotinates, nitrates, oxalates, pamoates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates,) undecanoates, and the like.

Exemplary basic salts include ammonium salts, alkali metal salts such as sodium, lithium, and potassium salts, alkaline earth metal salts such as calcium and magnesium salts, aluminum salts, zinc salts, salts with organic bases (for example, organic amines) such as benzathines, diethylamine, dicyclohexylamines, hydrabamines (formed with N,N-bis (dehydroabietyl)ethylenediamine), N-methyl-D-glucamines, N-methyl-D-glucamides, t-butyl amines, piperazine, phenylcyclohexylamine, choline, tromethamine, and salts with amino acids such as arginine, lysine and the like. Basic nitrogen-containing groups may be quarternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others. Acids (and bases) which are generally considered suitable for the formation of pharmaceutically useful salts from basic (or acidic) pharmaceutical compounds are discussed, for example, by S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; in *The Orange Book* (Food & Drug Administration, Washington, D.C. on their website); and P. Heinrich Stahl, Camille G. Wermuth (Eds.), *Handbook of Pharmaceutical Salts Properties, Selection, and Use*, (2002) Int'l. Union of Pure and Applied Chemistry, pp. 330-331, each of which is incorporated herein by reference.

All such acid salts and base salts are intended to be pharmaceutically acceptable salts within the scope of the invention and all acid and base salts are considered equivalent to the free forms of the corresponding compounds for purposes of the invention.

Compounds of Formula I and salts, solvates and prodrugs thereof, may exist in their tautomeric form (for example, as an amide or imino ether). All such tautomeric forms are contemplated herein as part of the present invention.

Polymorphic forms of the compounds of Formula I, and of the salts, solvates, and/or prodrugs thereof, are intended to be included in the present invention.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate" "prodrug" and the like, is intended to equally apply to the salt, solvate and prodrug of enantiomers, stereoisomers, rotamers, tautomers, racemates or prodrugs of the inventive compounds. "At least one", examples include 1-3, 1-2 or 1.

Compounds of Formula I are effective antagonists of the $NK_1$ receptor, and have an effect on its endogenous agonist, Substance P, at the $NK_1$ receptor site, and therefore, can be useful in treating diseases, disorders, or conditions caused or aggravated by the activity of the receptor.

The in vitro and in vivo $NK_1$, $NK_2$ and $NK_3$ activities of the compounds of Formula I can be determined by various procedures known in the art, such as a test for their ability to inhibit the activity of the $NK_1$ agonist Substance P. The percent inhibition of neurokinin agonist activity is the difference between the percent of maximum specific binding ("MSB") and 100%. The percent of MSB is defined by the following equation, wherein "dpm" represents "disintegrations per minute":

$$\% \ MSB = \frac{(dpm \ \text{of unknown}) - (dpm \ \text{of nonspecific binding})}{(dpm \ \text{of total binding}) - (cpm \ \text{of nonspecific binding})} \times 100.$$

The concentration at which the compound produces 50% inhibition of binding is then used to determine an inhibition constant ("$K_i$") using the Chang-Prusoff equation.

In vivo activity may be measured by inhibition of an agonist-induced foot tapping in a gerbil, as described in *Science*, 281, 1640-1695 (1998), which is herein incorporated by reference in its entirety. It will be recognized that compounds of Formula I can exhibit $NK_1$ antagonist activities of varying degrees. For instance, certain compounds can exhibit stronger $NK_1$ antagonist activities than others.

The compounds of the present invention exhibit potent affinities for the $NK_1$ receptor as measured by $K_i$ values (in nM). The activities (potencies) for the compounds of the invention are determined by measuring their $K_i$ values. The smaller the $K_i$ value, the more active is a compound for antagonizing the $NK_1$ receptor. Compounds of the invention exhibit a wide range of activities. The $NK_1$ average $K_i$ values for compounds of Formula I generally range from 0.01 nM to about 1000 nM, preferably, from about 0.1 nM to about 100 nM, with values of from about 0.1 nM to about 10 nM being more preferred. Even more preferred are compounds having average $K_i$ values of from 0.1 nM to about 5 nM for the $NK_1$ receptor. Especially preferred compounds have $NK_1$ average $K_i$ values of from 0.1 nM to about 1 nM. Even more especially preferred compounds have $NK_1$ average $K_i$ values of from 0.1 nM to about 0.3 nM. Compounds 2, 9, 10, 12, 14, 15, 19, 20, 23, 29, 30, 42, and 54 (see Table I above) have $K_i$ values, respectively, of 0.12, 0.18, 0.1, 0.05, 0.1, 0.13, 0.1, 0.11, 0.12 0.11, 0.54, 0.28, and 0.12 nM.

Compounds of the Formula I have a number of utilities. For instance, the inventive compounds can be useful as antagonists of neurokinin receptors, particularly, $NK_1$ receptors in a mammal, such as a human. As such, they may be useful in treating and preventing one or more of a variety of mammalian (human and animal) disease states (physiological disorders, symptoms and diseases) in a patient in need of such treatment, wherein the disease states are selected from the group consisting of: (1) respiratory diseases (e.g., chronic lung disease, bronchitis, pneumonia, asthma, allergy, cough and bronchospasm), (2) inflammatory diseases (e.g., arthritis and psoriasis), (3) skin disorders (e.g., atopic dermatitis and contact dermatitis), (4) opthalmologic disorders (e.g., retinitis, ocular hypertension and cataracts), (5) central nervous system conditions, such as depressions (e.g., neurotic depression), anxieties (e.g., general anxiety, social anxiety and panic anxiety disorders), phobias (e.g., social phobia), and bipolar disorder, (6) addictions (e.g., alcohol dependence and psychoactive substance abuse), (7) epilepsy, (8) nociception, (9) psychosis, (10) schizophrenia, (11) Alzheimer's disease, (12) AIDs related dementia, (13) Towne's disease, (14) stress related disorders (e.g., post traumatic stress disorder), (15) obsessive/compulsive disorders, (16) eating disorders (e.g., bulimia, anorexia nervosa and binge eating), (17) sleep disorders, (18) mania, (19) premenstrual syndrome, (20) gastrointestinal disorders (e.g., irritable bowel syndrome, Crohn's disease, colitis, and emesis), (21) atherosclerosis, (22) fibrosing disorders (e.g., pulmonary fibrosis), (23) obesity, (24) Type II diabetes, (25) pain related disorders (e.g., headaches, such as migraines, neuropathic pain, post-operative pain, and chronic pain syndromes), (26) bladder and genitourinary disorders (e.g., interstitial cystitis and urinary incontinence), (27) emesis (e.g., chemotherapy-induced (e.g., induced by cisplatin, doxorubicin, and taxane), radiation-induced, motion sickness, ethanol-induced, and post operative nausea and vomiting), and (28) nausea. Preferably, the inventive compounds can be useful in treating and preventing one of the following mammalian (e.g., human) disease states in a patient in need of such treatment: respiratory diseases (e.g., cough), depression, anxiety, phobia, and bipolar disorder, alcohol dependence, psychoactive substance abuse, nociception, psychosis, schizophrenia, stress related disorders, obsessive/compulsive disorder, bulimia, anorexia nervosa and binge eating, sleep disorders, mania, premenstrual syndrome, gastrointestinal disorders, obesity, pain related disorders, bladder disorders, genitourinary disorders, emesis and nausea. In particular, the compounds according to Formula I are useful for treating disease states related to microvascular leakage and mucus secretion. Consequently, the compounds of the invention are especially useful in the treatment and prevention of asthma, emesis, nausea, depressions, anxieties, cough and pain related disorders, more especially, emesis, depression, anxiety and cough.

In another aspect, the invention relates to pharmaceutical compositions comprising at least one compound (e.g., one to three compounds, preferably, one compound) represented by Formula I and at least one pharmaceutically acceptable excipient or carrier. The invention also relates to the use of such pharmaceutical compositions in the treatment of mammalian (e.g., human) disease states, such as those listed above.

In still another aspect of the invention, a method is provided for antagonizing the effects of a Substance P at a neurokinin-1 receptor site or for the blockade of one or more neurokinin-1 receptors in a mammal (i.e., a patient, e.g., a human) in need of such treatment, comprising administering to the mammal an effective amount of at least one (e.g., one) compound according to Formula I.

In another aspect of the invention, an effective amount of one or more of the inventive $NK_1$ receptor antagonists may be combined with an effective amount of one or more anti-depressant agents and/or one or more anti-anxiety agents (e.g., gepirone, gepirone hydrochloride, nefazodone, and nefazodone hydrochloride (e.g., Serzone®)) to treat depression and/or anxiety. U.S. Pat. No. 6,117,855 (2000), the disclosure of which is incorporated herein by reference, discloses a method for treating or preventing depression or anxiety with a combination therapy of a specific $NK_1$ receptor antagonist together with an anti-depressant and/or anti-anxiety agent. Thus, anti-depressant and/or anti-anxiety agents, such as those disclosed in U.S. Pat. No. 6,117,855 (2000), can be combined with one or more (e.g., one) compounds of the Formula I to treat depression and/or anxiety disease states in a mammal, preferably, a human.

In still another aspect of the invention, an effective amount of one or more (e.g., one) of the inventive $NK_1$ receptor antagonists may be combined with an effective amount of one or more (e.g., one) selective serotonin reuptake inhibitors ("SSRIs") to treat a variety of mammalian disease states, such as those described above. SSRIs alter the synaptic availability of serotonin through their inhibition of presynaptic reaccumulation of neuronally released serotonin. U.S. Pat. No. 6,162,805 (2000), the disclosure of which is incorporated herein by reference, discloses a method for treating obesity with a combination therapy of a $NK_1$ receptor antagonist and an SSRI. One or more inventive compound(s) of the Formula I can be combined together with an SSRI(s) in a single pharmaceutical composition, or it can be administered simultaneously, concurrently or sequentially with an SSRI. This combination may be useful in the treatment and prevention of obesity or another of the above-identified human and animal disease states. In particular, an effective amount of at least one (e.g., one) compound having the Formula I, alone or together with an effective amount of at least one (e.g., one) selective serotonin reuptake inhibitor, can be useful in the treatment and prevention of depression, and/or anxiety.

Numerous chemical substances are known to alter the synaptic availability of serotonin through their inhibition of presynaptic reaccumulation of neuronally released serotonin. Representative SSRIs include, without limitation, the following: fluoxetine, fluoxetine hydrochloride (e.g., Prozac®), fluvoxamine, fluvoxamine maleate (e.g. Luvox®), paroxetine, paroxetine hydrochloride (e.g., Paxil®), sertraline, sertraline hydrochloride (e.g., Zoloft®), citalopram, citalopram hydrobromide (e.g., Celexa™), duloxetine, duloxetine hydrochloride, venlafaxine, and venlafaxine hydrochloride (e.g., Effexor®). Further SSRIs include those disclosed in U.S. Pat. No. 6,162,805 (2000). Other compounds can readily be evaluated to determine their ability to selectively inhibit serotonin reuptake. Thus, one aspect of the invention relates to a pharmaceutical composition comprising at least one (e.g., one) $NK_1$ receptor antagonist having the Formula I, at least one (e.g., one) SSRI, and at least one pharmaceutically acceptable excipient or carrier. Another aspect of the invention relates to a method of treating the above identified mammalian (e.g., human) disease states, the method comprising administering to a patient in need of such treatment an effective amount of a pharmaceutical composition comprising at least one (e.g., one) $NK_1$ receptor antagonist having the Formula I in combination with at least one (e.g., one) SSRI, such as one of those recited above, and at least one pharmaceutically acceptable excipient or carrier.

In a preferred aspect, the invention relates to a method of treating depression and anxiety, the method comprising administering to a patient in need of such treatment an effective amount of at least one (e.g., one) $NK_1$ receptor antagonist having the Formula I in combination with at least one (e.g., one) SSRI, such as one of those described above. When an inventive $NK_1$ receptor antagonist is combined with an SSRI for administration to a patient in need of such treatment, the two active ingredients can be administered simultaneously, consecutively (one after the other within a relatively short period of time), or sequentially (first one and then the other over a period of time). In general, when the two active ingredients are administered consecutively or sequentially, the inventive $NK_1$ receptor antagonist is, preferably, administered before the administration of the SSRI.

It is another embodiment of the invention to treat a patient suffering from multiple ailments with a combination therapy, the therapy comprising administering to a patient (e.g., a mammal, preferably a human) in need of such treatment at least one compound of Formula I, and at least one other active ingredient (i.e., drug) used for treating one or more of the ailments being suffered by the patient. The compounds of Formula I and the other active ingredients can be administered sequentially, concurrently and/or simultaneously. The compounds of Formula I and the other active ingredients can be administered separately in any suitable dosage form. Preferably, administration is accomplished using an oral dosage forms or using a transdermal patches. The compounds of Formula I and the other active ingredients can be formulated together and administered in one combined dosage form.

Thus, the compounds of the invention may be employed alone or in combination with other active agents. Combination therapy includes the administration of two or more active ingredients to a patient in need of treatment. In addition to the above described $NK_1$ receptor antagonist/SSRI combination therapy, the compounds having the Formula I may be combined with one or more other active agents, such as the following: other types of $NK_1$ receptor antagonists (e.g., those that are disclosed in neurokinin receptor antagonist patents cited above), prostanoids, $H_1$ receptor antagonists, α-adrenergic receptor agonists, dopamine receptor agonists, melanocortin receptor agonists, endothelin receptor antagonists, endothelin converting enzyme inhibitors, angiotensin II receptor antagonists, angiotensin converting enzyme inhibitors, neutral metalloendopeptidase inhibitors, $ET_A$ antagonists, renin inhibitors, serotonin 5-$HT_3$ receptor antagonists (e.g., ondansetron, ondansetron hydrochloride (e.g., Zolfran®), palonosetron, granisetron, and granisetron hydrochloride (e.g., Kytril®), serotonin 5-$HT_{2C}$ receptor agonists, nociceptin receptor agonists, glucocorticoids (e.g., dexamethasone), rho kinase inhibitors, potassium channel modulators and/or inhibitors of multi-drug resistance protein 5.

Particularly useful therapeutic agents for combination therapy with compounds of the invention are the following: prostanoids, such as prostaglandin $E_1$; α-adrenergic agonists, such as phentolamine mesylate; dopamine receptor agonists, such as apomorphine; angiotensin II antagonists, such as losartan, irbesartan, valsartan and candesartan; $ET_A$ antagonists, such as bosentan and ABT-627; serotonin 5-$HT_3$ receptor antagonists, such as ondansetron; and glucocorticoids, such as dexamethasone. In preferred embodiments of the invention, the inventive compounds can be combined with: other types of $NK_1$ receptor antagonists, SSRIs, dopamine receptor agonists, serotonin 5-$HT_3$ receptor antagonists, serotonin 5-$HT_{2C}$ receptor agonists, nociceptin receptor agonists, glucocorticoids and/or inhibitors of multi-drug resistance protein 5.

Another embodiment of this invention is directed to a method for treating a physiological disorder, symptom or disease in a patient in need of such treatment, comprising administering to the patient an effective amount of at least one compound of Formula I, and an effective amount of at least one active ingredient selected from the group consisting of: other $NK_1$ receptor antagonists, selective serotonin reuptake inhibitors, dopamine receptor agonists, serotonin 5-$HT_3$ receptor antagonists, serotonin 5-$HT_{2C}$ receptor agonists, nociceptin receptor agonists, glucocorticoids and inhibitors of multidrug resistance protein 5, wherein the physiological disorder, symptom or disease is selected from the group consisting of: a respiratory disease, depression, anxiety, phobia, bipolar disorder, alcohol dependence, psychoactive substance abuse, nociception, psychosis, schizophrenia, stress related disorder, obsessive/compulsive disorder, bulimia, anorexia nervosa, binge eating, sleep disorder, mania, premenstrual syndrome, gastrointestinal disorder, obesity, headache, neuropathic pain, post-operative pain, chronic pain syndrome, bladder disorder, genitourinary disorder, cough, emesis and nausea.

Pharmaceutical compositions may contain from about 0.1 to about 99.9 weight percent, or from about 5 to about 95 weight percent, or from about 20 to about 80 weight percent of active ingredient (compound of the Formula I). For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g. magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington: *The Science and Practice of Phar-* macy, 20$^{th}$ Edition, (2000), Lippincott Williams & Wilkins, Baltimore, Md., herein incorporated by reference.

Liquid form preparations include solutions, suspensions and emulsions, for example, water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations, which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in a unit dosage form. In such form, the preparations subdivided into suitably sized unit doses containing appropriate quantities of the active component, e.g., an effective amount to achieve the desired purpose.

The term "pharmaceutical composition" is also intended to encompass both the bulk composition and individual dosage units, in any of the forms described herein, comprised of more than one (e.g., two) pharmaceutically active agents such as, for example, a compound of the present invention and an additional agent selected from the lists of the additional agents described herein, along with any pharmaceutically inactive excipients. The bulk composition and each individual dosage unit can contain fixed amounts of the aforesaid "more than one pharmaceutically active agents". The term "bulk composition" means material that has not yet been formed into individual dosage units. An illustrative dosage unit is an oral dosage unit such as tablets, pills and the like. Similarly, the herein-described method of treating a patient by administering a pharmaceutical composition of the present invention is also intended to encompass the administration of the aforesaid bulk composition and individual dosage units.

The quantity of active compound in a unit dose of preparation may be varied or adjusted from about 0.01 mg to about 4000 mg, preferably from about 0.02 mg to about 1000 mg, more preferably from about 0.3 mg to about 500 mg, and most preferably from about 0.04 mg to about 250 mg according to the particular application.

The actual dosage employed may be varied depending upon the requirements of the patient and the severity of the condition being treated. Determination of the proper dosage regimen for a particular situation is within the skill in the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 0.02 mg/day to about 2000 mg/day, in two to four divided doses.

The pharmaceutical compositions of the invention may be administered from about 1 to about 5 times per day, or alternatively, as a continuous infusion. Such administration can be used as a chronic or acute therapy.

The quantity of NK$_1$ receptor antagonist in combination with a selective serotonin reuptake inhibitor ("SSRI") in a unit dose of preparation may be from about 10 to about 300 mg of NK$_1$ receptor antagonist combined with from about 10 to about 100 mg of SSRI. In another combination the quantity of NK$_1$ receptor antagonist in combination with a SSRI in a unit dose of preparation may be from about 50 to about 300 mg of NK$_1$ receptor antagonist combined with from about 10 to about 100 mg of SSRI. In another combination the quantity of NK$_1$ receptor antagonist in combination with SSRI in a unit dose of preparation may be from about 50 to about 300 mg of NK$_1$ receptor antagonist combined with from about 20 to about 50 mg of SSRI.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required. Upon improvement of a patient's condition, a maintenance dose of a compound, composition or combination of the invention may be administered, if necessary. Subsequently, the dosage or frequency of administration, or both, may be reduced, as a function of the symptoms, to a level at which the improved condition is retained. When the symptoms have been alleviated to the desired level, treatment should cease. Patients may, however, require intermittent treatment on a long-term basis upon any recurrence of disease symptoms.

Specific dosage and treatment regimens for any particular patient may be varied and will depend upon a variety of factors, including the activity of the specific compound employed, the age, body weight, general health status, sex and diet of the patient, the time of administration, the rate of excretion, the specific drug combination, the severity and course of the symptoms being treated, the patient's disposition to the condition being treated and the judgment of the treating physician. Determination of the proper dosage regimen for a particular situation is within the skill of the art.

EXAMPLES

The invention disclosed herein is exemplified by the following preparations and examples, which should not be construed to limit the scope of the disclosure. Alternative mechanistic pathways and analogous structures may be apparent to those skilled in the art.

Preparative Example 1

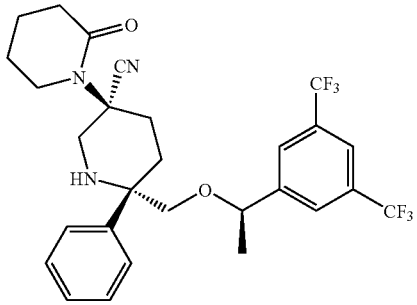

Step 1:

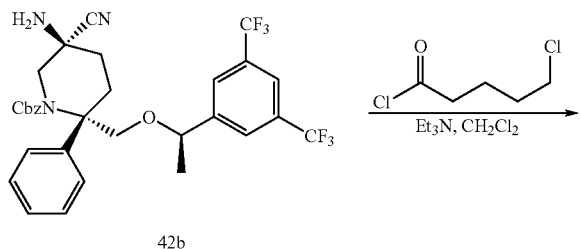

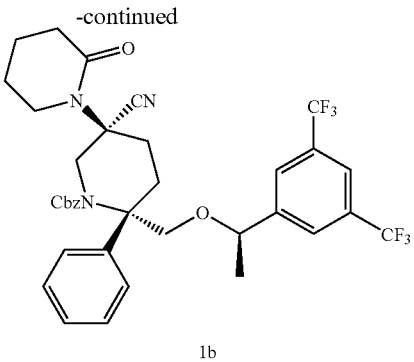

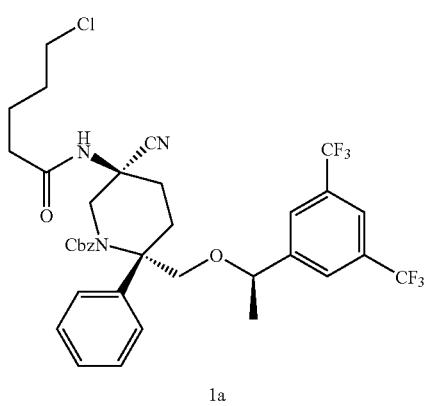

1a

In a 25 mL round-bottomed flask, Compound 42b (0.253 g, 0.42 mmol, 1.0 equiv) was taken up in 5 mL of CH$_2$Cl$_2$, and the resulting reaction mixture was cooled to 0° C. in an ice bath. Et$_3$N (0.088 mL, 0.63 mmol, 1.5 equiv) followed by 4-chlorobutyryl chloride (0.065 mL, 0.5 mmol, 1.2 equiv) was then added to the reaction mixture, which was subsequently slowly warmed to room temperature and was stirred for 14 hrs. The progress of the reaction was monitored by TLC (60:40 EtOAc/hexane) and MS. Upon completion, the reaction mixture was diluted with CH$_2$Cl$_2$, quenched with saturated aqueous NaHCO$_3$, followed by brine. The organic layer was dried over Na$_2$SO$_4$ and concentrated to give crude Compound 1a (0.3 g), which was used in the next step without further purification.

Electrospray MS [M+1] 724.4.

Step 2:

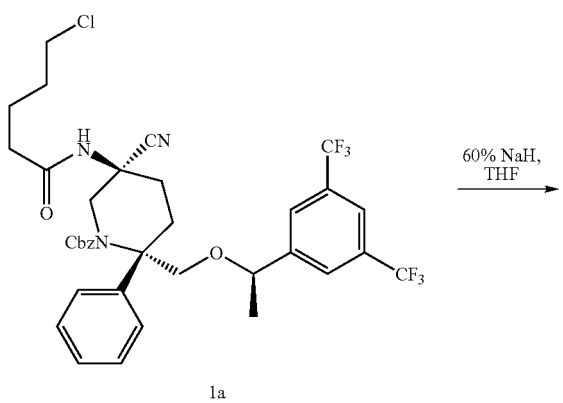

1a

In a flame-dried 25 mL round-bottomed flask, Compound 1a (0.3 g, 0.4 mmol, 1.0 equiv) was taken up in dry THF. To this reaction mixture, 60% NaH (0.025 g, 0.62 mmol, 1.5 equiv) was added, and reaction mixture was stirred at room temperature for 2 hrs. The progress of the reaction was monitored by TLC (60:40 EtOAc/hexane) and MS. Upon completion, the reaction mixture was diluted with EtOAc and quenched with saturated aqueous NaHCO$_3$. The organic layer was dried over Na$_2$SO$_4$ and concentrated to give Compound 1b (0.25 g), which was used in the next step without further purification.

Step 3:

Compound 1b (0.25 g, 0.37 mmol, 1.0 equiv) was dissolved in dry MeOH (2.0 mL) and was treated with 20% Pd(OH)$_2$ (60% wt.) under an inert atmosphere. The reaction mixture was hydrogenated at atmospheric pressure and was monitored by TLC (60:40 EtOAc/hexane). The reaction was completed in 45 min, and the reaction mixture was then filtered through CELITE (diatomaceous earth), washed with EtOAc, and concentrated to give a crude product. Purification was carried out using preparative plate chromatography (60/40 EtOAc/hexane) to give Compound 1 (0.10 g, 49%)

Electrospray MS [M+1] 554.3.

HRMS (FAB) calculated for C$_{28}$H$_{29}$F$_6$N$_3$O$_2$(M+1) 554.2242. found 554.2249.

Preparative Example 2

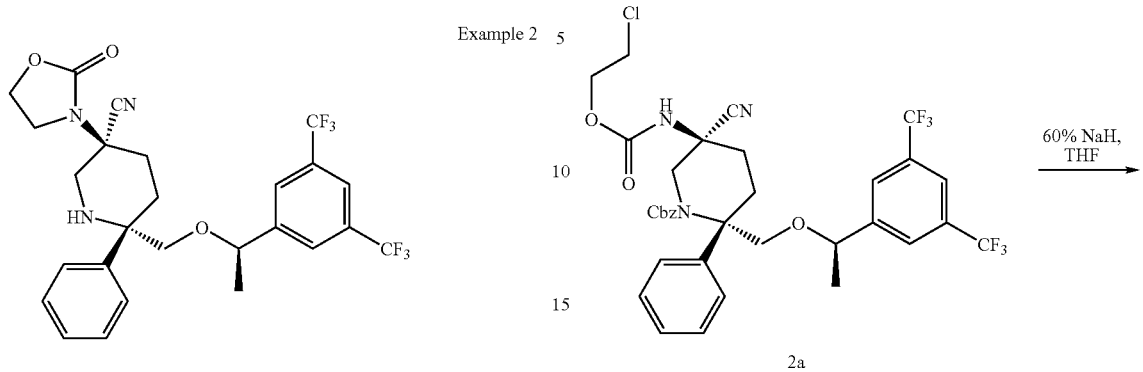

Example 2

Step 1:

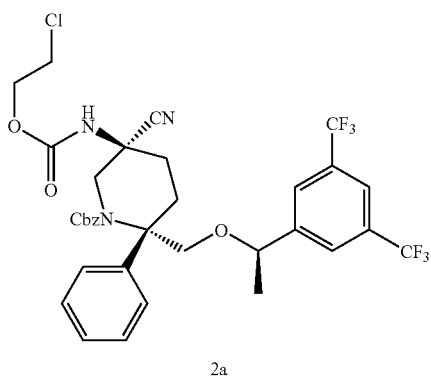

42b

In a 25 ml round-bottomed flask, Compound 42b (0.3264 g, 0.44 mmol, 1.0 equiv) was taken up in 5 mL of THF, and the reaction mixture was cooled to 0° C. in an ice bath. Et₃N (3.073 mL, 0.44 mmol, 1.2 equiv) followed by 2-chloroethyl chloroformate (0.054 mL, 0.44 mmol, 1.2 equiv) was then added to the reaction mixture, which was slowly warmed to room temperature and stirred for 14 hrs. The progress of the reaction was monitored by TLC (40:60 EtOAc/hexane) and MS. The reaction did not go to completion, and hence was diluted with EtOAc and quenched with saturated NaHCO₃ followed by brine. The organic layer was dried over Na₂SO₄ and concentrated to give (0.3 g) crude product, which was subjected to BIOTAGE chromatography (40:60 EtOAc/hexane) to give Compound 2a (0.125 g).

Electrospray MS [M+1] 712.4.

Step 2:

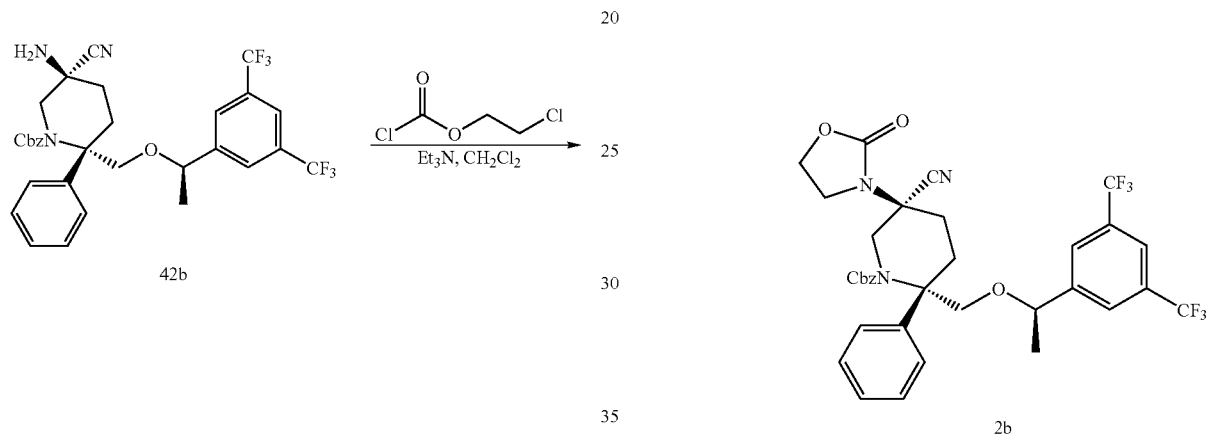

2a

2b

In a flame-dried 25 ml round-bottomed flask, Compound 2a (0.125 g, 0.175 mmol, 1.0 equiv) was taken up in dry THF. To this reaction mixture, 60% NaH (0.10 g, 0.26 mmol, 1.5 equiv) was added and reaction mixture was stirred at room temperature overnight. The progress of the reaction was monitored by TLC (40:60 EtOAc/hexane) and MS. Upon completion of the reaction, the reaction mixture was diluted with EtOAc and quenched with saturated aqueous NaHCO₃. The organic layer was dried over Na₂SO₄ and concentrated to give Compound 2b (0.11 g), which was used in the next step without further purification.

Electrospray MS [M+1] 676.2.

Step 3:

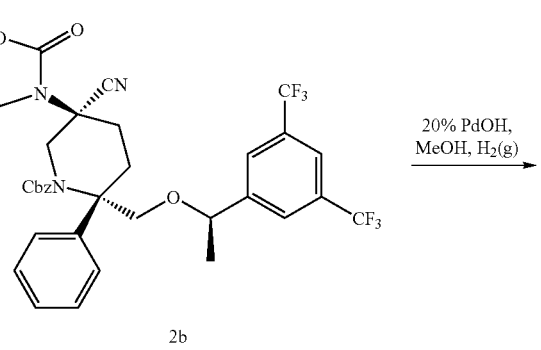

2b

-continued

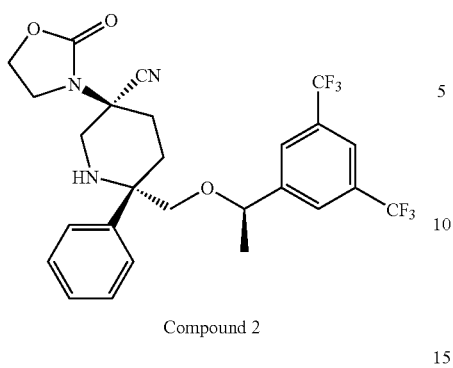

Compound 2

Compound 2b (0.11 g, 0.16 mmol, 1.0 equiv) was dissolved in dry MeOH (2.0 mL) and was treated with 20% Pd(OH)$_2$ (60% wt.) under an inert atmosphere. The reaction mixture was hydrogenated at atmospheric pressure and the progress of the reaction was monitored by TLC (40:60 EtOAc/hexane). The reaction was completed in 45 min, filtered through CELITE, washed with EtOAc, and concentrated to give a crude product. The crude product was purified using preparative plate chromatography (45/55 EtOAc/hexane) to give Compound 2 (0.04 g, 45%).

Electrospray MS [M+1] 542.3.

HRMS (FAB) calculated for $C_{28}H_{26}F_6N_3O_3$ (M+1) 542.1897. found 542.1878.

Preparative Example 3 and Example 4

Example 3

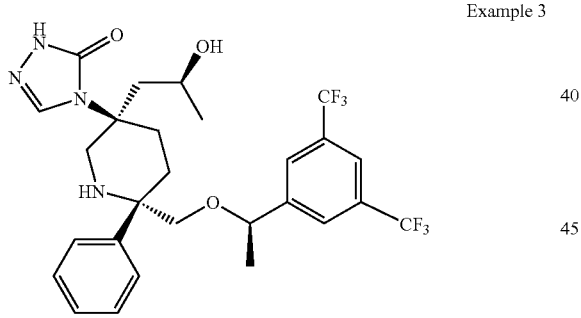

Example 4

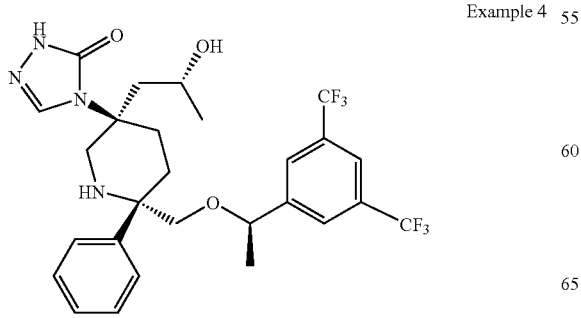

-continued

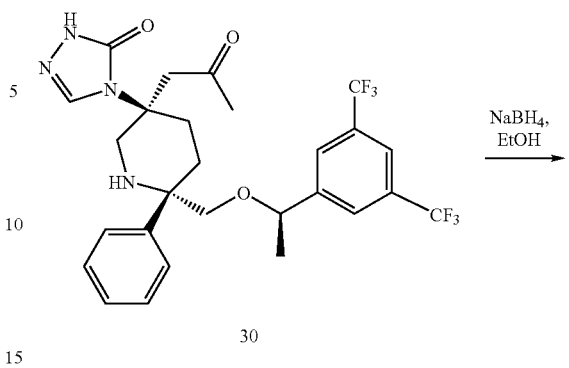

30

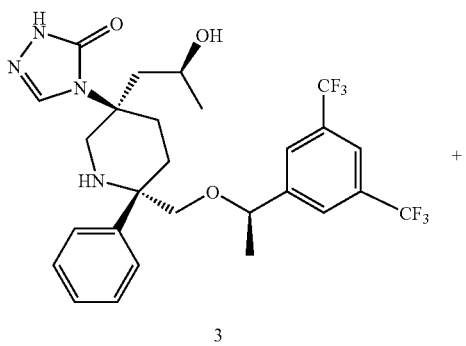

3

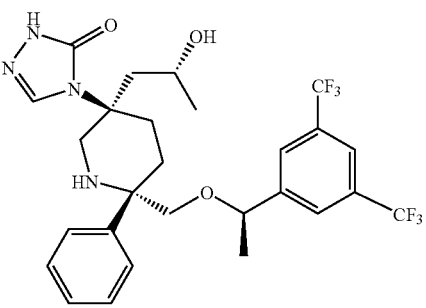

4

NaBH$_4$ (60 mg, 1.53 mmol, 8 equiv.) was added in portions to a solution of Compound 30 (109 mg, ~0.19 mmol, 1 equiv.) in absolute ethanol (2 mL) at 0° C. After stirring at 0° C. for 30 minutes, TLC (MeOH/CH$_2$Cl$_2$=10%) analysis of the reaction mixture showed only product. The product was purified by BIOTAGE chromatography (2-10% MeOH in CH$_2$Cl$_2$), to provide a pure mixture of two diastereomers. The two diastereomers were separated using Chiral HPLC (ChialCel OD, IPA/Hexane=10%) to give Example 3, MS [M+1]+ 573.1; and Example 4, MS [M+1]+ 573.1.

Preparative Example 5

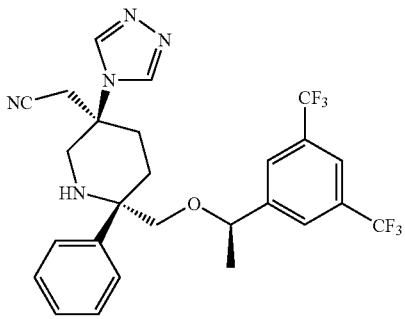

Compound 5

Step A:

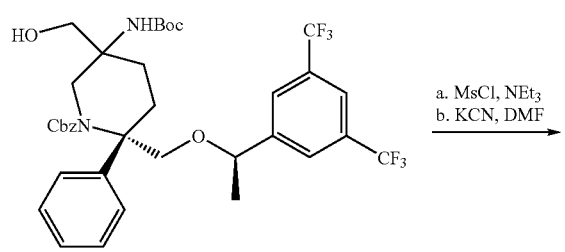

MsCl (0.102 mL, 1.32 mmol) was added to a solution of Compound 26a (0.375 g, 0.528 mmol) and Et₃N (0.368 mL, 2.64 mmol) in CH₂Cl₂ (5.0 mL) at 0° C. The reaction mixture was quenched with water (15.0 mL) after 30 minutes and then diluted with CH₂Cl₂ (50 mL). The resulting aqueous phase was extracted with CH₂Cl₂ (3×10 mL). The combined organic layers were washed with water (10 mL), brine (10 mL), and dried over MgSO₄. After filtration and concentration, the crude mesylate was taken up in DMF (3.0 mL) and treated with KCN (0.344 g, 5.28 mmol). The resulting mixture was heated at 100° C. for 12 hours before it was cooled to room temperature. The reaction mixture was diluted with EtOAc (100 mL) and washed with water (3×15 mL). The organic layer was then washed with brine (25 mL), and dried over MgSO₄. After filtration and concentration, the crude product was purified by BIOTAGE chromatography (hexane/EtOAc, v/v=7/1) to give Compound 5b (0.14 g, 37% for 2 steps).

Step B:

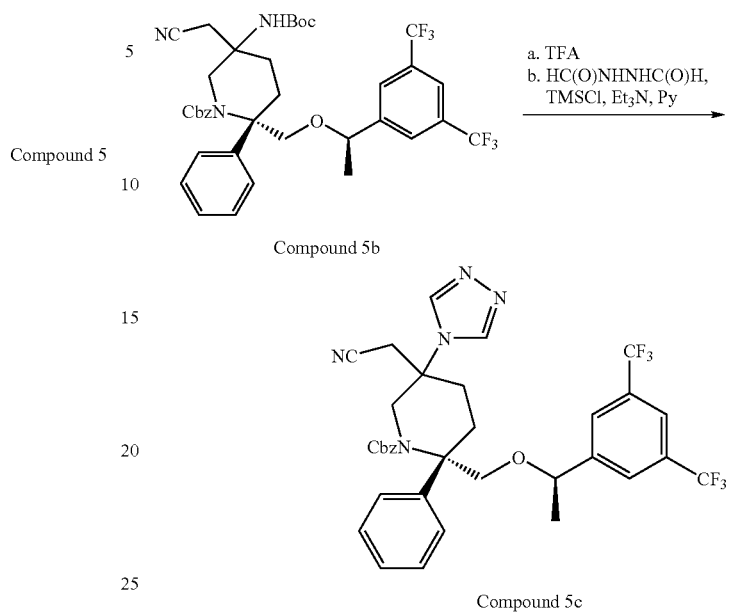

A solution of Compound 5b (0.14 g, 0.195 mmol) in TFA (2.5 mL) was stirred at room temperature for 20 minutes before the solvent was removed under reduced pressure. The residue was taken up in EtOAc (50 mL) and washed with a NaOH solution (4.0 N, 15 mL). The aqueous phase was extracted with EtOAc (3×10 mL). The combined organic layers were washed with water (15 mL), brine (15 mL), and then dried over MgSO₄. After filtration and concentration, the crude product was passed through a short pad of silica gel with EtOAc/MeOH (v/v=10/1) as eluent, to provide an amine (90 mg) after solvent removal. The amine was taken up in pyridine (1.0 mL) and treated with HC(O)NHNHC(O)H (38.3 mg, 0.435 mmol), TMSCl (0.276 mL, 2.175 mmol) and Et₃N (0.152 mL, 1.088 mmol) at room temperature in a sealed tube. The reaction mixture was then heated at 100° C. for 2.5 hours before it was cooled down to room temperature. The mixture was then diluted with EtOAc (40 mL) and washed with HCl (10 mL, 2.0 N). The resulting aqueous phase was extracted with EtOAc (3×15 mL). The combined organic layers were washed with water (15 mL), brine (25 mL), and dried over MgSO₄. After filtration and concentration, the crude product was purified using BIOTAGE chromatography (EtOAc/MeOH, v/v=10/1) to give Compound 5c (40 mg, 31% for 2 steps).

Step C:

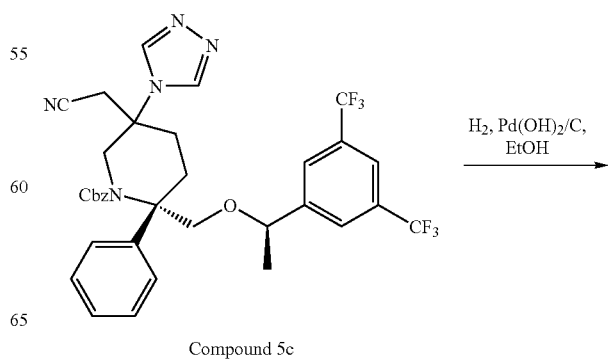

Compound 5c

Step A:

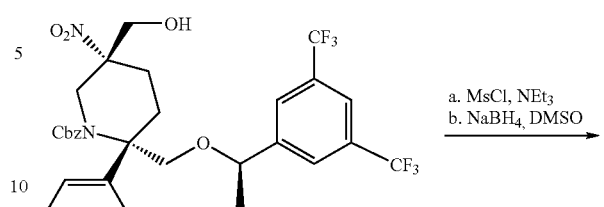

Compound 23d

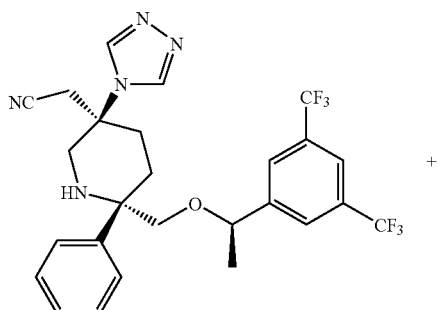

Compound 5

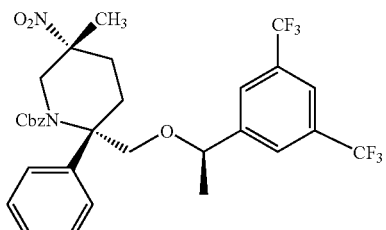

Compound 6a

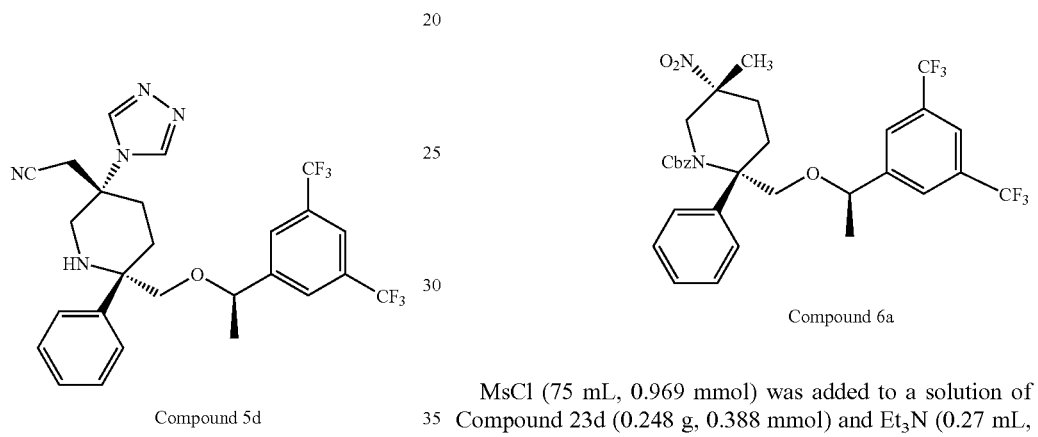

Compound 5d

Compound 5c (40 mg, 0.0595 mmol) in EtOH (2.0 mL) was treated at room temperature with Pd(OH)$_2$/C (8 mg, 10 wt %) and was hydrogenated using a H$_2$ balloon for 30 minutes. The reaction mixture was filtered through a short pad of CELITE and the residue was washed with EtOH (15 mL). Solvent was removed under reduced pressure, and the crude product was purified using preparative TLC (EtOAc/MeOH, v/v=40/1) to give Compound 5 (18 mg, 56%, Electrospray MS [M+1]$^+$ 538.1.) and Compound 5d (6 mg, 19%, Electrospray MS [M+1]$^+$ 538.1.).

Preparative Example 6

Compound 6

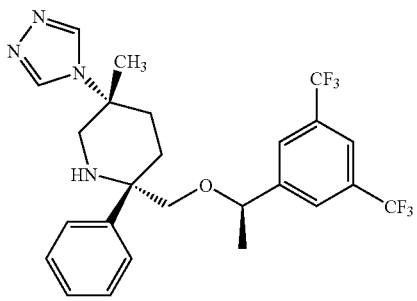

MsCl (75 mL, 0.969 mmol) was added to a solution of Compound 23d (0.248 g, 0.388 mmol) and Et$_3$N (0.27 mL, 1.94 mmol) in CH$_2$Cl$_2$ (3.0 mL) at room temperature. The reaction was quenched with water (10.0 mL) after 30 minutes and diluted with CH$_2$Cl$_2$ (30 mL). The aqueous phase was extracted with CH$_2$Cl$_2$ (3×10 mL). The combined organic layers were washed with water (10 mL), brine (10 mL), and dried over MgSO$_4$. After filtration and concentration, the crude mesylate was taken up in anhydrous DMSO (3.0 mL) and treated with NaBH$_4$ (59.0 mg, 1.552 mmol). The reaction mixture was heated at 85° C. for 48 hours before it was cooled down to room temperature. The mixture was then diluted with EtOAc (50 mL) and washed with aqueous HCl (10 mL, 1.0 M). The resulting aqueous phase was extracted with EtOAc (3×15 mL). The combined organic layers were washed with water (3×15 mL), brine (15 mL), and dried over MgSO$_4$. After filtration and concentration, the crude product was purified using BIOTAGE chromatography (hexane/EtOAc, v/v=5/1) to give Compound 6a (0.11 g, 45% for 2 steps).

Step B:

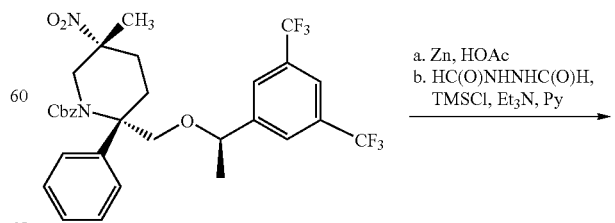

Compound 6a

-continued

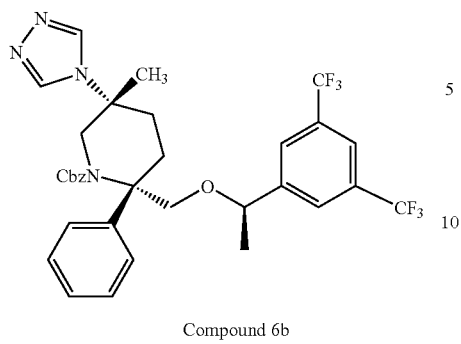

Compound 6b

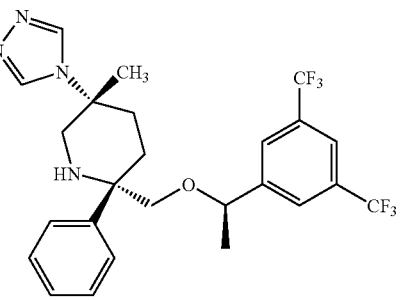

Compound 6

A mixture of Compound 6a (0.11 g, 0.176 mmol) and Zn dust (0.114 g, 1.76 mmol) in HOAc (1.5 mL) was heated at 60° C. for 2 hours. The reaction mixture was cooled down and filtered through a short pad of CELITE and the residue was washed with EtOH (15 mL). Solvent was removed under reduced pressure and the residue was taken up in EtOAc (25 mL) and washed with a NaOH solution (4.0 N, 10 mL). The resulting aqueous phase was extracted with EtOAc (3×10 mL). The combined organic layers were washed with water (15 mL), brine (15 mL), and dried over $MgSO_4$. After filtration and concentration, the crude amine (67.1 mg, 0.113 mmol) was taken up in pyridine (1.0 mL) and treated with HC(O)NHNHC(O)H (29.8 mg, 0.339 mmol), TMSCl (0.214 mL, 1.69 mmol) and $Et_3N$ (0.118 mL, 0.847 mmol) at room temperature in a sealed tube. The mixture was then heated at 100° C. for 2.5 hours before it was cooled down to room temperature. The mixture was then diluted with EtOAc (40 mL) and washed with HCl (10 mL, 2.0 N). The resulting aqueous phase was extracted with EtOAc (3×15 mL). The combined organic layers were washed with water (15 mL), brine (15 mL), and dried over $MgSO_4$. After filtration and concentration, the crude product was purified using BIOTAGE chromatography (EtOAc/MeOH, v/v=20/1) to give Compound 6b (37 mg, 33% for 2 steps).

Compound 6b (36.5 mg, 0.0565 mmol) in EtOH (2.0 mL) was treated at room temperature with $Pd(OH)_2/C$ (7.3 mg, 10 wt %) and was hydrogenated using a $H_2$ balloon for 30 minutes. The reaction mixture was filtered through a short pad of CELITE and the residue was washed with EtOH (15 mL). Solvent was removed under reduced pressure and the crude product was purified using preparative TLC (EtOAc/MeOH/ $Et_3N$, v/v/v=40/1/0.1) to give Compound 6 (20 mg, 69%). Electrospray MS $[M+1]^+$ 513.1.

Preparative Example 7

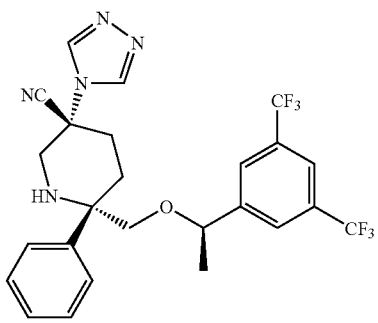

Compound 7

Step C:

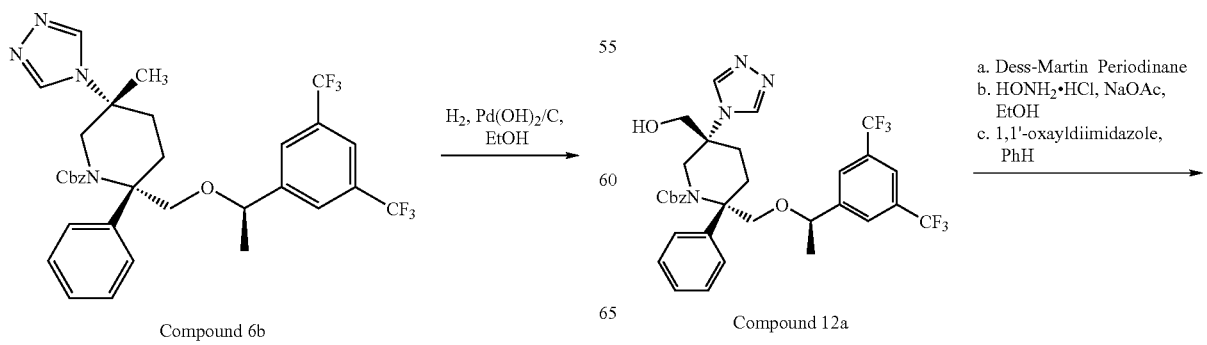

Step A:

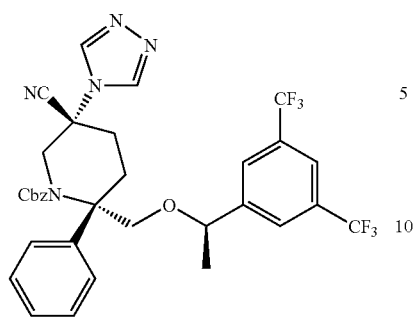

Compound 7a

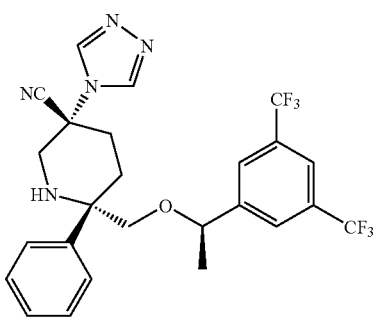

Compound 7

Dess-Martin Periodinane (0.114 g, 0.268 mmol) was added to a mixture of Compound 12a (70.5 mg, 0.107 mmol) and NaHCO$_3$ (0.112 g, 1.34 mmol) in CH$_2$Cl$_2$ (3.0 mL) at room temperature. The reaction was stirred for 1 hour before it was diluted with the addition of EtOAc (30 mL) and water (10 mL). The organic phase was washed with saturated Na$_2$S$_2$O$_3$ solution (3×10 mL). The combined aqueous phases were extracted with EtOAc (3×10 mL). The combined organic layers were washed with a NaOH solution (10 mL, 1.0 N), water (10 mL), brine (15 mL), and dried over MgSO$_4$. After filtration and concentration, the crude aldehyde (70.5 mg, 0.107 mmol) was dissolved in EtOH (3.0 mL) and treated with HONH$_2$.HCl (74.4 mg, 1.07 mmol) and NaOAc (43.9 mg, 0.535 mmol) at room temperature. The reaction mixture was stirred for 12 hours before it was diluted with EtOAc (20 mL) and washed with aqueous NaHCO$_3$ (10 mL). The aqueous phase was extracted with EtOAc (3×10 mL). The combined organic layers were washed with water (10 mL), brine (10 mL), and dried over MgSO$_4$. After filtration and concentration, the crude oxime was obtained (63 mg, 0.093 mmol) which was taken up in benzene (2.0 mL) and treated with 1,1'-oxalyldiimidazole (35.4 mg, 0.186 mmol). The reaction mixture was heated at 80° C. for 3 hours before it was cooled down to room temperature and diluted with EtOAc (20 mL) and washed with aqueous HCl (0.5 N, 5 mL). The aqueous phase was extracted with EtOAc (3×10 mL). The combined organic layers were washed with water (10 mL), brine (10 mL), and dried over MgSO$_4$. After filtration and concentration, the crude product was purified using BIOTAGE chromatography (EtOAc) to give Compound 7a (39 mg, 55% for 3 steps).

Step B:

Compound 7a (39 mg, 0.059 mmol) in EtOH (2.5 mL) was treated at room temperature with Pd(OH)$_2$/C (7.8 mg, 10 wt %) and was hydrogenated using a H$_2$ balloon for 30 minutes. The reaction solution was filtered through a short pad of CELITE and the residue was washed with EtOH (15 mL). Solvent was removed under reduced pressure and the crude product was purified using preparative TLC (EtOAc/Et$_3$N, v/v=100/0.1) to give Compound 7 (12.2 mg, 40%). Electrospray MS [M+1]$^+$ 524.3.

Preparative Example 8

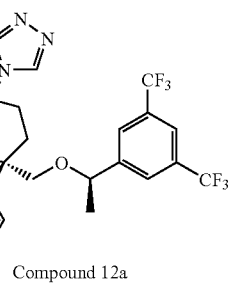

Compound 8

Step A:

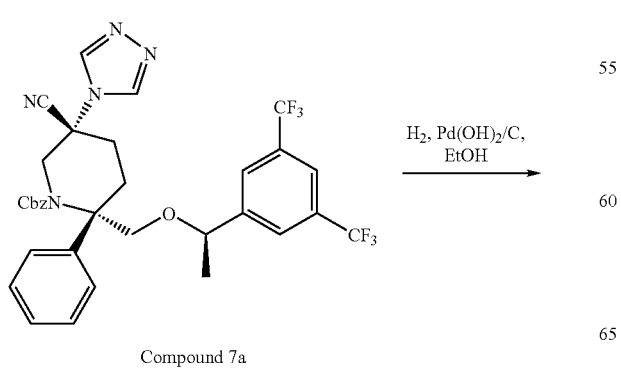

Compound 7a

H$_2$, Pd(OH)$_2$/C, EtOH
→

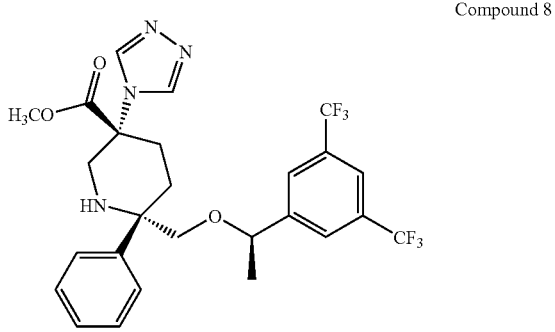

Compound 12a a. Dess-Martin Periodinane
b. 2-methyl-2-butene, NaClO$_2$ NaH$_2$PO$_4$, tert-butanol
c. TMSCHN$_2$, MeOH, PhH
→

-continued

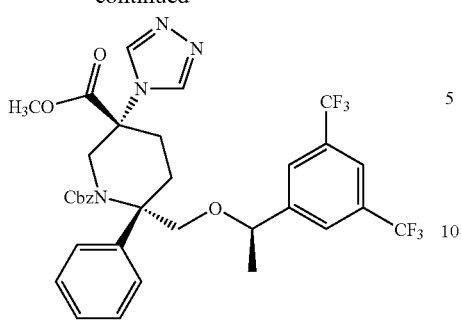

Compound 8a

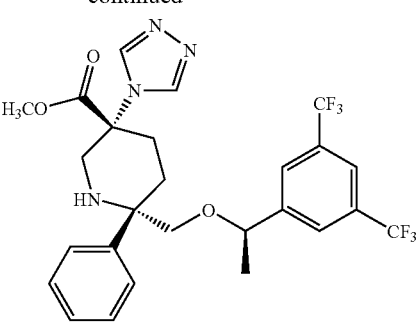

Compound 8

Dess-Martin Periodinane (0.325 g, 0.767 mmol) was added to a mixture of Compound 12a (0.202 g, 0.306 mmol) and NaHCO$_3$ (0.322 g, 3.83 mmol) in CH$_2$Cl$_2$ (5.0 mL) at room temperature. The reaction was stirred for 1 hour before it was diluted with EtOAc (50 mL) and water (10 mL). The organic phase was washed with saturated Na$_2$S$_2$O$_3$ solution (3×15 mL). The combined aqueous phases were extracted with EtOAc (3×15 mL). The combined organic layers were washed with NaOH solution (15 mL, 1.0 N), water (10 mL), brine (15 mL), and dried over MgSO$_4$. After filtration and concentration, the crude aldehyde (0.202 g) was taken up in tert-butanol (4.0 mL) and water (1.0 mL) and treated with NaH$_2$PO$_4$.H$_2$O (84.4 mg, 0.612 mmol), NaClO$_2$ (96.8 mg, 1.07 mmol) and 2-methyl-2-butene (0.227 mL, 2.14 mmol) successively. The reaction mixture was stirred for 2 hours and then diluted with EtOAc (30 mL) and washed with aqueous NH$_4$Cl. The resulting aqueous phase was extracted with EtOAc (3×10 mL). The combined organic layers were washed with water (10 mL), brine (10 mL), and dried over MgSO$_4$. After filtration and concentration, the crude acid was dissolved in benzene. (4.0 mL) and MeOH (1.0 mL). The resulting solution was treated with TMSCHN$_2$ (0.306 mL, 0.612 mmol) at room temperature and stirred for 20 minutes. Solvent was removed under reduced pressure and the crude product was purified using BIOTAGE chromatography (hexane/EtOAc, v/v=5/1 to 1/3) to give Compound 8a (62 mg, 29% for 3 steps).

Compound 8a (62 mg, 0.090 mmol) in EtOH (3.0 mL) was treated at room temperature with Pd(OH)$_2$/C (12.4 mg, 10 wt %) and was hydrogenated using a H$_2$ balloon for 30 minutes. The reaction mixture was filtered through a short pad of CELITE and the residua was washed with EtOH (15 mL). Solvent was removed under reduced pressure and the crude product was purified using BIOTAGE chromatography (EtOAc/MeOH, v/v=6/1) to give Compound 8 (42 mg, 84%). Electrospray MS [M+1]$^+$ 557.3.

Preparative Example 9

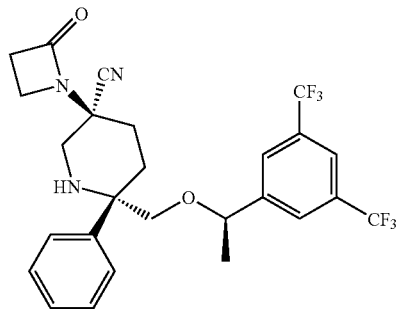

9

Step B:

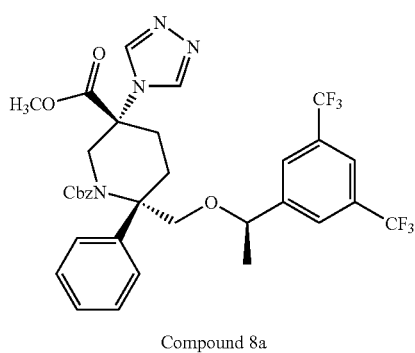

Compound 8a

Step 1:

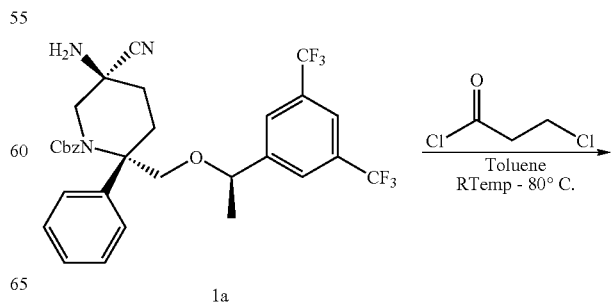

1a

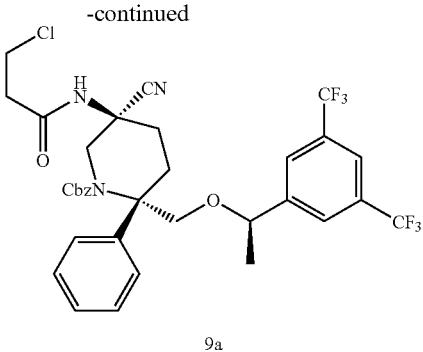

9a

In a 25 ml round-bottomed flask, Compound 42b (0.21 g, 0.35 mmol, 1.0 equiv) was taken up in 2 mL of toluene. 3-chloropropionyl chloride (0.037 mL, 0.38 mmol, 1.1 equiv) was then added to the reaction mixture, which was stirred at room temperature for five hrs. The progress of the reaction was monitored by TLC (60:40 EtOAc/hexane) and MS, which showed some starting material was still present. The reaction mixture was thus heated to 80° C. Upon completion of the reaction after a further hour of heating, the mixture was concentrated to give crude product Compound 9a (0.2 g), which was used in the next step without further purification.

Step 2:

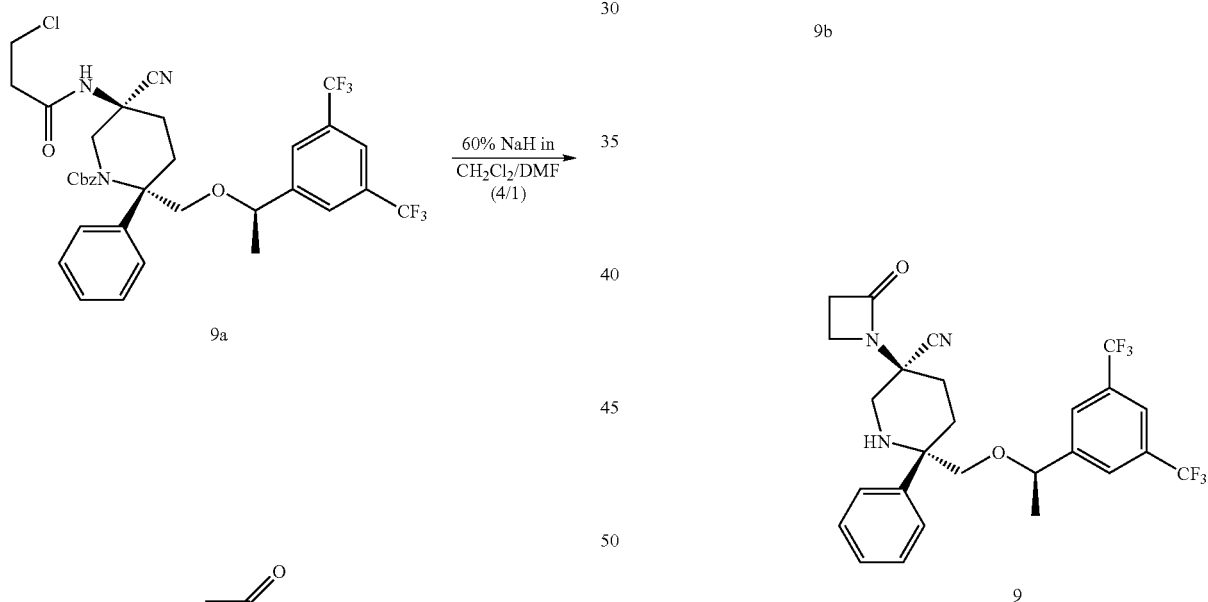

In a flame-dried 25 ml round-bottomed flask, Compound 9a (0.2 g, 0.287 mmol, 1.0 equiv) was taken up in a 0.5 M solution of dry $CH_2Cl_2$/DMF (4/1) ratio (4.59 mL/1.15 mL). To this mixture a 0.5 M solution of 60% NaH (0.012 g, 0.316 mmol, 1.1 equiv) in dry $CH_2Cl_2$/DMF (4/1 ratio; 5.06 mL/1.26 mL) was very slowly added using a syringe pump over a period of 3.5 hrs and the reaction mixture was stirred at room temperature overnight. The progress of the reaction was monitored by TLC (40:60 EtOAc/hexane) and MS. The reaction went to 60% completion, and was then diluted with $CH_2Cl_2$ and quenched with saturated aqueous $NH_4Cl$. The organic layer was dried over $Na_2SO_4$ and concentrated to give crude product (0.18 g), which was purified using BIOTAGE chromatography (arm EtOAc/hexane) to give Compound 9b (0.125 g).

Electrospray MS [M+1] 660.2.

Step 3:

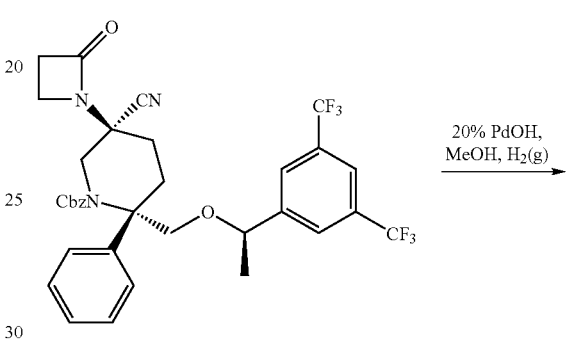

Compound 9b (0.125 g, 0.189 mmol, 1.0 equiv) was dissolved in dry MeOH (1.0 mL) and was treated with 20% $Pd(OH)_2$ (60% wt.) under an inert atmosphere. The reaction mixture was hydrogenated at atmospheric pressure and the progress of the reaction was monitored by TLC (60:40 EtOAc/hexane). The reaction was completed in 20 min, and the reaction mixture was filtered through CELITE, washed using EtOAc, and concentrated to give crude product. Purification was carried out using prep plate chromatography (45/55 EtOAc/hexane) to give Compound 9 (0.071 g, 71%).

Electrospray MS [M+1] 526.3.

HRMS (FAB) calculated for $C_{26}H_{26}F_6N_3O_2$(M+1) 526.1932. found 526.1929.

Preparative Example 10

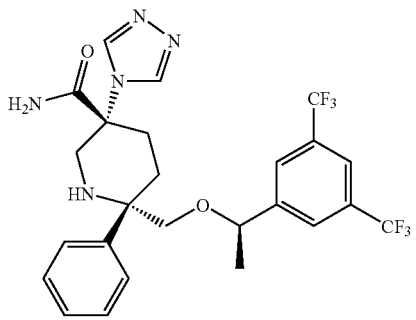

Compound 10

Step A:

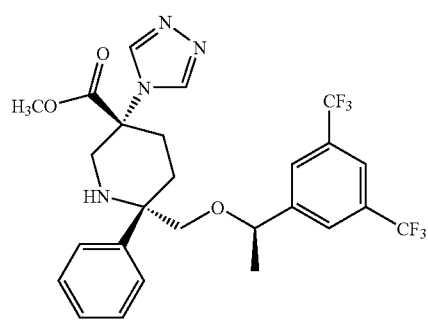

Compound 8

→ NH₃, MeOH →

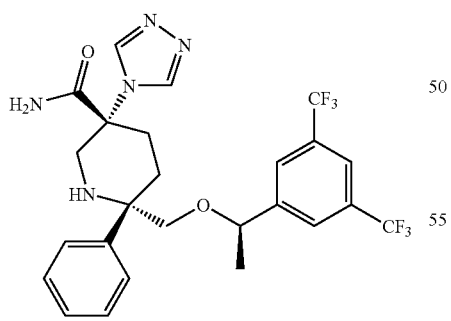

Compound 10

A solution of Compound 8 (35 mg, 0.063 mmol) in ammonia methanol solution (3.0 mL, 7.0 M) in a Parr bomb was heated at 80° C. for 5 days. The system was cooled to room temperature and solvent was removed under reduced pressure. The crude product was purified using BIOTAGE chromatography (EtOAc/MeOH, v/v=10/1) to give Compound 10 (26.8 mg, 79%). Electrospray MS [M+1]⁺ 542.1.

Preparative Example 11

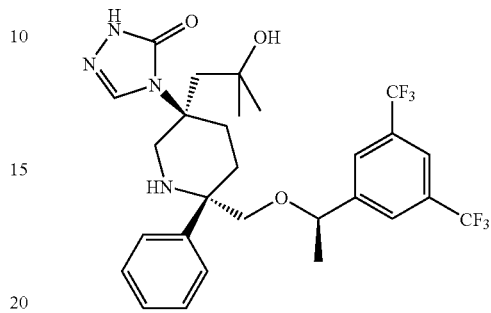

Example 11

Step 1:

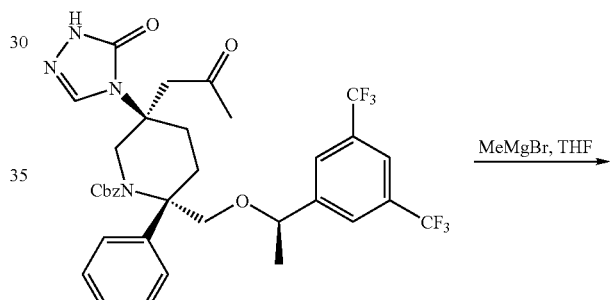

→ MeMgBr, THF →

11a

A solution of methylmagnesium bromide in tert-butylether (0.42 mL, 1.0M, 0.42 mmol, 6.2 equiv.) was syringed into a solution of Compound 30b (48 mg, 0.068 mmol, 1.0 equiv.) in anhydrous THF (1 mL) at 0° C. The reaction mixture was then warmed up to room temperature. After TLC (EtOAc eluent) showed that the reaction was complete, the reaction mixture was diluted with ether and washed with saturated aqueous NH₄Cl solution. The combined organic layers were dried over MgSO₄, filtered and concentrated to give crude product, Compound 11a, which was used in the next step without purification.

Step 2:

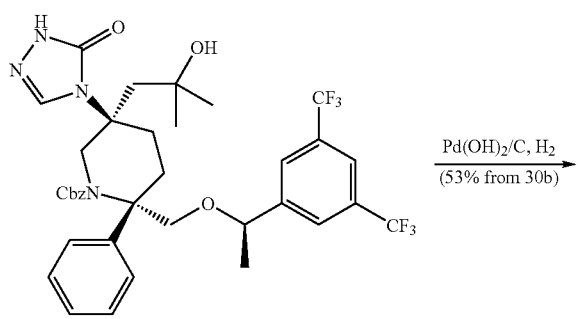

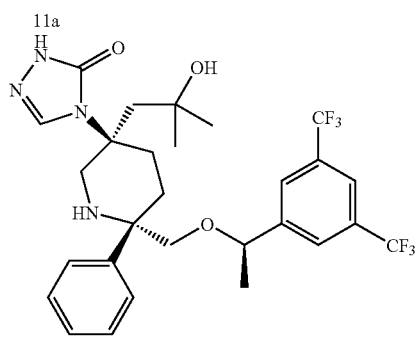

Using the same procedure as that of Example 31, Step 6, the crude Compound 11a was hydrogenated to give pure Example 30b (yield 52.6% from Compound 11). MS [M+1]+ 587.1.

Preparative Example 12

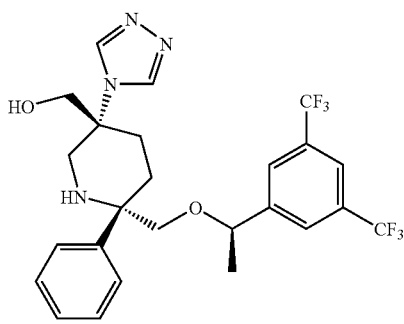

Compound 12

Step A:

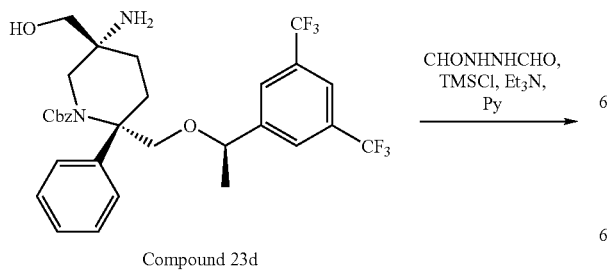

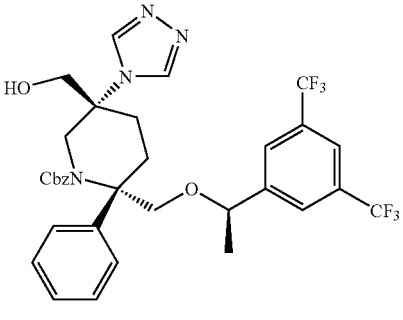

Compound 12a

HC(O)NHNHC(O)H (0.28 g, 3.18 mmol), TMSCl (2.0 mL, 15.9 mmol) and Et$_3$N (1.1 mL, 7.95 mmol) were added successively to a solution of Compound 23d (0.647 g, 1.06 mmol) in pyridine (5.0 mL) at room temperature in a sealed tube. The mixture was then heated at 100° C. for 2.5 hours before it was cooled down to room temperature. The mixture was then diluted with EtOAc (100 mL) and washed with HCl (35 mL, 2.0 N). The aqueous phase was extracted with EtOAc (3×25 mL), and the combined organic layers were washed with water (15 mL), brine (25 mL), and dried over MgSO$_4$. After filtration and concentration, the crude product was purified using BIOTAGE chromatography (EtOAc/MeOH, v/v=5/1) to give Compound 12a (0.48 g, 68%).

Step b:

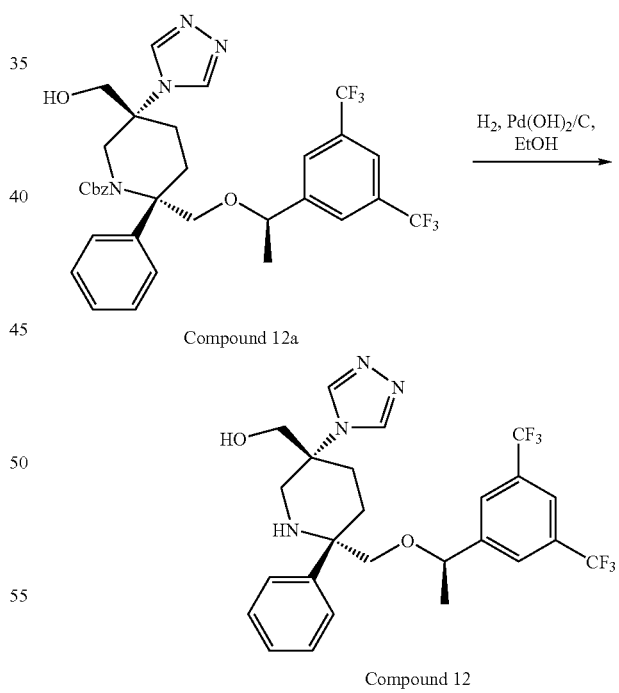

Compound 12a (32.6 mg, 0.049 mmol) in EtOH (2.0 mL) was treated at room temperature with Pd(OH)$_2$/C (6.5 mg, 10 wt %) and was hydrogenated using a H$_2$ balloon for 30 minutes. The reaction mixture was then filtered through a short pad of CELITE and the residue was washed with EtOH (15 mL). The solvent was removed under reduced pressure and the crude product was purified using BIOTAGE chromatography (EtOAc/MeOH eluent, v/v=6/1) to give Compound 12 (17.2 mg, 66%). Electrospray MS [M+1]+ 529.1.

Preparative Example 13 and 14

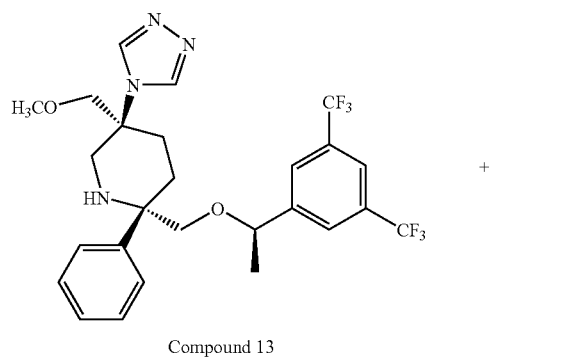

Compound 13

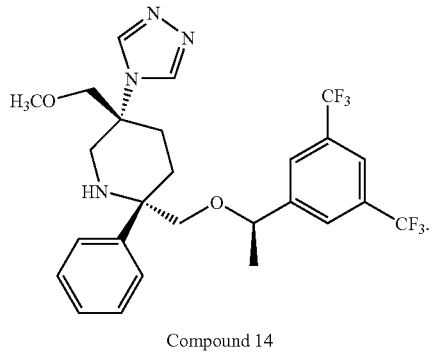

Compound 14

Step A:

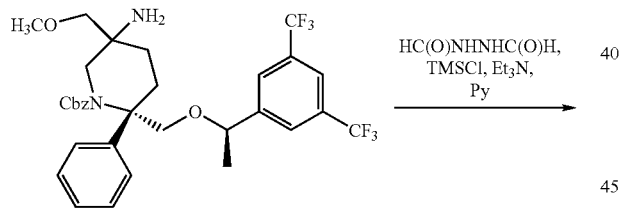

HC(O)NHNHC(O)H (67.1 mg, 0.762 mmol), TMSCl (0.484 mL, 3.81 mmol) and Et₃N (0.266 mL, 1.905 mmol) were added successively to a solution of Compound 26a (0.155 g, 0.254 mmol) in pyridine (2.0 mL) at room temperature in a sealed tube. The mixture was then heated at 100° C. for 2.5 hours before it was cooled down to room temperature. The mixture was diluted with EtOAc (40 mL) and washed with HCl (15 mL, 2.0 N). The aqueous phase was extracted with EtOAc (3×15 mL). The combined organic layers were washed with water (15 mL), brine (25 mL), and dried over MgSO₄. After filtration and concentration, the crude product was purified using BIOTAGE chromatography (EtOAc/MeOH, v/v=10/1) eluent to give Compound 14a (0.129 g, 75%).

Step B:

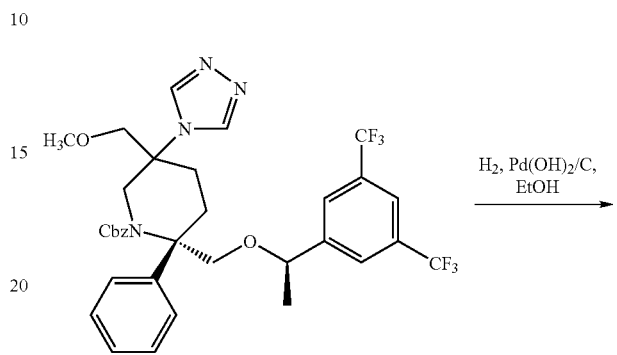

Compound 14a

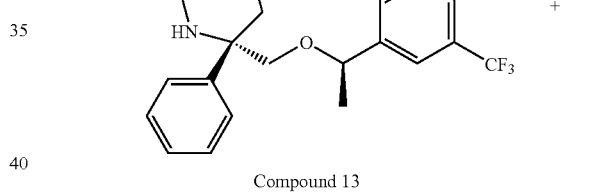

Compound 13

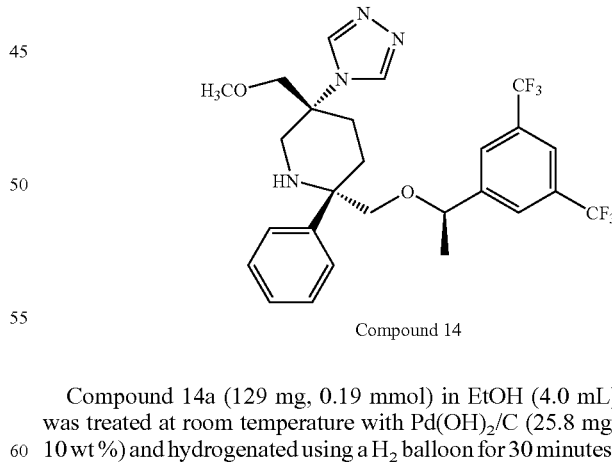

Compound 14

Compound 14a (129 mg, 0.19 mmol) in EtOH (4.0 mL) was treated at room temperature with Pd(OH)₂/C (25.8 mg, 10 wt %) and hydrogenated using a H₂ balloon for 30 minutes. The reaction mixture was filtered through a short pad of CELITE and the residue was washed with EtOH (15 mL). Solvent was removed under reduced pressure and the crude product was purified using preparative TLC (EtOAc/Et₃N, v/v=100/0.1) to give Compound 13 (36 mg, 35%, Electrospray MS [M+1]+ 543.1.) and Compound 14 (30 mg, 29%, Electrospray MS [M+1]+ 543.1.).

Preparative Example 15

Compound 15

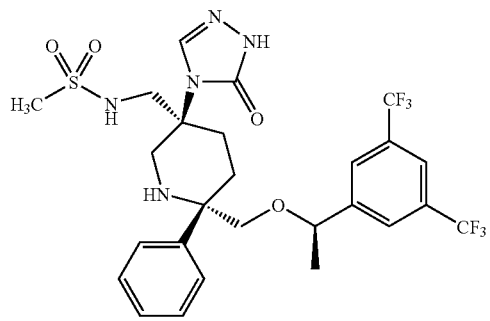

Step A:

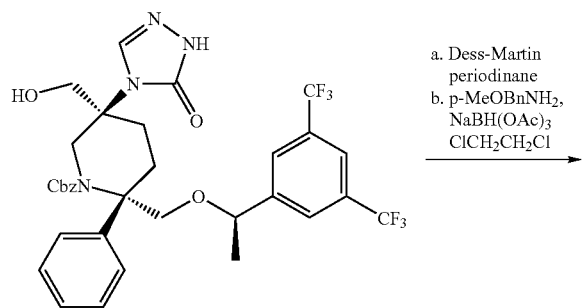

Compound 23g a. Dess-Martin periodinane
b. p-MeOBnNH$_2$, NaBH(OAc)$_3$ ClCH$_2$CH$_2$Cl
→

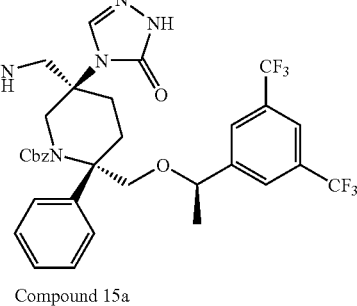

Compound 15a

Dess-Martin Periodinane (57.7 mg, 0.136 mmol) was added to a mixture of Compound 23g (46 mg, 0.0678 mmol) and NaHCO$_3$ (57 mg, 0.678 mmol) in CH$_2$Cl$_2$ (2.5 mL) at room temperature. The reaction mixture was stirred for 1 hour before it was diluted with EtOAc (20 mL) and water (10 mL). The organic phase was washed with saturated Na$_2$S$_2$O$_3$ solution (3×10 mL). The combined aqueous phases were extracted with EtOAc (3×10 mL). The combined organic layers were washed with NaOH solution (10 mL, 1.0 N), water (10 mL), brine (15 mL), and dried over MgSO$_4$. After filtration and concentration, the crude aldehyde (46 mg, 0.0679 mmol) was taken up in ClCH$_2$CH$_2$Cl (1.0 mL) and treated with 4 Å molecular sieves (15 mg) and para-methoxybenzyl amine (26.7 µl, 0.204 mmol), followed with addition of NaBH(OAc)$_3$ (86.4 mg, 0.408 mmol). The resulting reaction mixture was stirred at room temperature for 12 hours. The system was then diluted with EtOAc (20 mL) and washed with aqueous NaHCO$_3$ (10 mL). The aqueous phase was extracted with EtOAc (3×10 mL). The combined organic layers were washed with water (10 mL), brine (10 mL), and dried over MgSO$_4$. After filtration and concentration, the crude product was purified using BIOTAGE chromatography (hexane/EtOAc, v/v=2/3) to give Compound 15a (38 mg, 70% for 2 steps).

Step B:

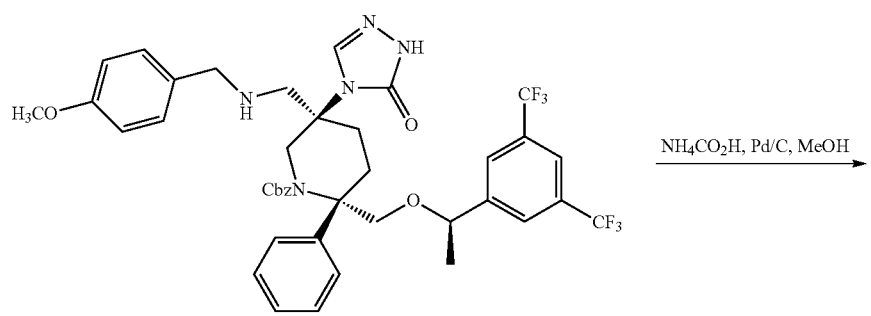

Compound 15a

NH$_4$CO$_2$H, Pd/C, MeOH →

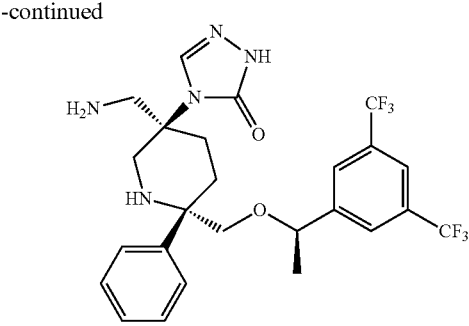

Compound 15b

A mixture of Compound 15a (46.6 mg, 0.0584 mmol), Pd/C (46.6 mg, 10 wt %), and NH$_4$CO$_2$H (36.8 mg, 0.584 mmol) in MeOH (2.0 mL) was heated at reflux for 5 hours. The mixture was cooled to room temperature and filtered through a short pad of CELITE, and the residue was washed with EtOH (15 mL). Solvent was removed under reduced pressure to give a crude product, which was taken up with EtOAc (20 mL) and washed with aqueous NaHCO$_3$ (10 mL). The aqueous phase was extracted with EtOAc (3×10 mL). The combined organic layers were washed with water (10 mL), brine (10 mL), and dried over MgSO$_4$. After filtration and concentration, the crude product was purified using preparative TLC (MeOH/EtOAc, v/v=1/10) to give Compound 15b (18 mg, 57%).

Step C:

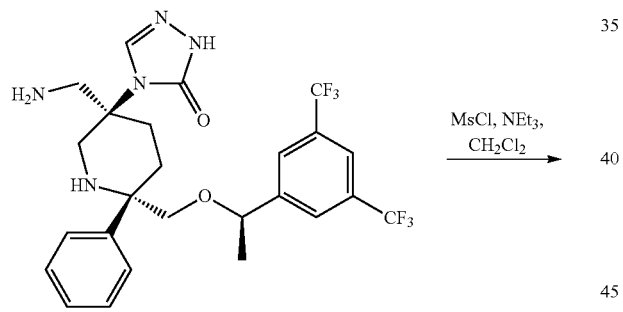

Compound 15b

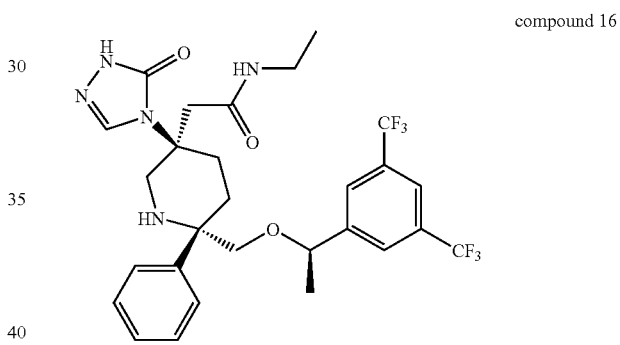

Compound 15

MsCl (2.5 μL, 0.0324 mmol) was added to a solution of Compound 15b (8.8 mg, 0.0162 mmol) and Et$_3$N (5.4 μL, 0.0388 mmol) in CH$_2$Cl$_2$ (1.0 mL) at 0° C. The reaction was quenched with water (5.0 mL) in 30 minutes and diluted with EtOAc (15 mL). The aqueous phase was extracted with EtOAc (3×10 mL). The combined organic layers were washed with water (10 mL), brine (10 mL), and dried over MgSO$_4$. After filtration and concentration, the crude product was purified using preparative TLC (hexane/EtOAc, v/v=1/5) to give Compound 15 (7.2 mg, 72%). Electrospray MS [M+1]$^+$ 622.3.

Preparative Example 16

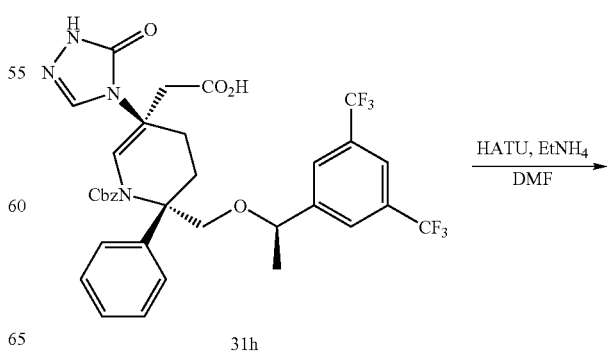

compound 16

Step 1:

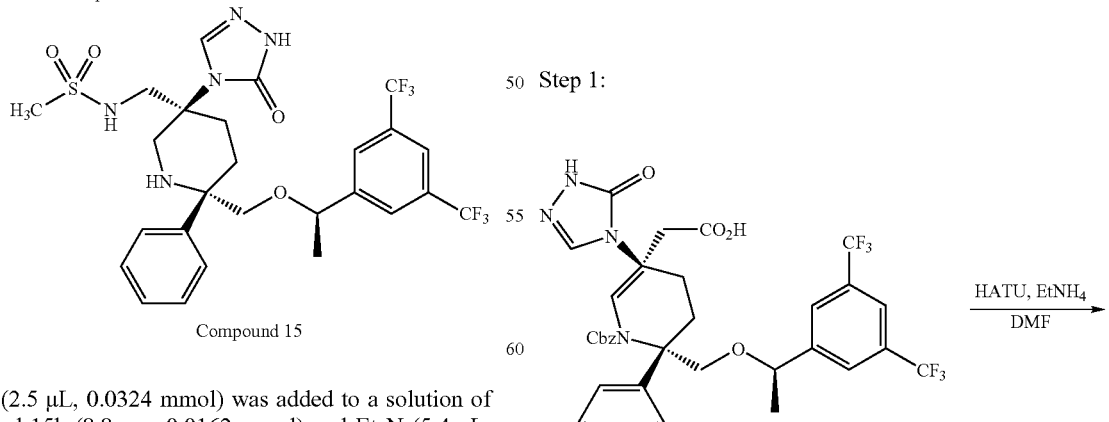

31h

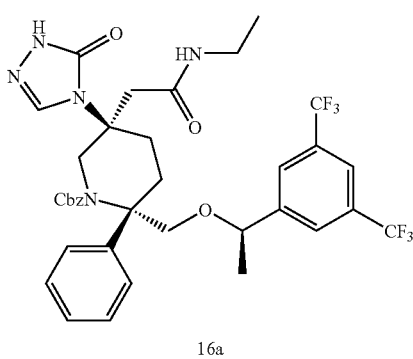

16a

Using the same procedure as that of Example 30, Step 1, Compound 16a was prepared using ethylamine in the place of N,N-dimethylamine hydrochloride salt, and without using diisopropyl ethyl amine. The crude product was used in the next step without purification.

Step 2:

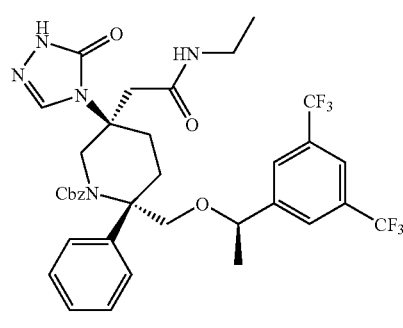

16a

Pd(OH)₂/C, H₂
(71% from CW8)

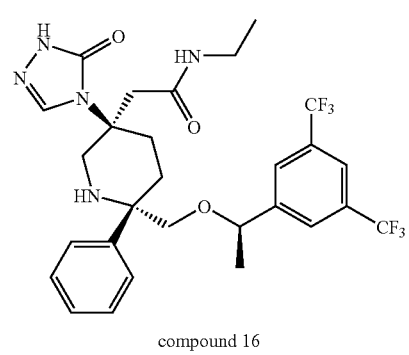

compound 16

Using the same procedure as that of Example 31, Step 6, the crude Compound 16a was hydrogenated to give pure Example 16 (yield 70.5% from Compound 16). MS [M+1]⁺ 600.1.

Preparative Example 17

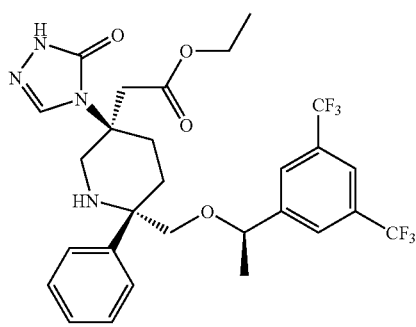

Example 17

Step 1:

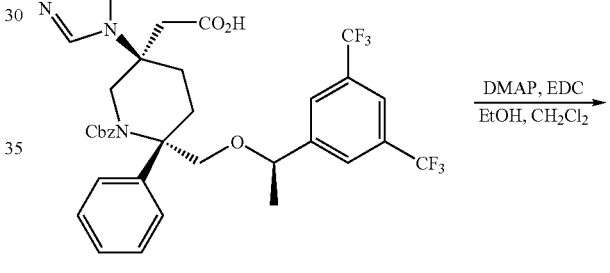

31h

DMAP, EDC
EtOH, CH₂Cl₂

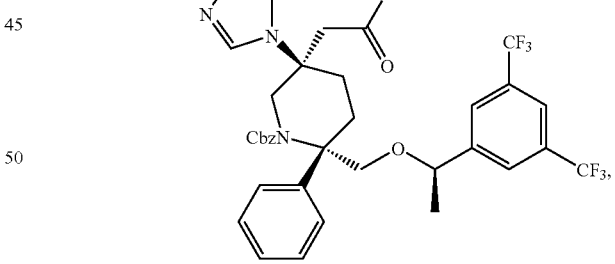

17a

A solution of Compound 31h (46.3 mg, 0.066 mmol, 1.0 equiv.) in anhydrous dichloromethane (1 mL) was cooled to 0° C. To this solution was added sequentially DMAP (8 mg, 0.066 mmol, 1.0 equiv.), and ethanol (36 µL). The reaction mixture was allowed to warm up to room temperature, and then concentrated to dryness. The residue was taken up into EtOAc and washed with saturated aqueous NaHCO₃ solution. The organic layer was dried over Na₂SO₄, filtered and concentrated to give the crude product, Compound 17a, which was used in the next step without purification.

Step 2:

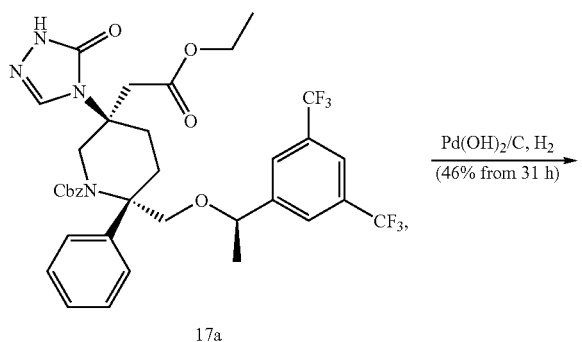

17a

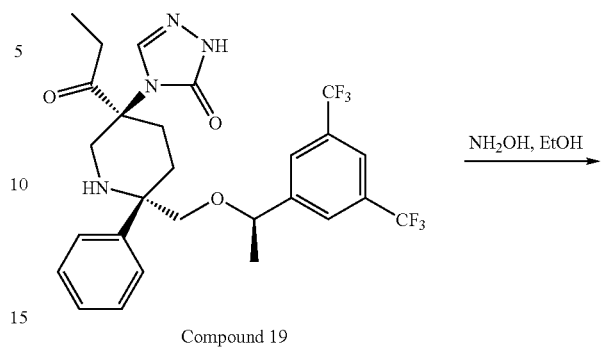

Compound 19

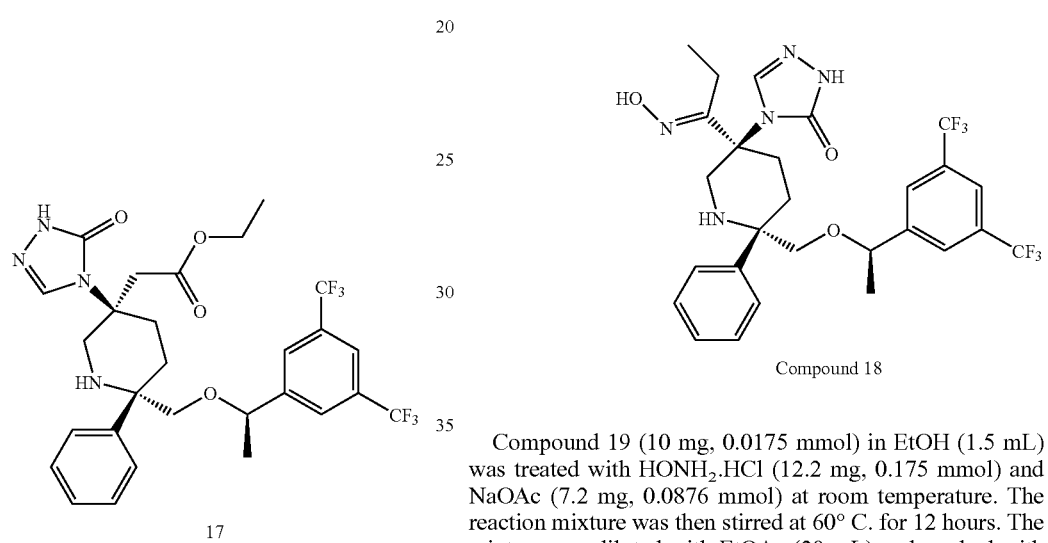

17

Compound 18

Using the same procedure as that of Example 31, Step 6, the crude Compound 17a was hydrogenated to give pure 17 (yield 46% from Compound 31h). MS [M+1]$^+$ 601.1.

Step A:

Compound 19 (10 mg, 0.0175 mmol) in EtOH (1.5 mL) was treated with HONH$_2$.HCl (12.2 mg, 0.175 mmol) and NaOAc (7.2 mg, 0.0876 mmol) at room temperature. The reaction mixture was then stirred at 60° C. for 12 hours. The mixture was diluted with EtOAc (20 mL) and washed with aqueous NaHCO$_3$. The aqueous phase was extracted with EtOAc (3×10 mL). The combined organic layers were washed with water (10 mL), brine (10 mL), and dried over MgSO$_4$. After filtration and concentration, the crude product was purified by preparative TLC (hexane/EtOAc, v/v=2/3) to give Compound 18 (10 mg, 98%). Electrospray MS [M+1]$^+$ 586.1.

Preparative Example 18

Compound 18

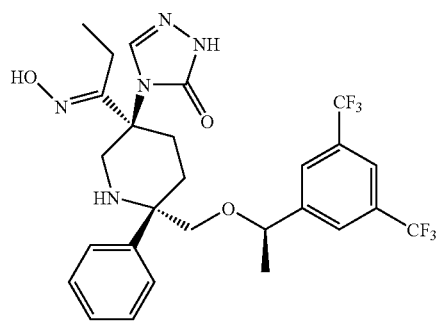

Preparative Example 19

Compound 19

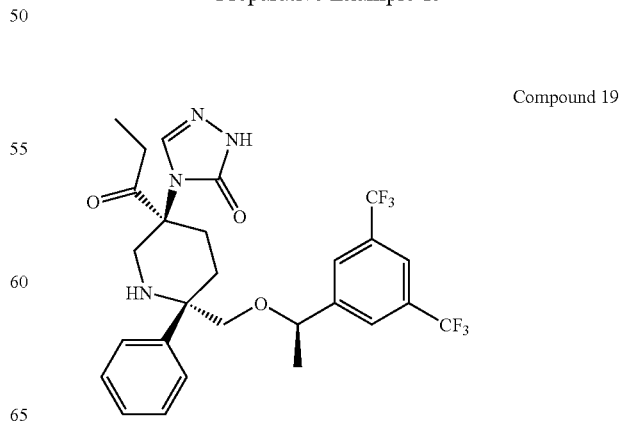

Step A:

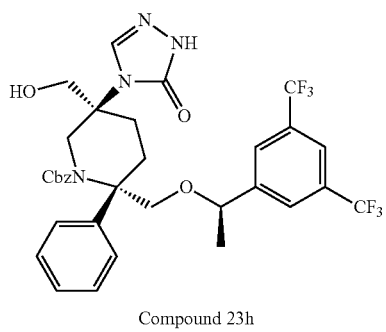

Compound 23h

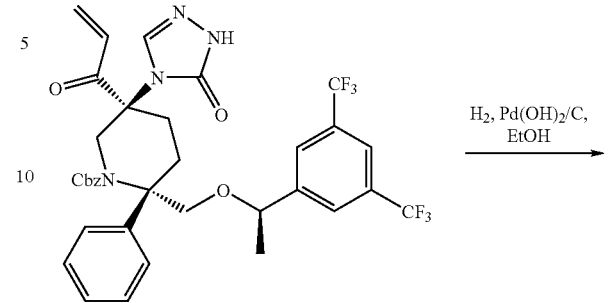

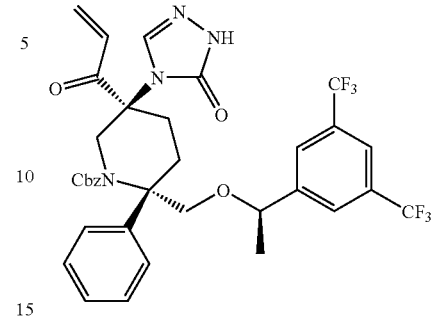

Compound 19a

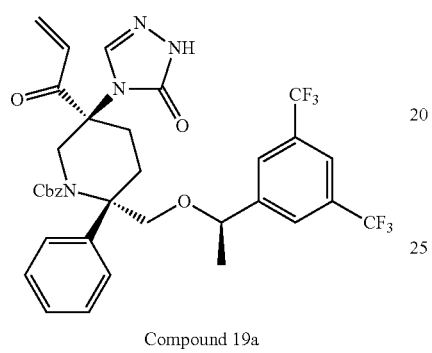

Compound 19a

Dess-Martin Periodinane (0.252 g, 0.595 mmol) was added to a mixture of Compound 23h (0.202 g, 0.297 mmol) and NaHCO$_3$ (0.25 g, 2.97 mmol) in CH$_2$Cl$_2$ (4.0 mL) at room temperature. The reaction mixture was stirred for 1 hour before it was diluted with EtOAc (50 mL) and water (10 mL). The organic phase was washed with a saturated Na$_2$S$_2$O$_3$ solution (3×15 mL). The combined aqueous phases were extracted with EtOAc (3×15 mL). The combined organic layers were washed with NaOH solution (15 mL, 1.0 N), water (10 mL), brine (15 mL), and dried over MgSO$_4$. After filtration and concentration, the crude aldehyde (0.202 g) was taken up in anhydrous THF (4.0 mL) and was treated with CH$_3$MgBr (1.19 mL, 1.19 mmol, 1.0 M in THF) at −78° C. The reaction temperature was slowly increased to room temperature and the reaction was quenched in 2 hours by the slow addition of saturated aqueous NH$_4$Cl solution (10 mL). The reaction mixture was then diluted with EtOAc (50 mL) and neutralized with 0.5 N HCl until the aqueous phase was slightly acidic. The aqueous phase was extracted with EtOAc (3×15 mL). The combined organic layers were wasted with water (10 mL), brine (10 mL), and dried over MgSO$_4$. After filtration and concentration, the crude secondary alcohol (0.21 g) was taken up in CH$_2$Cl$_2$ (5.0 mL) and treated with Dess-Martin Periodinane (0.379 g, 0.894 mmol) and NaHCO$_3$ (0.375 g, 4.47 mmol) at room temperature. The reaction mixture was stirred for 1 hour before it was diluted with EtOAc (50 mL) and water (10 mL). The organic phase was washed with saturated Na$_2$S$_2$O$_3$ solution (3×15 mL). The combined aqueous phases were extracted with EtOAc (3×15 mL). The combined organic layers were washed with aqueous NaOH solution (15 mL, 1.0 N), water (10 mL), brine (15 mL), and dried over MgSO$_4$. After filtration and concentration, the crude produce was purified using BIOTAGE chromatography (hexane/EtOAc, v/v=1/1) to give Compound 19a (90 mg, 43% for 3 steps).

Step B:

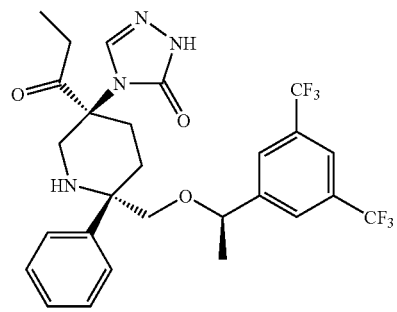

Compound 19

Compound 19a (57.4 mg, 0.0816 mmol) in EtOH (3.0 mL) was treated at room temperature with Pd(OH)$_2$/C (11.5 mg, 10 wt %) and was hydrogenated using a H$_2$ balloon for 30 minutes. The reaction mixture was filtered through a short pad of CELITE and the residue was washed with EtOH (15 mL). Solvent was removed under reduced pressure and the crude product was purified using BIOTAGE chromatography (hexane/EtOAc, v/v=2/3) to give Compound 19 (41 mg, 88%). Electrospray MS [M+1]$^+$ 571.1.

Preparative Example 20

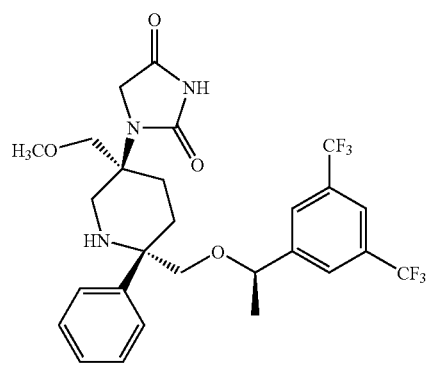

Compound 20

Step A:

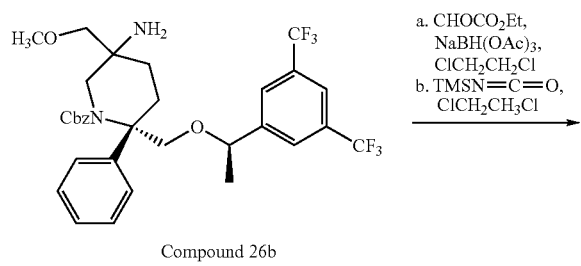

Compound 26b

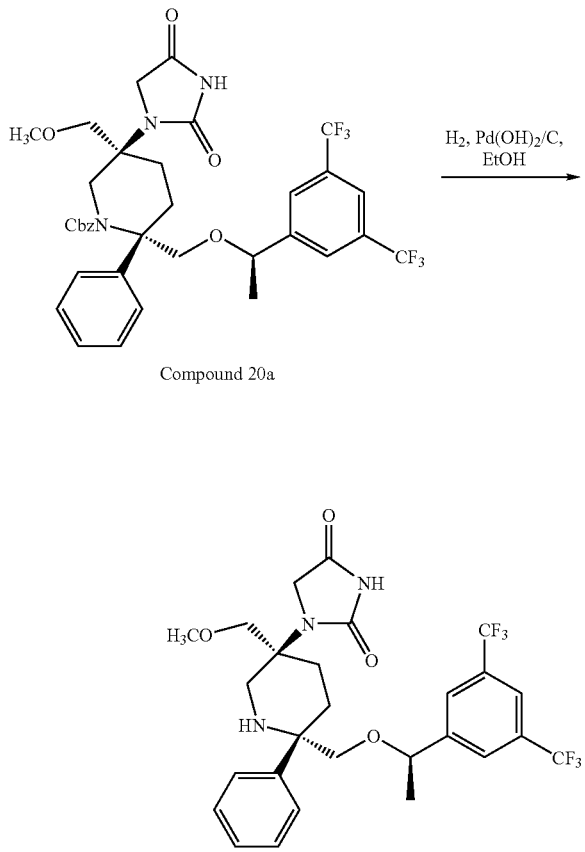

NaBH(OAc)₃ (81.4 mg, 0.384 mmol) was added at room temperature to a solution of Compound 26b (79.9 mg, 0.128 mmol), CHOCO₂Et (37.8 μ, 0.192 mmol, 45-50% in toluene), and 4 Å molecular sieves (30 mg) in ClCH₂CH₂Cl (1.0 mL). The reaction mixture was stirred for 12 hours before it was diluted with EtOAc (20 mL) and washed with aqueous NaHCO₃ (10 mL). The aqueous phase was extracted with EtOAc (3×10 mL). The combined organic layers were washed with water (10 mL), brine (10 mL), and dried over MgSO₄. After filtration and concentration, the crude product (91 mg, 0.128 mmol) was taken up in ClCH₂CH₂Cl (0.5 mL) and treated with TMSN=C=O (2.5 mL). The reaction mixture was heated at 70° C. for 72 hours before the solvent was removed under reduced pressure. The crude product was purified using BIOTAGE chromatography (hexane/EtOAc, v/v=1/1) to give a mixture of Compound 20a and 20b, which was further purified by OD chiral HPLC to give pure Compound 20a (30 mg, 33%) and Compound 20b (25 mg, 28%).

Step B:

Compound 20a (23 mg, 0.0325 mmol) in EtOH (2.0 mL) was treated at room temperature with Pd(OH)₂/C (4.6 mg, 10 wt %) and was hydrogenated using a H₂ balloon for 30 minutes. The reaction solution was filtered through a short pad of CELITE and the residue was washed with EtOH (15 mL). Solvent was removed under reduced pressure and the crude product was purified using BIOTAGE chromatography (hexane/EtOAc, v/v=1/3 to 1/9) to give Compound 20 (14.3 mg, 77%). Electrospray MS [M+1]⁺ 574.3

Preparative Example 21 and 22

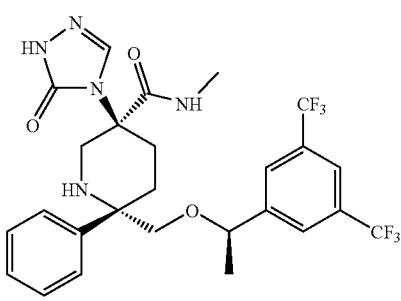

21

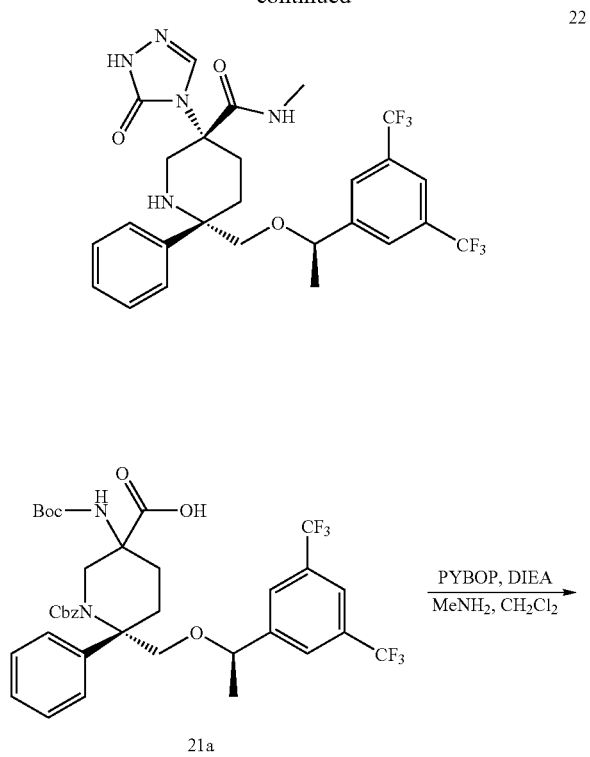

22

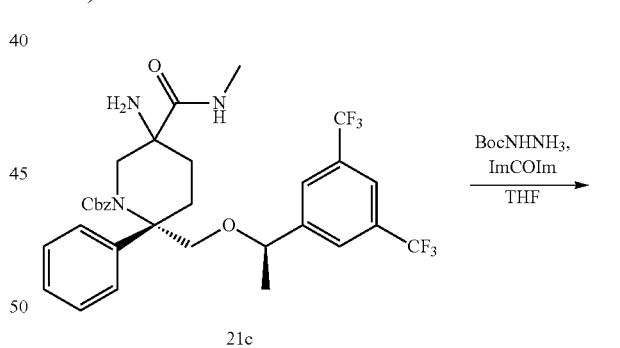

21b

TFA, CH₂Cl₂ →

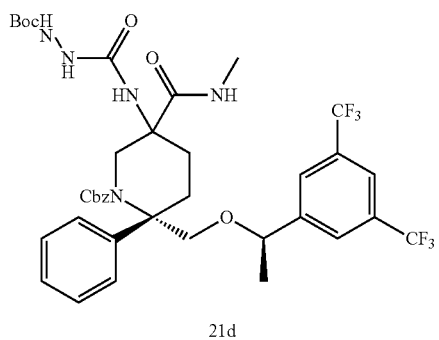

21c

Compound 21c (0.7 g, 0.95 mmol, 1.0 equiv) was dissolved in CH₂Cl₂ (10 mL) under a N₂ atmosphere. To the reaction was added excess TFA (2.0 g, 19.4 mmol, 20.0 equiv.), and the reaction mixture was stirred at room temperature overnight. The progress of the reaction was monitored by TLC (1/1 EtOAc/MeOH eluent), which indicated that some starting material was still present. Accordingly, 10.0 equiv. of TFA was added and the reaction mixture was allowed to stir for 3 h. Upon completion of the reaction, the reaction mixture was cooled to 0° C., quenched with saturated NaHCO₃, and diluted with EtOAc. The organic and aqueous layers were separated, and the organic layer was washed with brine, dried with Na₂SO₄, and concentrated to give Compound 21d (0.6 g, 99%) as a white foam.

Compound 21a (1.0 g, 1.4 mmol, 1.0 equiv) was dissolved in CH₂Cl₂ (16 mL) and the solution was cooled to 0° C. Diisopropylamine (0.54 g, 4.2 mmol, 3.0 equiv.) was added to the reaction mixture, followed by PYBOP (0.88 g, 1.7 mmol, 1.2 equiv.), and the reaction mixture was stirred at 0° C. for 5 min., then warmed to room temperature. After 20 min., excess methyl amine (7.0 mL, 14 mmol, 10.0 equiv.) was added as a 2.0M solution in THF. The flask became slightly warm, and was stirred at room temperature overnight. The progress of the reaction was monitored by TLC (95/5 EtOAc/MeOH eluent). Upon completion of the reaction, the reaction mixture was diluted with H₂O and EtOAc, the organic and aqueous layers were separated, and the organic layer was washed with brine, dried with Na₂SO₄, and concentrated to give a crude product (1.9 g) as white solid. Purification was carried out using BIOTAGE chromatography (1:1 to 2:1 EtOAc/hexane) to give Compound 21b as a white solid (0.72 g, 72%). Electrospray MS [M+1] 738.2.

Compound 21c (0.24 g, 0.38 mmol, 1.0 equiv) was dissolved in 5 mL of anhydrous THF under a nitrogen atmosphere. The solution was cooled to 0° C. In a separate round-bottomed flask was combined carbonyldiimidazole (0.15 g, 0.90 mmol, 2.4 equiv) and tert-butyl carbazate (0.1 g, 0.76 mmol, 2.0 equiv) in anhydrous THF (2 mL). The solution was allowed to stir for 30 min and added via cannula to the solution of Compound 21c over 1 min. The cannula was rinsed with anhydrous THF (1×0.8 mL). The reaction mixture was heated to reflux until the starting material was consumed. The reaction mixture was then cooled to room temperature and concentrated under vacuum to afford a colorless foam. The crude mixture was purified using BIOTAGE chromatography (2%-5% MeOH/CH₂Cl₂) to give Compound 21d (0.22 g, 74%) as a white solid.

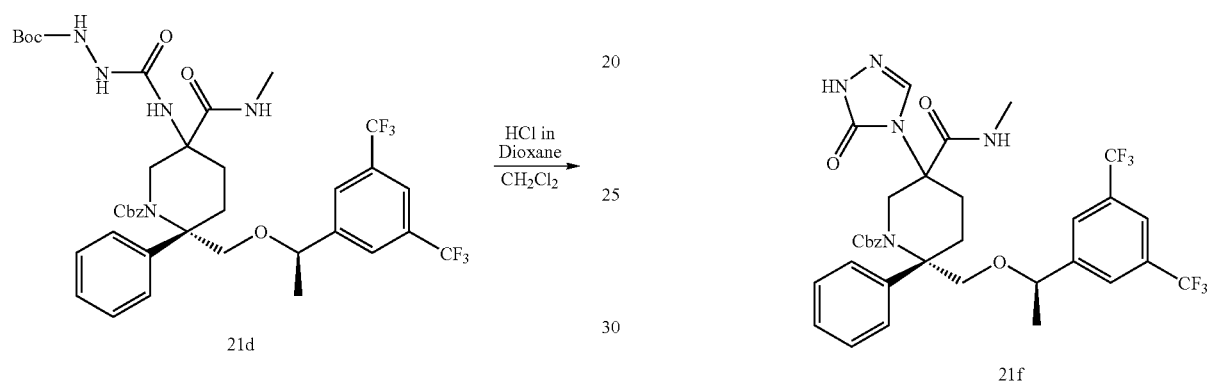

Compound 21d (0.22 g, 0.28 mmol, 1 equiv) was dissolved in 15 mL of anhydrous CH₂Cl₂ under a nitrogen atmosphere. The solution was cooled to 0° C. HCl (1.4 mL, 5.6 mmol, 20 equiv, 4 M solution in dioxane) was added and the solution was allowed to warm to room temperature and stirred overnight. The solution was cooled to 0° C. and quenched with saturated NaHCO₃ (5 mL) solution and diluted with EtOAc. The organic and aqueous layers were separated and the organic layer was washed with brine (10 mL), and dried over Na₂SO₄. The organic layer was filtered and concentrated under vacuum to give a white solid. The crude mixture was purified using BIOTAGE chromatography (5%-8% MeOH/CH₂Cl₂) to give Compound 21e (0.15 g, 79%) as a white solid.

Compound 21e (0.15 g, 0.22 mmol, 1.0 equiv) was dissolved in anhydrous DMF (1 mL). Foramidine acetate (0.126 g, 1.2 mmol, 5.5 equiv.) followed by acetic acid (0.69 mL, 1.2 mmol, 5.5 equiv.) was added, and the reaction mixture was heated to 80° C. for 30 min. Residual starting material was found by TLC analysis, and accordingly the reaction mixture was refluxed for an additional 6 h. The progress of the reaction was monitored by TLC (9/1 CH₂Cl₂/MeOH eluent). Upon completion of the reaction, the reaction mixture was cooled to room temperature, quenched with H₂O, and diluted with EtOAc. The organic and aqueous layers were separated and the organic layer was washed with brine, dried with Na₂SO₄, and concentrated to give a crude product (0.131 g) as white foam. Purification was carried out using BIOTAGE chromatography (gradient of 100% CH₂Cl₂ to (95:5) MeOH) to give Compound 21f as a white solid (0.11 g, 72%).

Electrospray MS [M+1] 706.4.

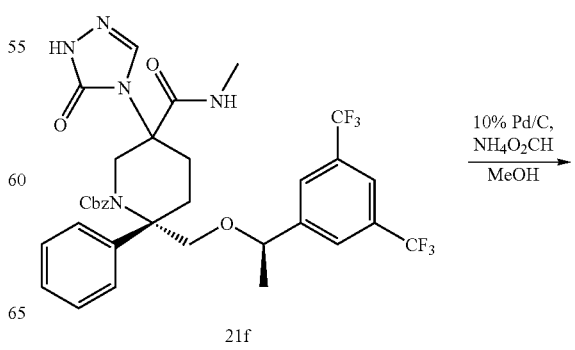

-continued

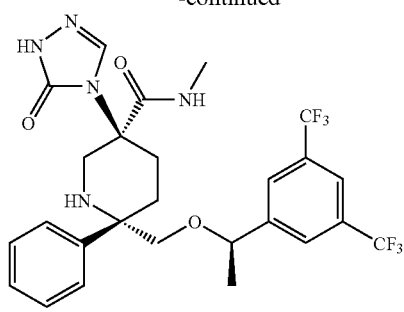

21

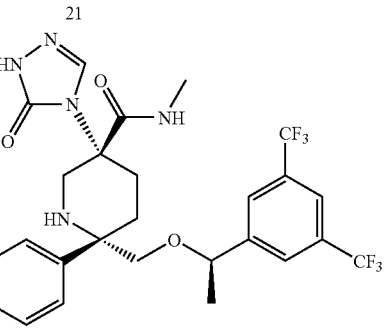

22

Compound 21f (0.02 g, 0.028 mmol, 1.0 equiv.) was dissolved in dry MeOH (1.0 mL) and was treated with 10% Pd/C (40% wt.) followed by ammonium formate (0.09 g, 0.14 mmol, 5.0 equiv.) under an inert atmosphere. The reaction mixture was heated to reflux and was monitored by TLC (9/1 CH₂Cl₂/MeOH eluent). The reaction was completed in 1 hr. The reaction mixture was filtered through CELITE, washed using EtOAc, and concentrated under vacuum. The resulting residue was taken up in EtOAc, and washed with saturated NaHCO₃, followed by brine and H₂O to give a crude product (0.019 g) as solid film. Purification was carried out by BIOTAGE chromatography (gradient of 2% to 6% MeOH/CH₂Cl₂). The de-aired product was converted to the HCl salt to give a mixture of Compounds 21 and 22 (0.014 g) as a white solid.

HRMS (FAB) calculated for $C_{26}H_{28}F_6N_3O_2$ (M+1) 572.2096. found 572.2103.

Preparative Example 23

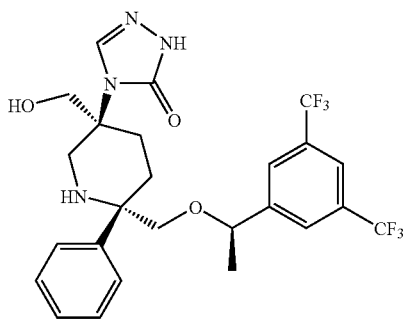

Compound 23

Step A:

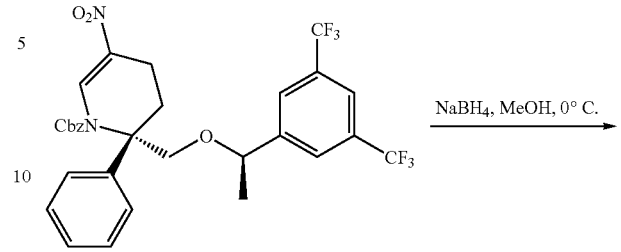

Compound 23a

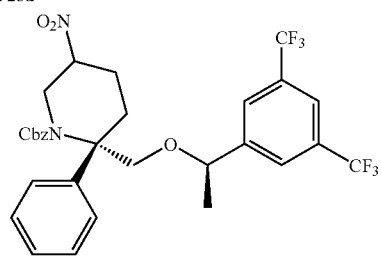

Compound 23b

NaBH₄ (2.42 g, 64.1 mmol) was added in 4 portions to a solution of Compound 23a in MeOH (160 mL) at 0° C. The reaction mixture was stirred for 4 hours and the reaction temperature was slowly increased to rt. The reaction was quenched by the slow addition of saturated aqueous NH₄Cl solution (50 mL). The reaction mixture was then diluted with EtOAc (400 mL) and neutralized with 0.5 N HCl until the aqueous phase was slightly acidic. The aqueous phase was extracted with EtOAc (3×100 mL). The combined organic layers were washed with water (100 mL), brine (100 mL), and dried over MgSO₄. After filtration and concentration, the crude product was passed through a short pad of silica gel (hexane/EtOAc, v/v=7/1). Solvent was removed under reduced pressure to give Compound 23b, 17.4 g (89%) as a light yellow syrup.

Step B:

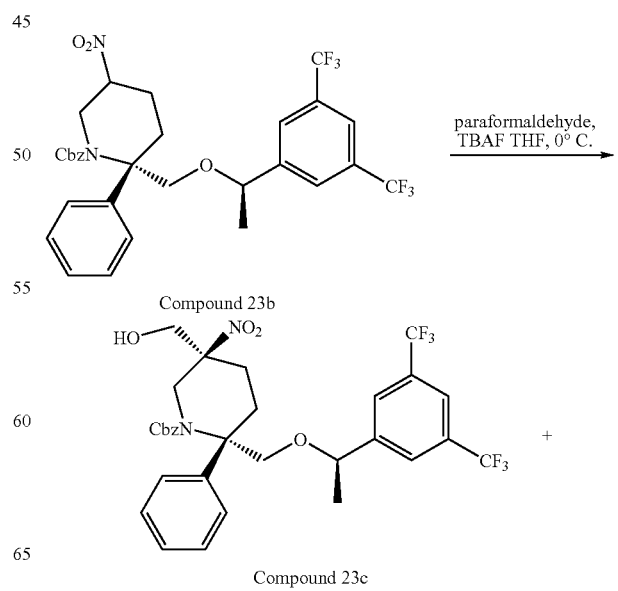

Compound 23c

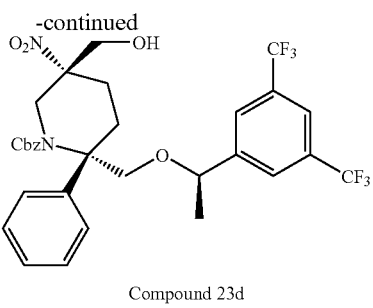

Compound 23d

TBAF (2.23 mL, 2.23 mmol, 1.0 M in THF) was added dropwise to a mixture of Compound 23b (9.1 g, 14.89 mmol) and paraformaldehyde (3.85 g) in THF (100 mL) at 0° C. The reaction mixture was stirred at 0° C. for 8 hours before it was quenched with addition of saturated aqueous NH₄Cl solution (50 mL). The reaction mixture was then diluted with EtOAc (250 mL) and the aqueous phase was extracted with EtOAc (3×50 mL). The combined organic layers were washed with water (50 mL), brine (100 mL), and dried over MgSO₄. After filtration and concentration, the crude product was purified using BIOTAGE (CH₂Cl₂/EtOAc, v/v=100/0.5) to give Compound 23c (6.0 g, 63%) and 23d (2.34 g, 24%).

Step C:

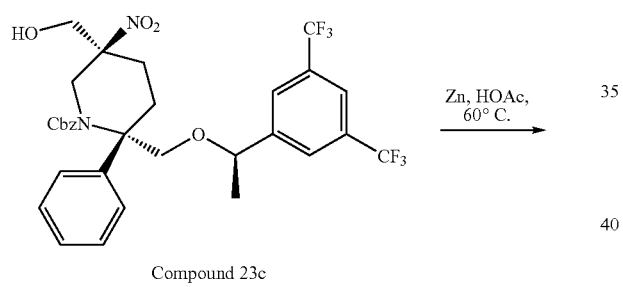

Compound 23c

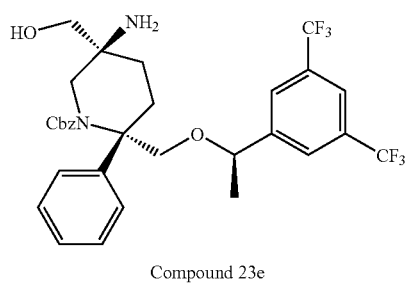

Compound 23e

A mixture of Compound 23c (7.54 g, 11.76 mmol) and Zn dust (7.68 g, 117.6 mmol) in HOAc (120 mL) was heated at 60° C. for 2 hours. The reaction mixture was cooled down and filtered through a short pad of CELITE and the residue was washed with EtOH (50 mL). Solvent was removed under reduced pressure and the residue was taken up in EtOAc (250 mL) and washed with NaOH solution (50 mL, 4.0 N). The aqueous phase was extracted with EtOAc (3×50 mL). The combined organic layers were washed with water (50 mL), brine (100 mL), and dried over MgSO₄. After filtration and concentration, the crude product was purified using BIOTAGE chromatography (hexane/EtOAc, v/v=1/3 and EtOAc/MeOH, v/v=10/1) to give Compound 23e (6.4 g, 89%).

Step D:

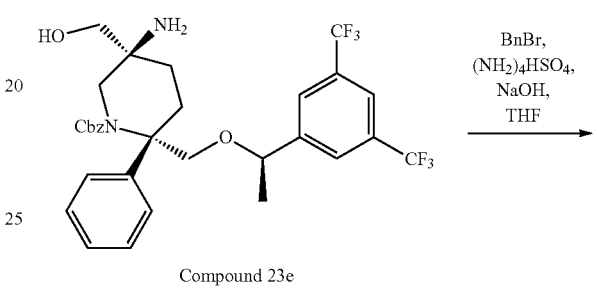

Compound 23e

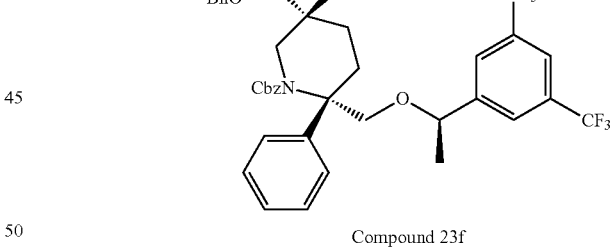

Compound 23f

BnBr (0.668 mL, 5.58 mmol) was added at rt to a vigorously stirring mixture of Compound 23e (3.1 g, 5.07 mmol) and Bu₄NHSO₄ (0.334 g, 1.014 mmol) in THF (20 mL) and aqueous NaOH solution (20 mL, 50 wt %). The reaction mixture was stirred at room temperature for 12 hours before it was diluted with EtOAc (250 mL) and washed with water (100 mL). The aqueous phase was extracted with EtOAc (3×50 mL). The combined organic layers were washed with water (50 mL), brine (100 mL), and dried over MgSO₄. After filtration and concentration, the crude product was purified using BIOTAGE chromatography (hexane/EtOAc, v/v=1/3 to 1/7) to give Compound 23f (2.8 g, 79%).

Step E:

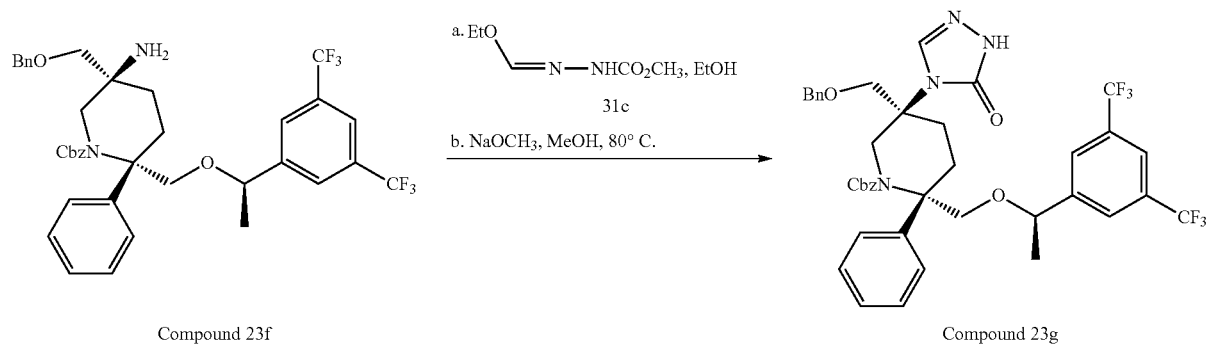

Compound 23f → Compound 23g

A solution of Compound 23f (2.72 g, 3.88 mmol) and reagent 31c (i.e., N-ethoxymethylene-hydrazine carboxylic acid methyl ester) (2.83 g, 19.4 mmol) in EtOH (15 mL) was heated at 60° C. for 18 hours. The reaction mixture was diluted with MeOH (15 mL) and then treated with NaOCH$_3$ (7.0 mL, 38.8 mmol, 30% in MeOH). The resulting reaction mixture was heated at 80° C. for 4 hours before it was cooled to room temperature. The reaction mixture was diluted with EtOAc (200 mL) and aqueous NH$_4$Cl solution (75 mL). The aqueous phase was extracted with EtOAc (3×50 mL). The combined organic layers were washed with water (50 mL), brine (100 mL), and dried over MgSO$_4$. After filtration and concentration, the crude product was purified using BIOTAGE chromatography (hexane/EtOAc, v/v=2.5/1 to 1/1) to give Compound 23g (2.54 g, 85%).

Step F:

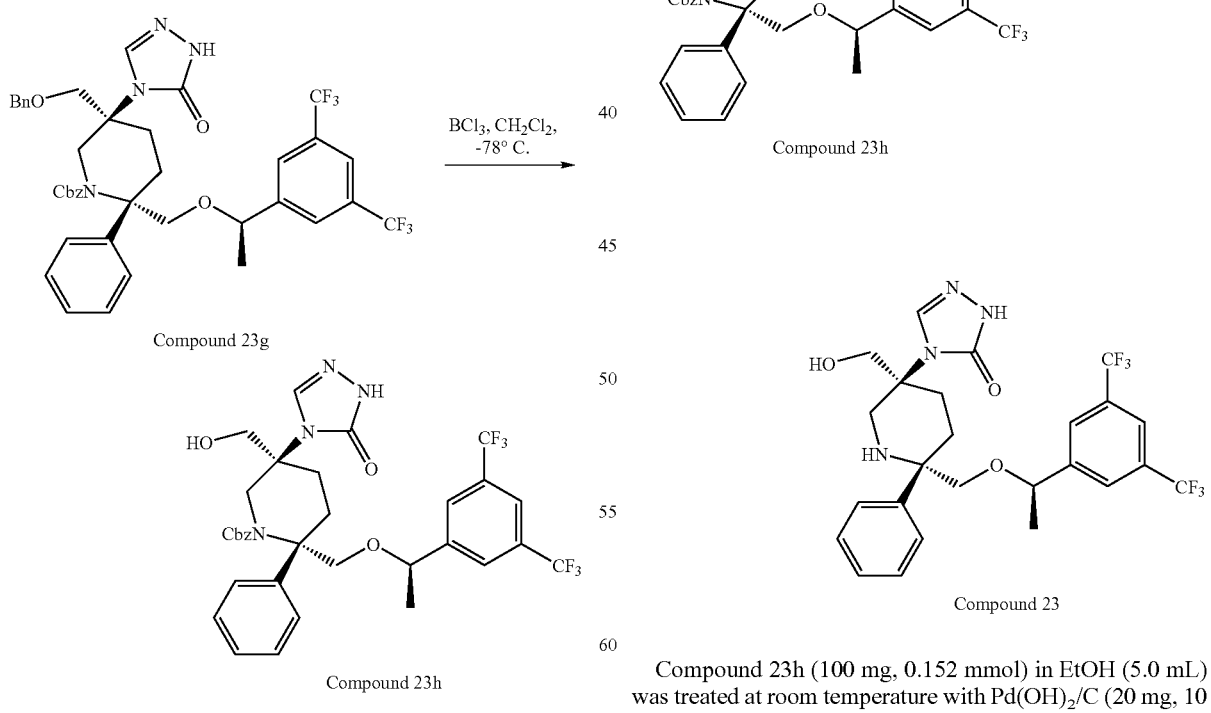

Compound 23g → Compound 23h → Compound 23

BCl$_3$ (3.26 mL, 3.26 mmol, 1.0 M in hexane) was added dropwise to a stirring solution of Compound 23g (0.502 g, 0.653 mmol) in CH$_2$Cl$_2$ (45 mL) at −78° C. The reaction was quenched in 1 hour by the addition of aqueous NaHCO$_3$ solution (50 mL) at −78° C. The mixture was diluted with EtOAc (100 mL) and vigorously stirred at room temperature for 2 hours. The aqueous phase was extracted with EtOAc (3×30 mL). The combined organic layers were washed with water (50 mL), brine (50 mL), and dried over MgSO$_4$. After filtration and concentration, the crude product was purified using BIOTAGE chromatography (hexane/EtOAc, v/v=1/3 to 1/9) to give Compound 23h (0.39 g, 91%).

Step G:

Compound 23h (100 mg, 0.152 mmol) in EtOH (5.0 mL) was treated at room temperature with Pd(OH)$_2$/C (20 mg, 10 wt %) and was hydrogenated using a H$_2$ balloon for 30 minutes. The reaction mixture was filtered through a short pad of CELITE and the residue was washed with EtOH (15 mL). Solvent was removed under reduced pressure and the crude product was purified using BIOTAGE chromatography (hexane/EtOAc, v/v=1/7) to give Compound 23 (68 mg, 82%). Electrospray MS [M+1]+ 545.1.

Preparative Example 24

Example 24

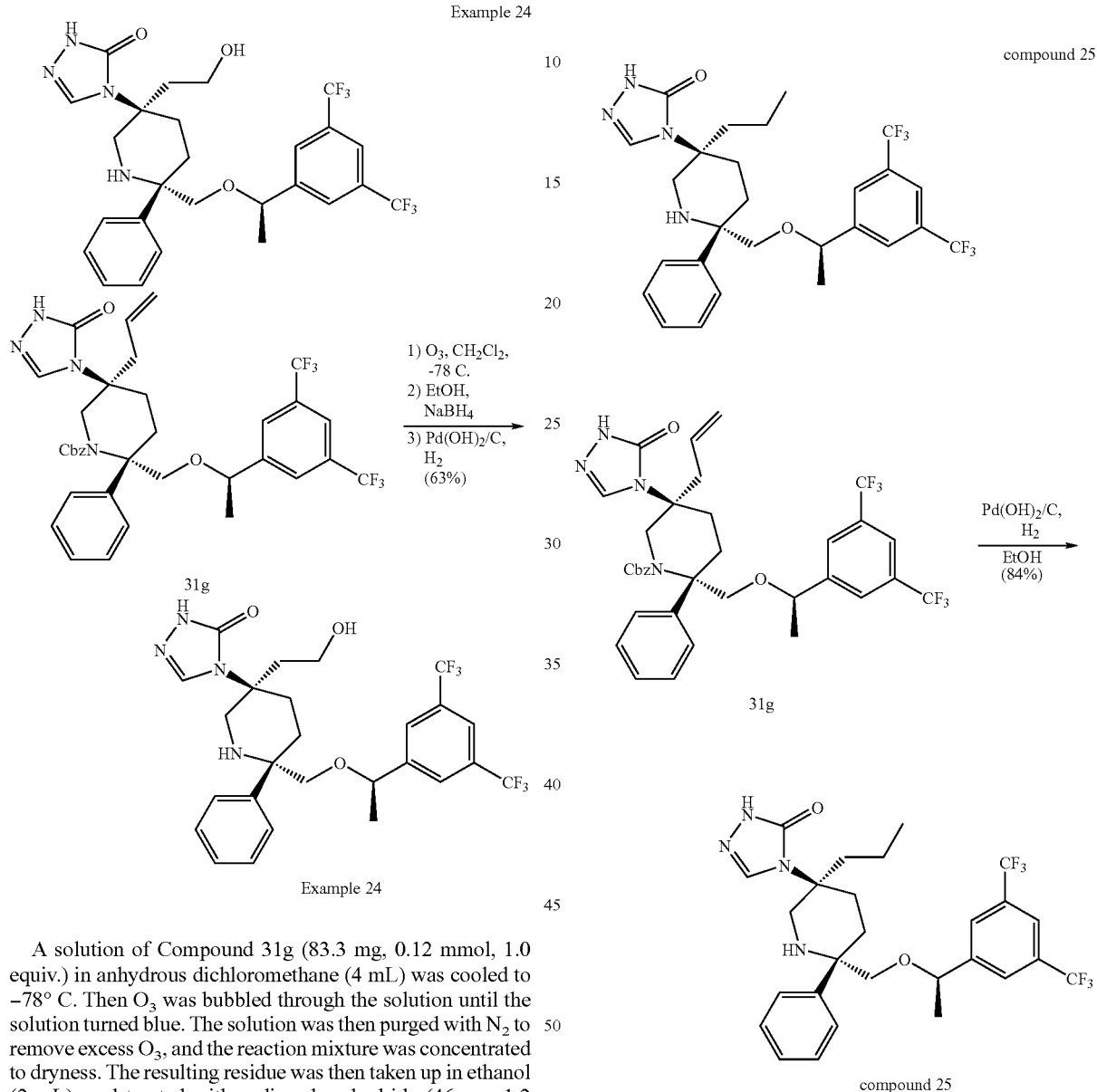

Example 24

A solution of Compound 31g (83.3 mg, 0.12 mmol, 1.0 equiv.) in anhydrous dichloromethane (4 mL) was cooled to −78° C. Then O$_3$ was bubbled through the solution until the solution turned blue. The solution was then purged with N$_2$ to remove excess O$_3$, and the reaction mixture was concentrated to dryness. The resulting residue was then taken up in ethanol (2 mL), and treated with sodium borohydride (46 mg, 1.2 mmol, 10 equiv.). The reaction mixture was stirred at room temperature until TLC (50% EtOAc/hexanes) showed that the starting material was completely consumed. The reaction mixture was then concentrated to dryness. The residue was dissolved in absolute ethanol (4 mL) and treated with Pd (OH)$_2$/C (80 mg, 20 wt %, 0.11 mmol, 0.88 equiv.) before hydrogenating with a hydrogen balloon. The reaction mixture was stirred at room temperature until TLC (5% MeOH/ CH$_2$Cl$_2$) showed that the starting material was completely consumed. The reaction mixture was again concentrated to dryness. The residue was taken up into ethyl acetate, washed with saturated sodium bicarbonate aqueous solution, and the aqueous and organic layers separated. The aqueous layer was further extracted with ethyl acetate. The combined organic layers were dried over anhydrous Na$_2$SO$_4$, filtered, concentrated to give the crude product, which was purified using Prep-TLC (MeOH/CH$_2$Cl$_2$=5%) to give pure Compound 24 (42 mg, yield 63%). MS [M+1]+ 559.1.

Preparative Example 25 compound 25

31g compound 25

To a solution of Compound 31g (83.3 mg, 0.12 mmol, 1.0 equiv.) in absolute ethanol (3 mL) was added Pd(OH)$_2$/C (20 mg, 20 wt %, 0.028 mmol, 0.88 equiv.) before hydrogenating with a hydrogen balloon. The reaction mixture was stirred at room temperature until TLC (50% EtOAc/hexanes) showed that starting material was completely consumed. The reaction mixture was then concentrated to dryness. The resulting residue was taken up into ethyl acetate, washed with saturated sodium bicarbonate aqueous solution, and the aqueous and organic layers were separated. The aqueous layer was further extracted with ethyl acetate. The combined organic layers were dried over anhydrous Na$_2$SO$_4$, filtered, and concentrated to give the crude product, which was purified using Prep-TLC (50% EtOAc/hexanes) to give pure Compound 25 (15 mg, yield 84%). MS [M+1]+ 557.1.

Preparative Example 26

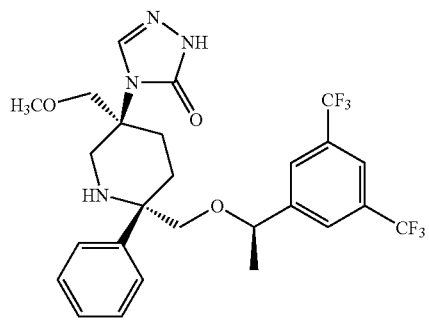

Compound 26

Step A:

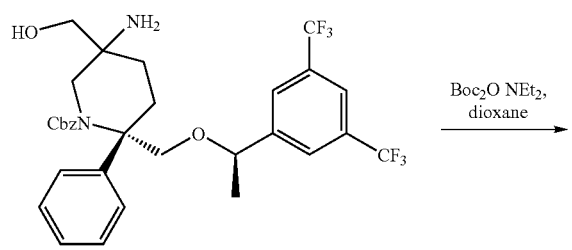

Compound 26a

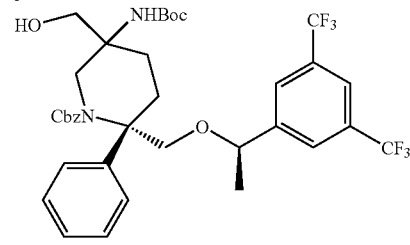

Compound 26b

Et₃N (0.129 mL, 0.93 mmol) was added to a solution of Compound 26a (0.472 g, 0.77 mmol) and Boc₂O (0.168 g, 0.77 mmol) in dioxane (3.0 mL) at room temperature. The resulting solution was stirred for 8 hours before it was diluted with EtOAc (50 mL). The organic phase was washed with 0.5 N HCl (10 mL). The aqueous phase was extracted with EtOAc (3×15 mL). The combined organic layers were washed with water (15 mL), brine (15 mL), and dried over MgSO₄. After filtration and concentration, the crude product was purified using BIOTAGE chromatography (hexane/EtOAc, v/v=1/1) to give Compound 26b (0.465 g, 85%).

Step B:

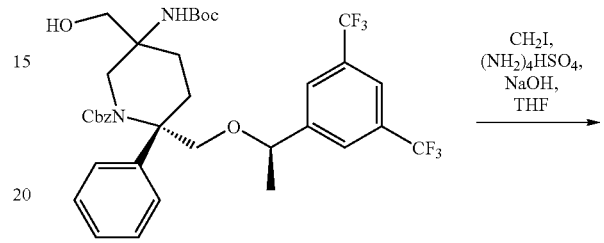

Compound 26b

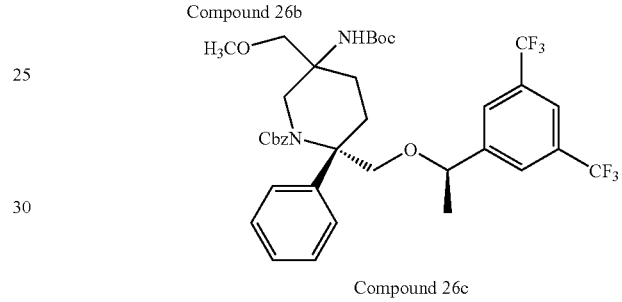

Compound 26c

CH₃I (0.372 mL, 5.98 mmol) was added at rt to a vigorously stirring mixture of Compound 26b (0.425 g, 0.598 mmol) and Bu₄NHSO₄ (40.6 mg, 0.12 mmol) in THF (5.0 mL) and aqueous NaOH solution (5.0 mL, 50 wt %). The reaction mixture was stirred at room temperature for 12 hours before it was diluted with EtOAc (50 mL) and washed with water (15 mL). The aqueous phase was extracted with EtOAc (3×15 mL). The combined organic layers were washed with water (15 mL), brine (15 mL), and dried over MgSO₄. After filtration and concentration, the crude product was purified using BIOTAGE chromatography (hexane/EtOAc, v/v=5/1) to give Compound 26c (0.345 g, 80%).

Step C:

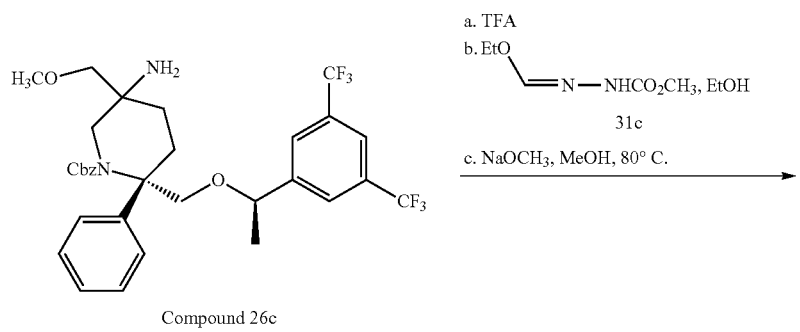

Compound 26c

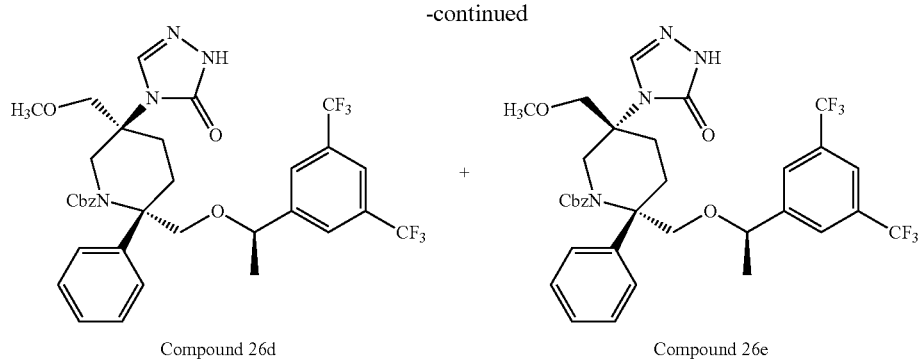

Compound 26d        +        Compound 26e

A solution of Compound 26c (0.345 g, 0.476 mmol) in TFA (3.0 mL) was stirred at room temperature for 20 minutes before the solvent was removed under reduced pressure. The residue was taken up in EtOAc (50 mL) and washed with NaOH solution (4.0 N, 15 mL). The aqueous phase was extracted with EtOAc (3×10 mL). The combined organic layers were washed with water (15 mL), brine (15 mL), and dried over MgSO$_4$. After filtration and concentration, the crude amine (0.29 g, 0.464 mmol) was dissolved in EtOH (3.0 mL) and treated with reagent 31c (0.4.6 g, 2.78 mmol). The resulting solution was heated at 60° C. for 18 hours. The reaction mixture was diluted with MeOH (3.0 mL) and then treated with NaOCH$_3$ (0.672 mL, 3.712 mmol, 30% in MeOH). The resulting reaction mixture was heated at 80° C. for 4 hours before it was cooled to room temperature. The system was diluted with addition of EtOAc (50 mL) and aqueous NH$_4$Cl solution (15 mL). The aqueous phase was extracted with EtOAc (3×15 mL). The combined organic layers were washed with water (15 mL), brine (15 mL), and dried over MgSO$_4$. After filtration and concentration, the crude product was purified using BIOTAGE chromatography (hexane/EtOAc, v/v=1/3) to give a mixture of Compounds 26d and 26e (0.275 g, 83% for 3 steps) which were separated with OD chiral HPLC (hexane/isopropanol v/v=95/5) to give pure Compounds 26d and 26e.

Step D:

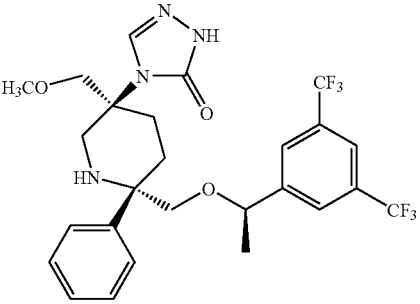

Compound 26

Compound 26d (38 mg, 0.0548 mmol) in EtOH (3.0 mL) was treated at room temperature with Pd(OH)$_2$/C (7.6 mg, 10 wt %) and was hydrogenated using a H$_2$ balloon for 30 minutes. The reaction solution was filtered through a short pad of CELITE and the residue was washed with EtOH (15 mL). Solvent was removed under reduced pressure and the crude product was purified using BIOTAGE chromatography (hexane/EtOAc, v/v=1/4) to give Compound 26 (25 mg, 82%). Electrospray MS [M+1]$^+$ 559.1.

Preparative Example 27

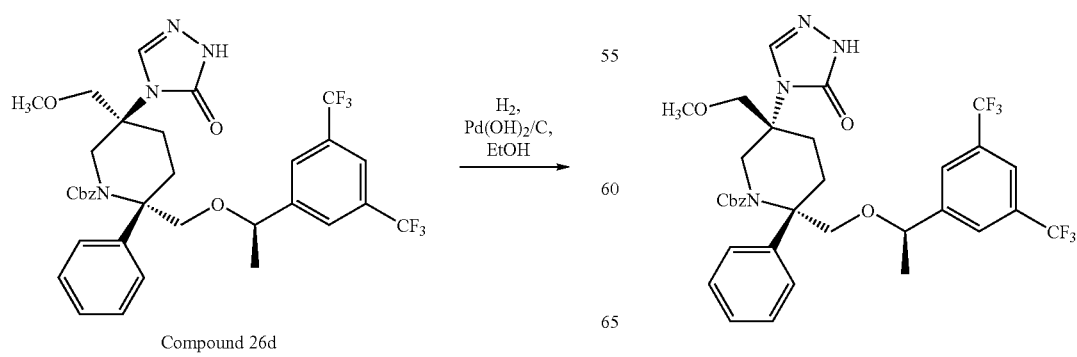

Compound 26d       →       Compound 27

Step A:

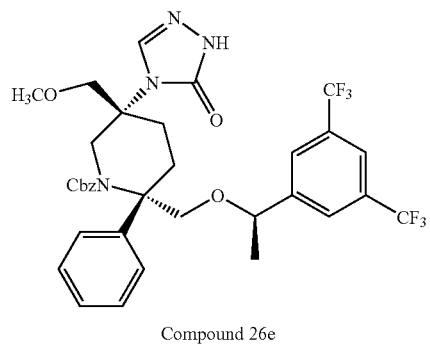

Compound 26e

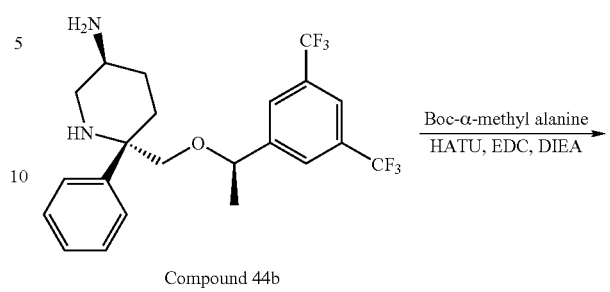

Compound 44b

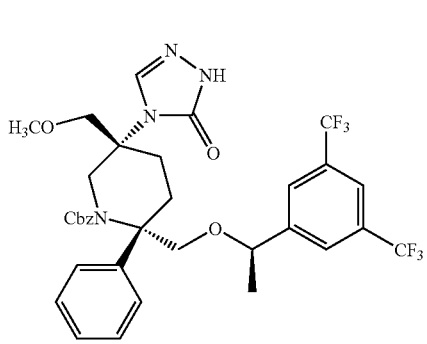

Compound 27

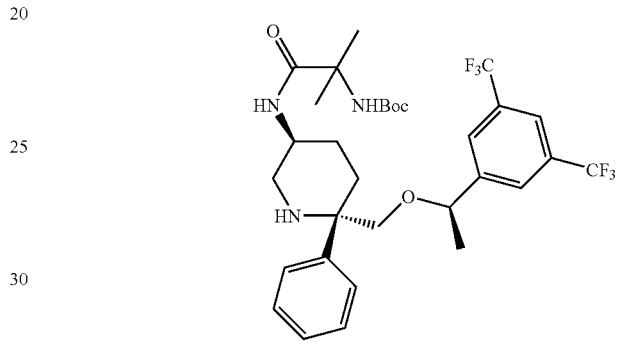

Compound 28a

Compound 26e (41 mg, 0.0592 mmol) in EtOH (3.0 mL) was treated at room temperature with Pd(OH)$_2$/C (8.2 mg, 10 wt %) and was hydrogenated using a H$_2$ balloon for 30 minutes. The reaction solution was filtered through a short pad of CELITE and the residue was washed with EtOH (15 mL). Solvent was removed under reduced pressure and the crude product was purified using BIOTAGE chromatography (hexane/EtOAc, v/v=1/4) to give Compound 27 (26 mg, 79%). Electrospray MS [M+1]$^+$ 559.1.

Preparative Example 28

Compound 28

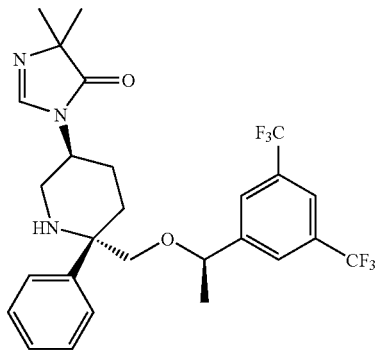

In a 25 mL round-bottomed flask, Compound 44b (0.2 g, 0.45 mmol, 1.0 equiv) was dissolved in DMF (5.0 mL). HATU (0.342 g, 0.90 mmol, 2.0 equiv), EDC (0.172 g, 0.90 mmol, 2.0 equiv), and DIEA (0.118 mL, 0.68 mmol, 1.5 equiv) were added. The reaction mixture was cooled to 0° C. and Boc-α-methyl alanine (0.109 g, 0.54 mmol, 1.2 equiv) was added. The reaction mixture was allowed to stir overnight. The reaction mixture was then quenched with saturated NaHCO$_3$ (5 mL), diluted with EtOAc (10 mL), and extracted with EtOAc (2×5 mL). The organic layer was washed with brine (10 mL), dried over MgSO$_4$, and concentrated. The resulting residue was purified by preparative TLC (9/1 hexanes/EtOAc) to give 0.12 g (43%) of Compound 28a.

Step B:

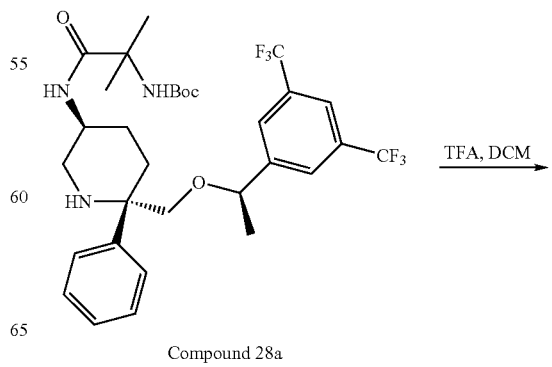

Compound 28a

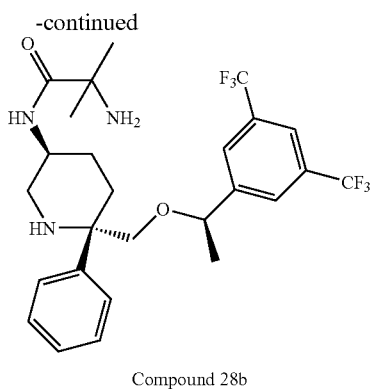

Compound 28b

Compound 28b was prepared by a method similar to that the compound 45c, described below, in which a DCM solution of Compound 28a was reacted with TFA to remove the Boc protecting group.

Step C:

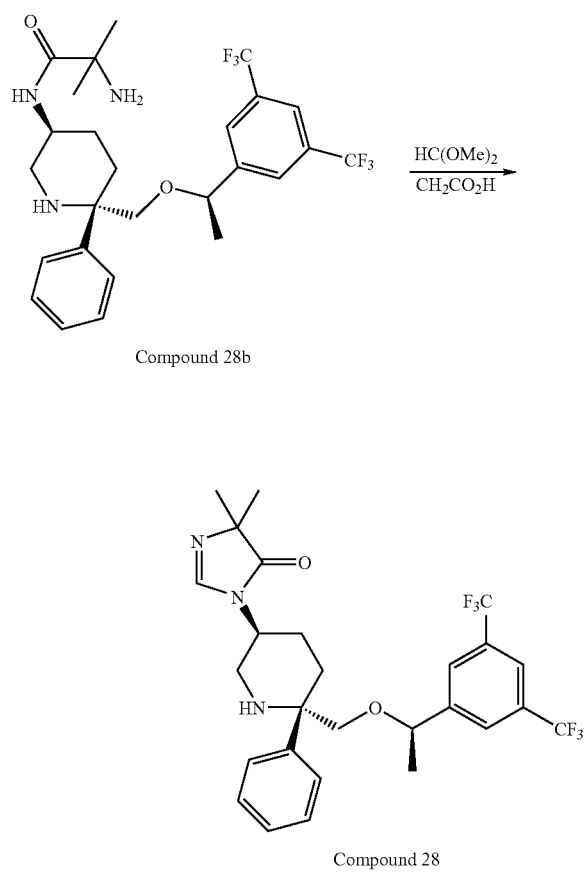

Compound 28b

Compound 28

In a 10 mL round-bottomed flask, compound 28b (0.050 g, 0.094 mmol, 1.0 equiv) was dissolved in toluene (1 mL), and then trimethylorthoformate (0.012 mL, 0.113 mmol, 1.2 equiv) and 1 drop of acetic acid were added. The solution was heated at 60° C. The reaction mixture was allowed to stir for over 48 hours. The reaction mixture was then taken up in EtOAc (5 mL) and washed with saturated NaHCO$_3$ (5 mL). The organic layer was washed with brine (5 mL), dried over MgSO$_4$, and concentrated. The crude product was purified by preparative TLC (EtOAc) to yield 0.010 g of Compound 28. HRMS calculated for C$_{27}$H$_{29}$F$_6$N$_3$O$_2$ (M+H) 542.2242. found 542.2222.

Preparative Example 29

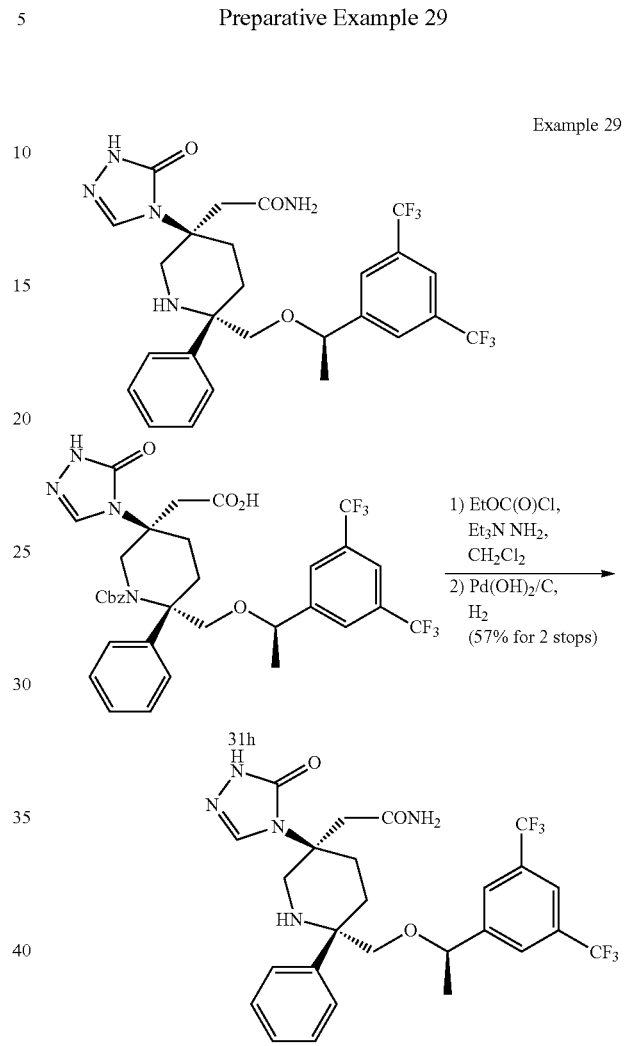

Example 29

Example 29

A solution of Compound 31h (39 mg, 0.055 mmol, 1.0 equiv.) in anhydrous dichloromethane (1 mL) was cooled to −20° C. Then triethylamine (10 mL, 0.069 mmol, 1.25 equiv.) and ethyl chloroformate (6.5 mL, 0.066 mmol, 1.2 equiv.) were added. The resulting pale green solution was stirred at −15° C. for 30 minutes. Ammonia gas was bubbled through the solution for 20 minutes. TLC (EtOAc) indicated that the reaction was complete. The reaction mixture was diluted with ethyl acetate, washed sequentially with 1N HCl (1 mL), saturated sodium carbonate aqueous solution, and brine. The organic layer was dried over Na$_2$SO$_4$, filtered, and concentrated. The resulting residue was dissolved in absolute ethanol (6 mL), to which was added Pd(OH)$_2$/C (17 mg, 20 wt %, 0.024 mmol, 0.43 equiv.) before attaching a hydrogen balloon to the reaction flask. The reaction mixture was stirred at room temperature until TLC (5% MeOH/EtOAc) showed that the starting material was completely consumed. The reaction mixture was concentrated to dryness, and the residue was taken up into ethyl acetate, washed with saturated sodium bicarbonate aqueous solution, and the organic and aqueous layers were separated. The aqueous layer was further extracted with ethyl acetate. The combined organic layers were dried over anhydrous Na₂SO₄, filtered, and concentrated to give the crude product, which was purified using Prep-TLC (5% MeOH/EtOAc) to give pure Example 29 (18 mg, yield 57%). MS [M+1]⁺ 572.1.

Preparative Example 30 compound 30

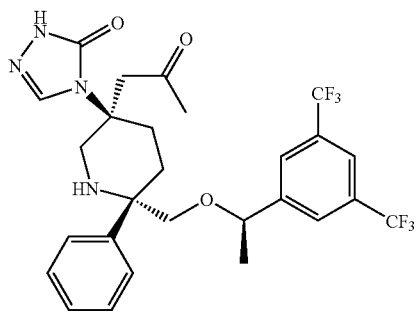

Step 1:

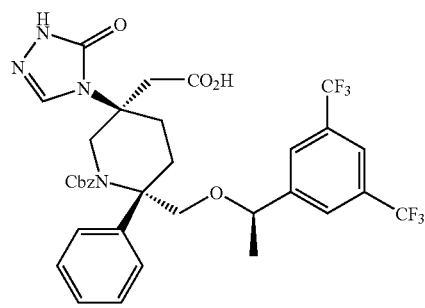

31h

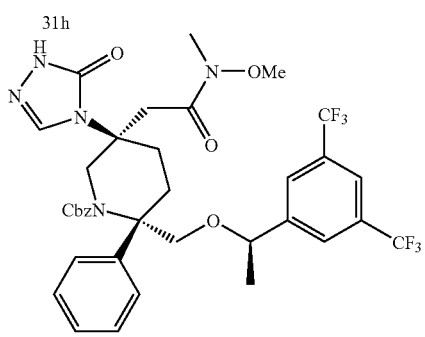

30a

To a solution of Compound 31h (450 mg, 0.64 mmol, 1.0 equiv.) in anhydrous DMF (3.5 mL), was added, sequentially, HATU (290.5 mg, 0.764 mmol, 1.2 equiv.), N,N-dimethylamine hydrochloride salt (99 mg, 1.01 mmol, 1.6 equiv.) and diisopropyl ethylamine (0.50 μL, 2.87 mmol, 4.5 equiv.). The resulting orange solution was stirred at room temperature until TLC (5% MeOH/EtOAc) showed that starting material was completely consumed. The reaction mixture was poured into dichloromethane (200 mL), washed sequentially with half-saturated citric acid aqueous solution, saturated NaHCO₃, and brine. The organic layer was dried over anhydrous Na₂SO₄, filtered, and concentrated to give the crude product, which was purified using BIOTAGE chromatography (EtOAc/Hexane=3:1) to give Compound 30a as a brown solid (208 mg, yield 43.6%).

Step 2:

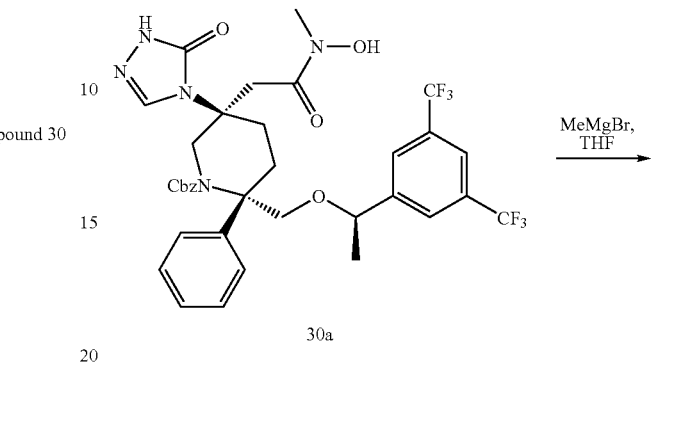

30a

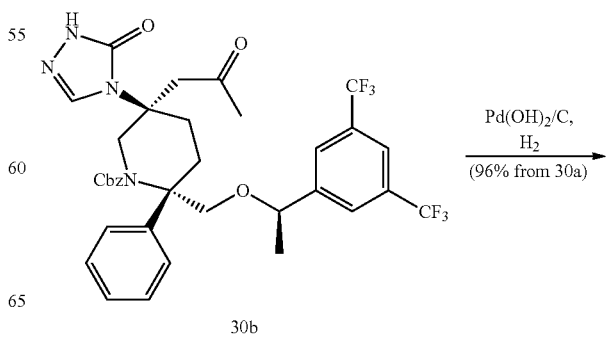

30b

Methylmagnesium bromide (1.65 mL, 1.0 M in t-butylether, 1.65 mmol, 6.0 equiv.) was added dropwise to a solution of Compound 30a (206 mg, 0.275 mmol, 1.0 equiv.) in anhydrous THF (3 mL). TLC (EtOAc) showed that the starting material was totally gone after the reaction mixture was stirred at room temperature for 30 minutes. The reaction mixture was then diluted with ethyl acetate, quenched with a saturated aqueous NH₄Cl solution, and extracted with EtOAc. The combined organic layers were dried over Na₂SO₄, filtered and concentrated to give the crude product, Compound 30b. Compound 30b was used in the next step without purification.

Step 3:

-continued

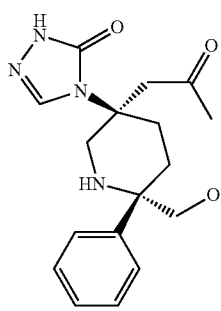

30

Using the same procedure as that of Example 31, Step 6, the crude Compound 30b was hydrogenated to give pure Example 30 (150 mg, yield 95.6% from Compound 30a). MS [M+1]$^+$ 571.1.

Preparative Example 31

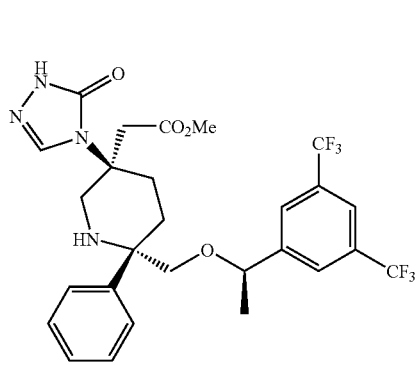

31

Step 1:

H$_2$NNHC(O)OCH$_3$ + (EtO)$_3$CH $\xrightarrow[(>55\%)]{88° C.}$ 31a      31b

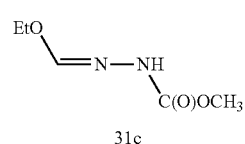

31c

Compound 31b (32 mL) was added to a solution of Compound 31a (1.0 g, 11.1 mmol, 1.0 equiv.) in triethylorthoformate. The solution was heated at 88° C. for 36 hours, and then concentrated to dryness under vacuum. The resulting residue was recrystallized from EtOAc, to give Compound 31c (0.94 g, yield 58%).

Step 2:

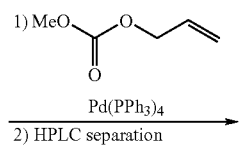

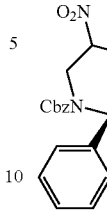

23b

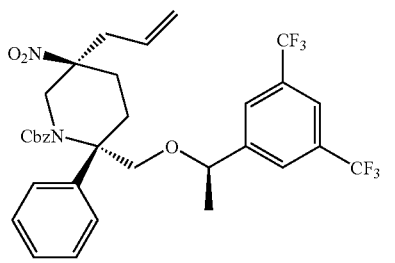

31d

+

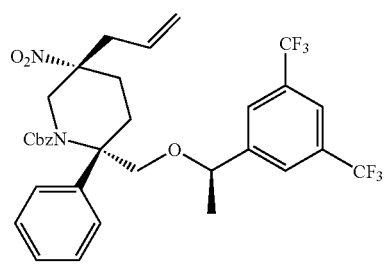

31e

To a solution of Compound 23b (2.5 g, 4.1 mmol) in THF (20 mL) was added allylmethylcarbonate (0.465 ml, 8.2 mmol), and Pd(PPh$_3$)$_4$ (236 mg, 0.205 mmol). The reaction vessel was purged three times with nitrogen, and then the solution was allowed to stir for 16 hours. The solvent was then removed and the residue was filtered through a short silica column using 20% EtOAC/hexanes as eluent. The filtrate was concentrated and Compounds 31d and 31e were separated using prep-HPLC. MS [M+1]$^+$ 651.1 for both compounds.

Step 3:

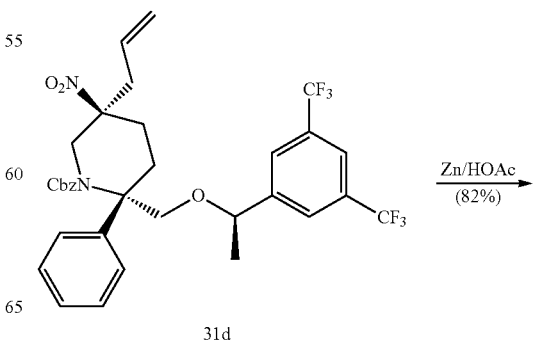

31d

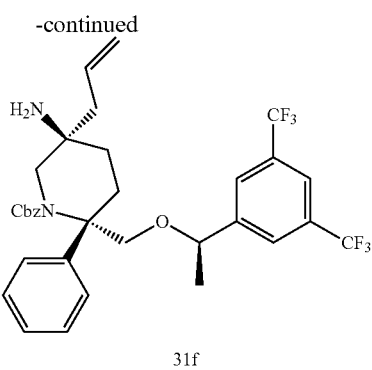

31f

A round-bottomed flask was charged with Compound 31d (3.84 g, 5.90 mmol, 1.0 equiv.) and glacial acetic acid (20 mL). To the resulting yellowish solution at 0° C. was added as several small portions of Zinc dust (3.86 g, 59.0 mmol, 10 equiv.). The reaction mixture was stirred at room temperature for 6 hours until TLC (30% EtOAc/hexane) showed that the starting material Compound 31d was totally consumed. The reaction mixture was then diluted with ethyl acetate, and passed through a CELITE pad in a funnel. The CELITE pad was thoroughly washed with ethyl acetate, and the combined with the filtrate. The filtrate was concentrated to provide a crude product, which was purified using BIOTAGE chromatography (30% EtOAc/hexanes) to give a pure colorless oil product, Compound 31f (3 g, yield 81.9%).

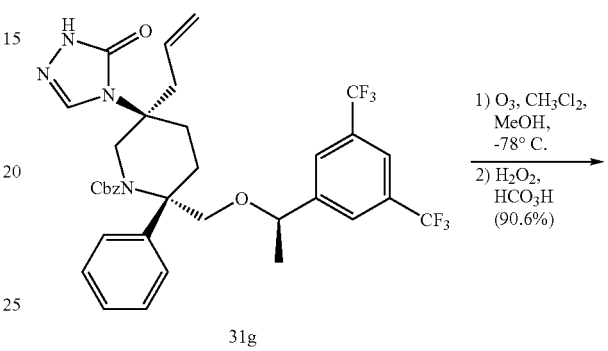

31f

To a solution of Compound 31f (33.4 mg, 0.054 mmol, 1.0 equiv.) in ethanol (0.4 mL) was treated with reagent 31c (67.5 mg, 0.46 mmol, 5 equiv.) and stirred at room temperature overnight. It was then diluted with anhydrous methanol (1 mL) and treated with sodium methoxide, then heated at 88° C. until TLC (EtOAc) showed only product. It was concentrated to dryness, and then taken up into ethyl acetate, washed with saturated sodium bicarbonate solution and the layers were separated. The aqueous layer was further extracted with ethyl acetate. The combined organic layer was dried over anhydrous $Na_2SO_4$, filtered, and concentrated to get the crude product, which was purified via BIOTAGE chromatography (25-40% EtOAC/hexanes) to get pure compound 31g (22.4 mg, yield >60%).

Step 4:

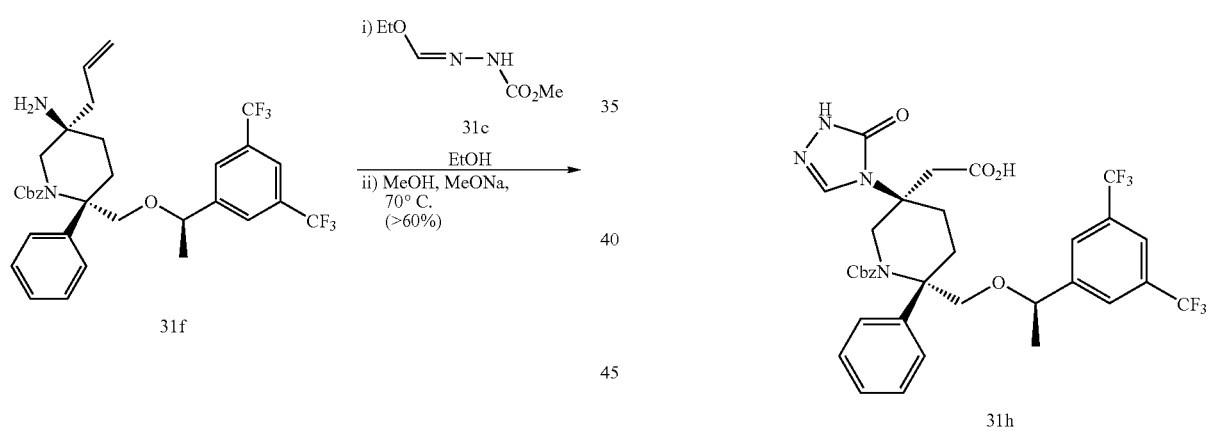

31g

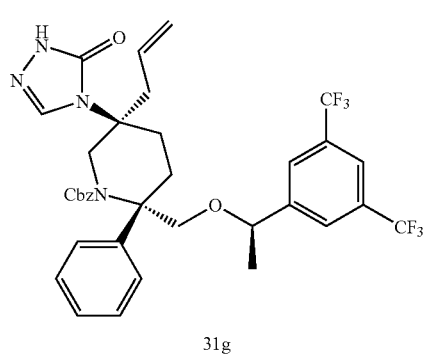

31h

Compound 31g (306 mg, 0.44 mmol, 1.0 equiv.) was dissolved in anhydrous dichloromethane (5 mL). The resulting colorless solution was cooled to −78° C., then $O_3$ was bubbled through until the solution turned purple. The solution was then purged with $N_2$ to remove excess $O_3$. The solution was then concentrated to dryness. The resulting white foam was dissolved in formic acid (1.5 mL) and treated with hydrogen peroxide (1.5 mL, 30% aqueous solution) to form a white suspension, which was heated to 80° C. overnight. LCMS analysis showed only the product peak. The solvent was removed under vacuum, and the residue was dissolved in ethyl acetate and washed with half saturated $Na_2S_2O_3$ aqueous solution. The resulting two layers were separated, and the aqueous layer was further extracted with ethyl acetate. The combined organic layers were dried over anhydrous $Na_2SO_4$, filtered and concentrated to give the Compound 31h (284.2 mg, yield 90.6%). Compound 31h was used in the next step without purification.

Step 5:

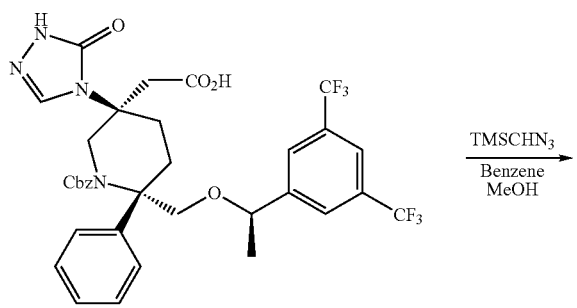

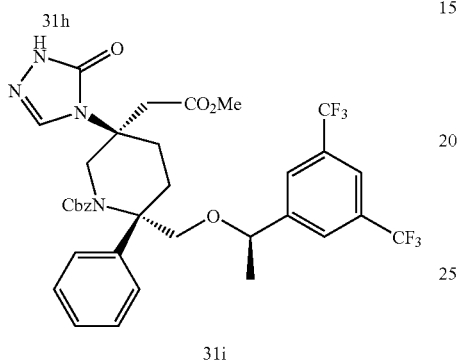

31i

To a solution of Compound 31h (104 mg, 0.147 mmol, 1.0 equiv.) in benzene (4 mL) and methanol (1 mL), was added dropwise a 2.0M solution of trimethylsilyl diazomethane in hexanes (88 μL, 0.177 mmol, 1.2 equiv.). TLC (10% MeOH/CH$_2$Cl$_2$) showed that the starting material was gone completely after stirring the reaction mixture at room temperature for 30 minutes. The solvent was removed to give the crude product, which was used in the next step without purification.

Step 6:

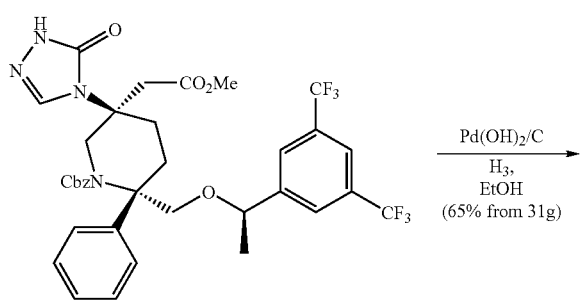

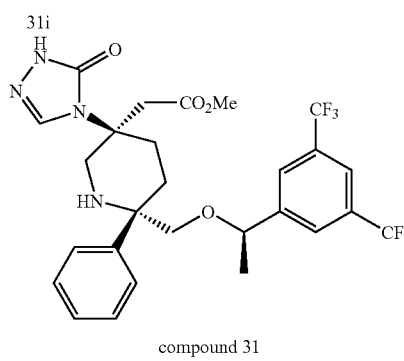

compound 31

The crude product from Step 5, Compound 31i, was dissolved in absolute ethanol (4.5 mL). To this solution was added Pd(OH)$_2$/C (46.7 mg, 20 wt %, 0.067 mmol, 0.45 equiv.), and then the reaction mixture was hydrogenated with a hydrogen balloon. The hydrogenation reaction was stopped when TLC (10% MeOH/CH$_2$Cl$_2$) showed that the starting material was consumed. The diluted reaction mixture was carefully passed through a CELITE packed funnel, and the CELITE pad was washed thoroughly with methanol. The filtrate was concentrated to dryness. The resulting residue was purified by prep-TLC (10% MeOH/CH$_2$Cl$_2$) to give the pure Compound 31 (56.2 mg, yield 65% from Compound 31g), MS [M+1]$^+$ 587.1.

Preparative Example 32

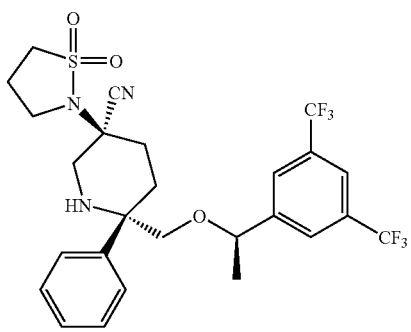

32

Step 1:

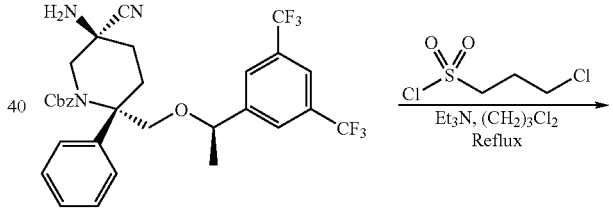

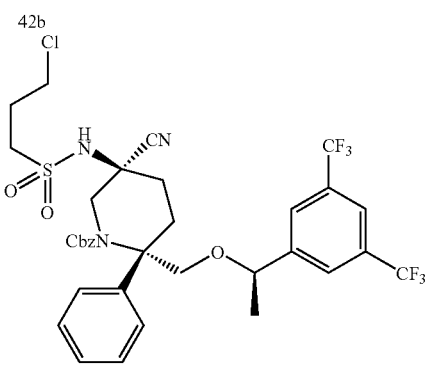

32a

In a 25 ml round-bottomed flask, Compound 42b (0.142 g, 0.23 mmol, 1.0 equiv) was taken up in 3 mL of dichloroethane under a N$_2$ atmosphere and the reaction mixture was treated with Et$_3$N (0.0.48 ml, 0.34 mmol, 1.5 equiv) followed by 3-chlorosulfonyl propyl chloride (0.037 ml, 0.3 mmol, 1.2 equiv). The reaction mixture was stirred at room temperature overnight. The progress of the reaction was monitored by TLC (60:40 EtOAc/hexane) and MS, which indicated no desired product was formed. Accordingly, the reaction mixture was then heated to reflux. After one hour of heating the reaction was complete. The reaction mixture was then cooled and diluted with $CH_2Cl_2$, and quenched with 1N HCl. The organic layer was dried over $Na_2SO_4$ and concentrated to give crude Compound 32a (0.11 g), which was used in the next step without further purification.

Step 2:

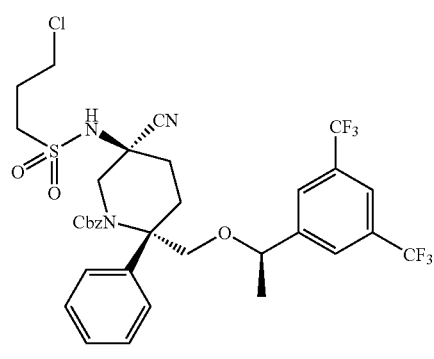

32a

DBU, DMF

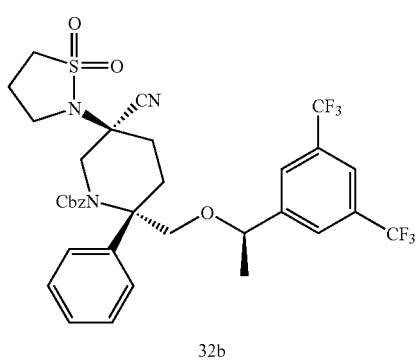

32b

Step 3:

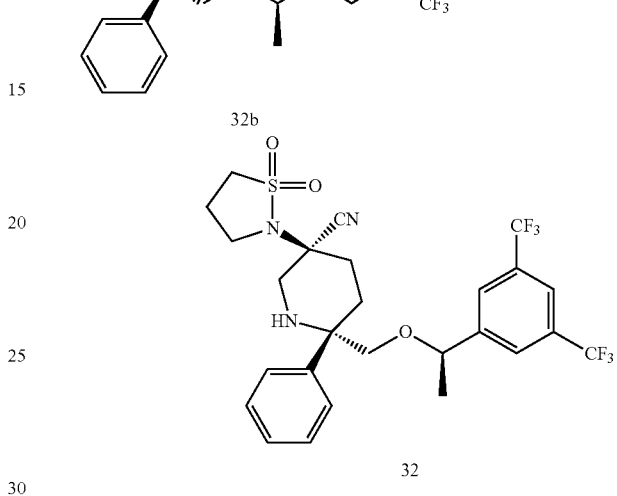

32b

20% PdOH, MeOH, $H_2$(g)

32

Compound 32b (0.072 g, 0.1 mmol, 1.0 equiv) was dissolved in dry MeOH (1.5 ml) and was treated with 20% $Pd(OH)_2$ (60% wt.) under an inert atmosphere. The reaction was hydrogenated at atmospheric pressure and the progress of the reaction was monitored by TLC (40:60 EtOAc/hexane). The reaction was completed in 45 min, and was filtered through CELITE, washed with EtOAc, and concentrated to give a crude product. The crude product was purified using preparative chromatography (60/40 EtOAc/hexane) to give Compound 32 (0.04 g, 70%).

Electrospray MS [M+1] 576.2.

HRMS (FAB) calculated for $C_{26}H_{28}F_6N_3O_2$ (M+1) 576.1756. found 576.1764.

Preparative Example 33

In a flame dried 15 ml round-bottomed flask, Compound 32a (0.11 g, 0.23 mmol, 1.0 equiv) was taken up in dry DMF. To this reaction mixture, 1,8-diazabicyclo[5.4.0]undec-7ene (0.044 g, 0.29 mmol, 1.2 equiv) was added and the reaction mixture was stirred at room temperature overnight. The progress of the reaction was monitored by TLC (30:70 EtOAc/hexane) and MS. Upon completion of the reaction, the reaction mixture was diluted with EtOAc and quenched with $H_2O$. The organic layer was dried over $Na_2SO_4$ and concentrated to give crude Compound 32b (0.1 g). Purification was carried out using BIOTAGE chromatography (30/70 EtOAc/hexane) to give purified Compound 32b (0.072 g).

Electrospray MS [M+1] 710.2.

Example 33

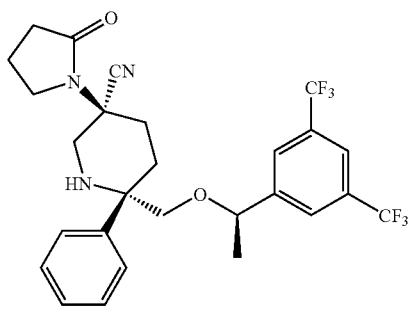

Step 1:

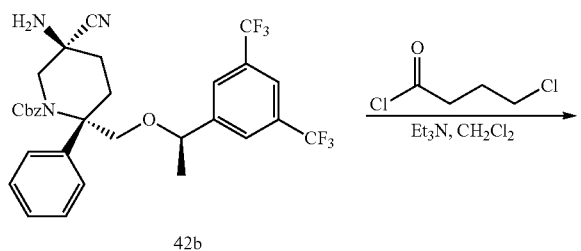 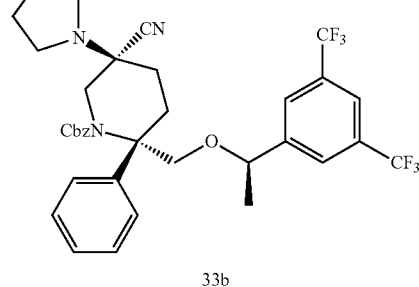

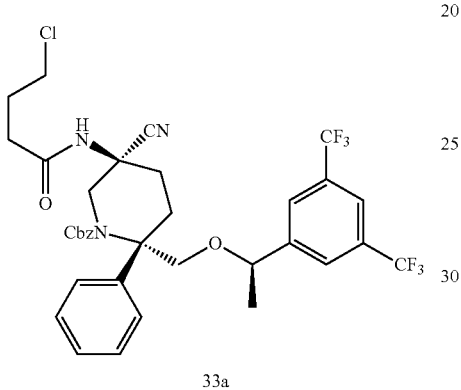

In a 25 ml round-bottomed flask, Compound 42b (0.322 g, 0.53 mmol, 1.0 equiv) was taken up in 5 ml of CH$_2$Cl$_2$ and the reaction mixture was cooled to 0° C. in an ice bath. Et$_3$N (0.111 mL, 0.79 mmol, 1.5 equiv) followed by 4-chlorobutyryl chloride (0.072 ml, 0.64 mmol, 1.2 equiv) was then added to the reaction mixture, which was slowly warmed to room temperature and stirred for 14 hrs. The progress of the reaction was monitored by TLC (60:40 EtOAc/hexane eluent) and MS. Upon completion of the reaction, the reaction mixture was diluted with CH$_2$Cl$_2$ and quenched with saturated NaHCO$_3$ followed by brine. The organic layer was dried over Na$_2$SO$_4$ and concentrated to give crude Compound 33a (0.32 g), which was used in the next step without further purification.

Step 2:

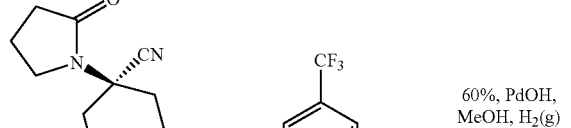

-continued

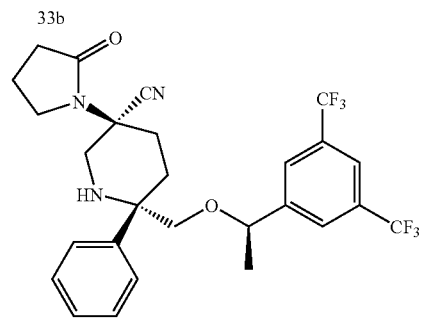

In a flame dried 25 ml round-bottomed flask, Compound 33a (0.32 g, 0.45 mmol, 1.0 equiv) was taken up in dry THF. To this solution, 60% NaH (0.025 g, 0.68 mmol, 1.5 equiv) was added, and the reaction mixture was stirred at room temperature for 2 hrs. The progress of the reaction was monitored by TLC (60:40 EtOAc/hexane) and MS. Upon completion of the reaction, the reaction mixture was diluted with EtOAc and quenched with saturated NaHCO$_3$. The organic layer was dried over Na$_2$SO$_4$ and concentrated to give Compound 33b (0.4 g), in the form of a yellow oil, which was used in the next step without further purification.

Step 3:

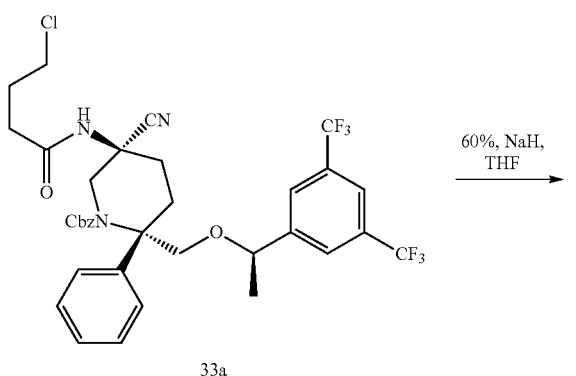

Compound 33b (0.4 g, 0.59 mmol, 1.0 equiv) was dissolved in dry MeOH (4.0 mL) and was treated with 20% Pd(OH)$_2$ (60% wt.) under an inert atmosphere. The reaction was hydrogenated at atmospheric pressure and the progress of the reaction was monitored by TLC (40:60 EtOAc/hexane eluent). The reaction was completed in 45 min, was filtered through CELITE and washed using EtOAc and concentrated to give a crude product. Purification of the crude product was carried out using BIOTAGE chromatography (60/40 EtOAc/hexane) to give Compound 33 (0.18 g, 59%).

HRMS (FAB) calculated for $C_{26}H_{28}F_6N_3O_2$ (M+1) 540.2086. found 540.2078.

Preparative Example 34

Example 34

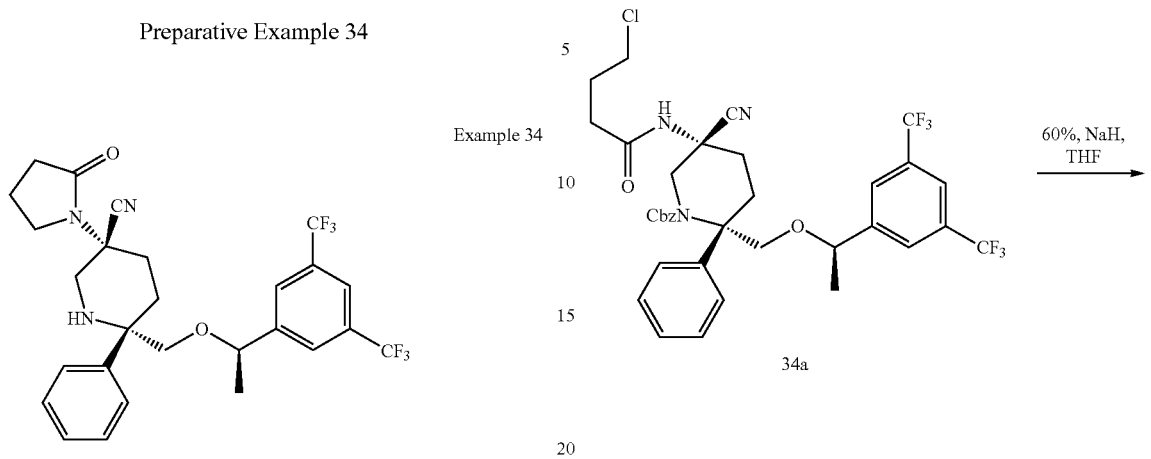

Step 1:

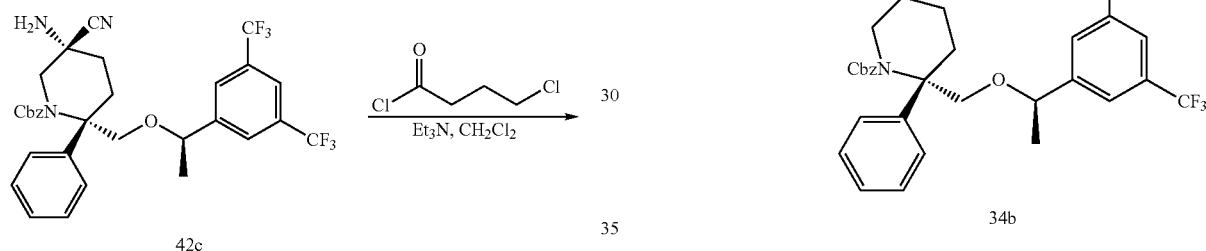

Step 2:

In a flame dried 25 ml round-bottomed flask, Compound 348 (0.23 g, 0.38 mmol, 1.0 equiv) was taken up in dry THF (1 mL). To this reaction mixture, 60% NaH (0.022 g, 0.57 mmol, 1.5 equiv) was added and the reaction mixture was stirred at room temperature for 2 hrs. The progress of the reaction was monitored by TLC (60:40 EtOAc/hexane eluent) and MS. Upon completion of the reaction, the reaction mixture was diluted with EtOAc and quenched with saturated $NaHCO_3$. The organic layer was dried over $Na_2SO_4$ and concentrated to give Compound 34b (0.21 g) in the form of a yellow oil, which was used in the next step without further purification.

Electrospray MS [M+1] 674.2.

Step 3:

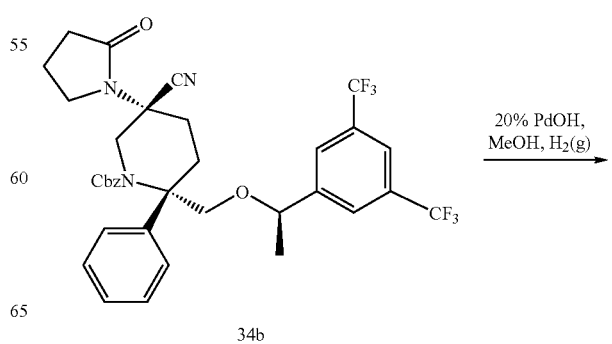

In a 25 ml round-bottomed flask, Compound 42c (0.23 g, 0.38 mmol, 1.0 equiv) was taken up in 3 mL of $CH_2Cl_2$, and the reaction mixture was cooled to 0° C. in an ice bath. $Et_3N$ (0.079 ml, 0.57 mmol, 1.5 equiv) followed by 4-chlorobutyryl chloride (0.051 ml, 0.45 mmol, 1.2 equiv) was then added to the reaction mixture, which was slowly warmed to room temperature and was stirred for 14 hrs. The progress of the reaction was monitored by TLC (60:40 EtOAc/hexane eluent) and MS. Upon completion of the reaction, the reaction mixture was diluted with $CH_2Cl_2$ and quenched with saturated $NaHCO_3$ followed by brine. The organic layer was dried over $Na_2SO_4$ and concentrated to give crude Compound 34a (0.23 g), which was used in the next step without further purification.

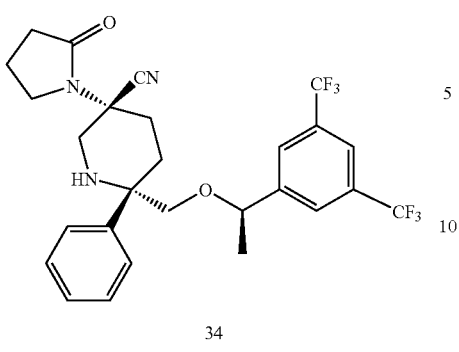

34

Compound 34b (0.21 g, 0.31 mmol, 1.0 equiv) was dissolved in dry MeOH (2.0 mL) and was treated with 20% Pd(OH)$_2$ (40% wt.) under an inert atmosphere. The reaction mixture was hydrogenated at atmospheric pressure and the progress of the hydrogenation was monitored by TLC (40:60 EtOAc/hexane eluent). After 45 min, the reaction mixture was filtered through CELITE, washed with EtOAc, and concentrated to give a crude product. The crude product was purified using BIOTAGE chromatography (60/40 EtOAc/hexane), to give Compound 34 (0.10 g, 59%).

HRMS (FAB) calculated for $C_{26}H_{28}F_6N_3O_2$(M+1) 540.2086. found 540.2078.

Preparative Example 35

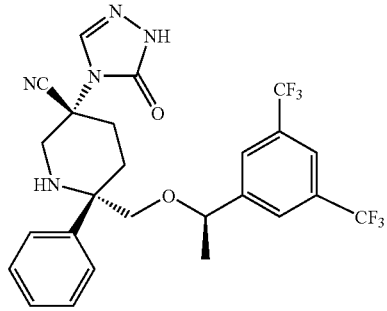

Compound 35

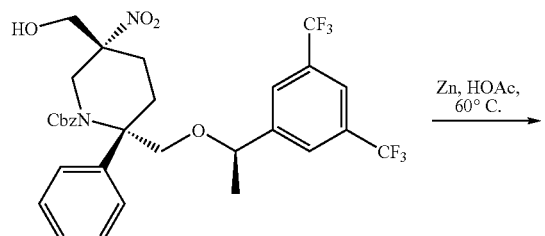

Compound 23d

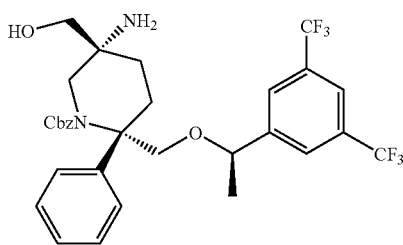

Compound 35a

Compound 35 was prepared using a procedure similar to procedure for preparing Compound 23e in Example 23.

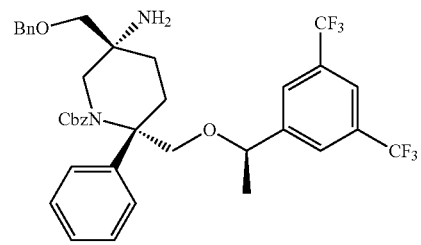

Compound 35a

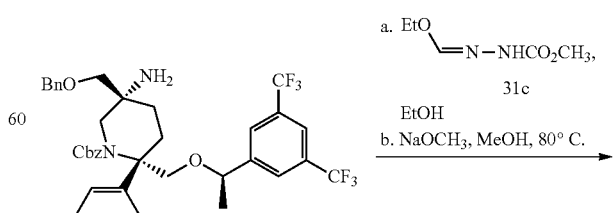

Compound 35b

Likewise, Compound 35b was prepared by a procedure similar to the procedure used to prepare Compound 23f in Example 23.

Compound 35b

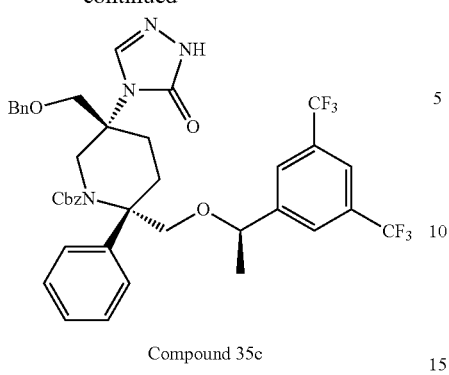

Compound 35c

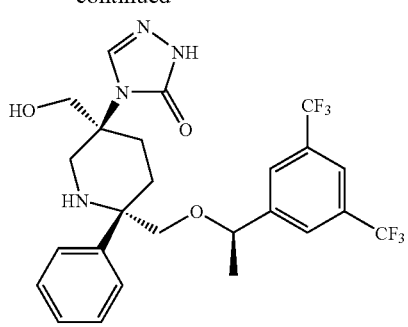

Compound 35e

Compound 35c was prepared by a procedure similar to the procedure used to prepare Compound 23g in Example 23.

Compound 35e was prepared by a procedure similar to the procedure for preparing Compound 23h in Example 23.

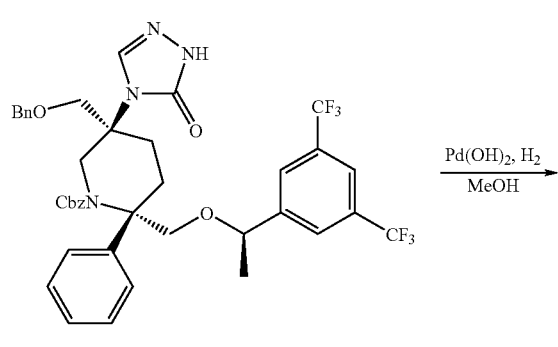

Compound 35c

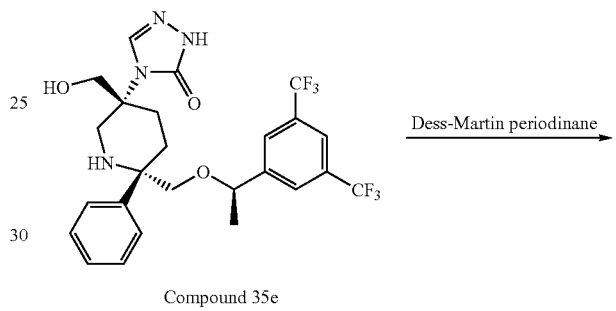

Compound 35e

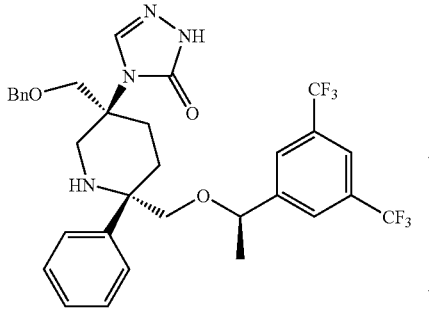

Compound 35d

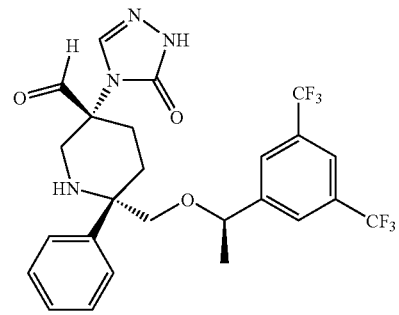

Compound 35f

Compound 35d was prepared by a procedure similar to the procedure for preparing Compound 23 in Example 23.

Compound 35f was preparing by a procedure similar to the procedure for preparing Compound 42e in Example 42.

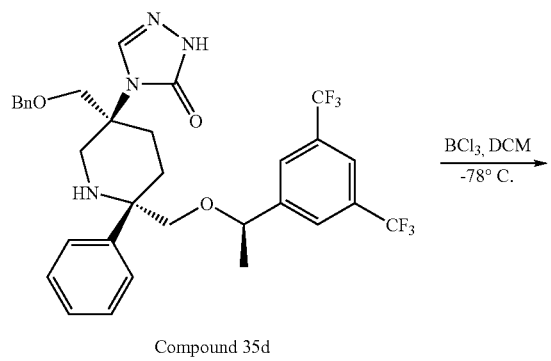

Compound 35d

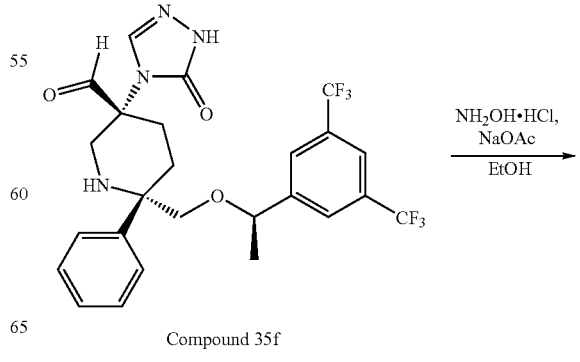

Compound 35f

115

-continued

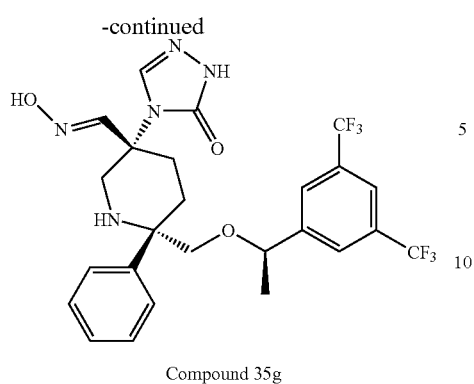

Compound 35g

Compound 35g was prepared by a procedure similar to the procedure for preparing Compound 42g in Example 42.

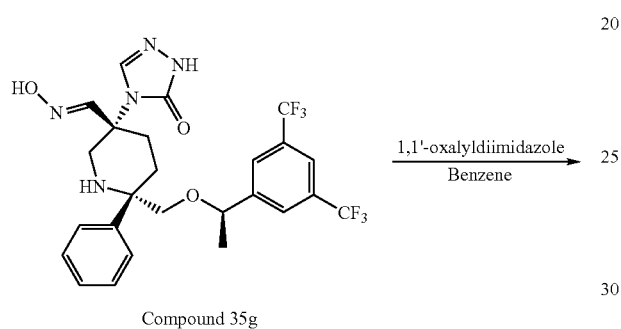

Compound 35g

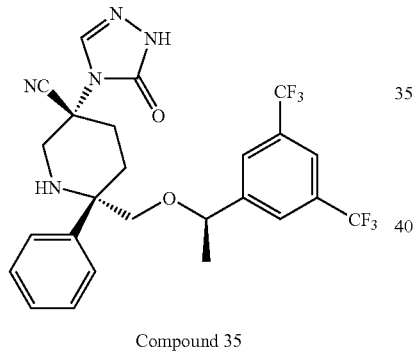

Compound 35

Compound 35 was prepared by a procedure similar to the procedure for preparing Compound 42 in Example 42. HRMS calculated for $C_{25}H_{23}F_8N_5O_2$ (M+H) 540.1834. found 540.1822.

Preparative Example 36

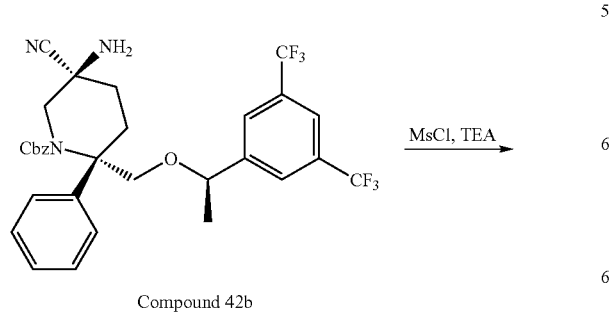

Compound 42b

116

-continued

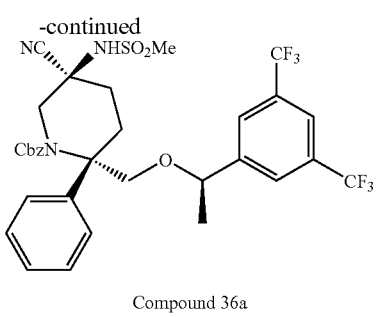

Compound 36a

Step A:

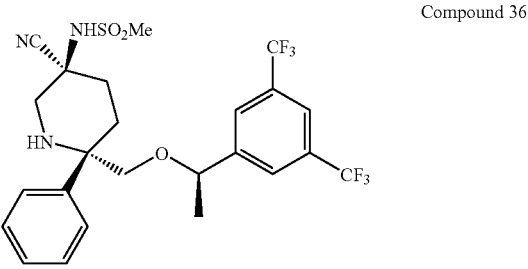

Compound 36

Compound 36a was prepared by a procedure similar to the procedure for preparing Compound 47 in Example 47.

Step B:

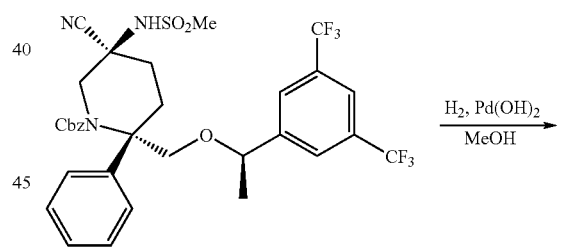

Compound 36a

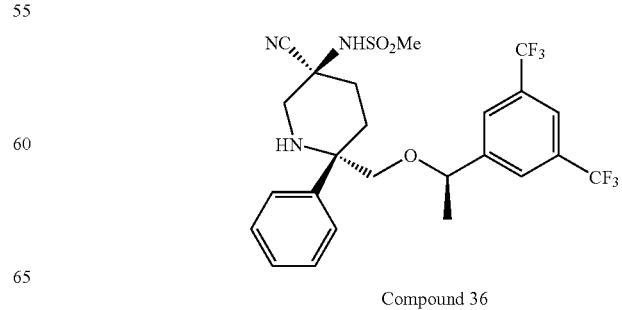

Compound 36

Compound 36 was prepared by a procedure similar to the procedure for preparing Compound 23 in Example 23. HRMS calculated for $C_{24}H_{25}F_6N_3O_3S$ (M+H) 550.1599. found 550.1603.

Preparative Example 37

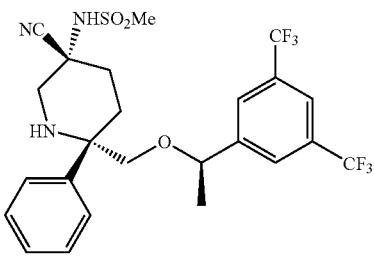

Compound 37

Step A:

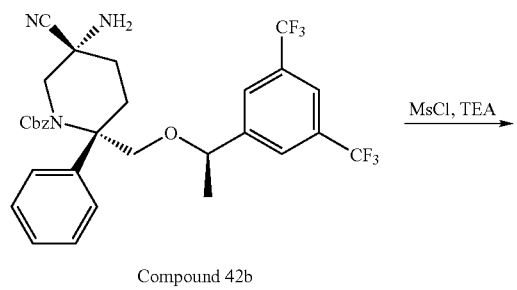

Compound 42b

MsCl, TEA →

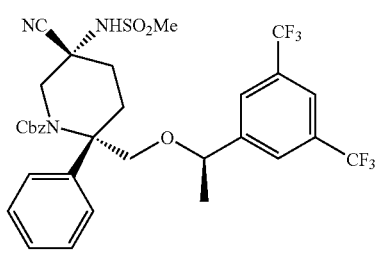

Compound 37a

Compound 37a was prepared by a procedure similar to the procedure for preparing compound 47 in Example 47.

Step B:

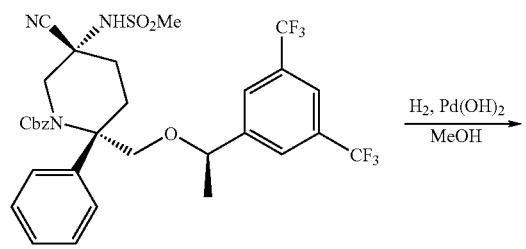

Compound 37a $H_2$, $Pd(OH)_2$ / MeOH →

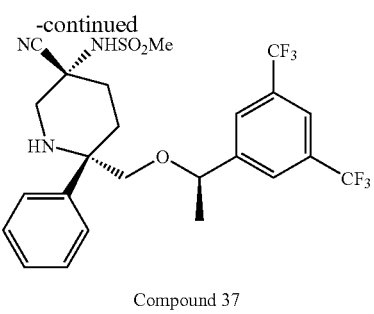

Compound 37

Compound 37 was prepared using a procedure similar to the procedure for preparing Compound 23 in Example 23. HRMS calculated for $C_{24}H_{25}F_6N_3O_3S$ (M+H) 550.1599. found 550.1603.

Preparative Example 38

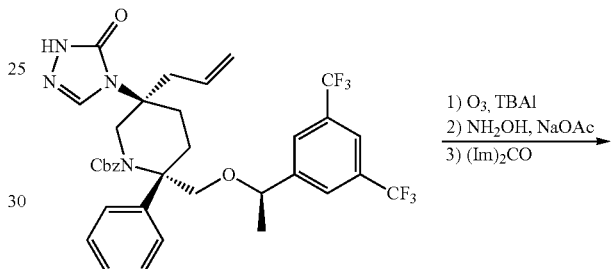

31g

1) $O_3$, TBAI
2) $NH_2OH$, NaOAc
3) $(Im)_2CO$ →

38a

Step 1:

To a solution of Compound 31g (640 mg, 0.93 mmol) in 10 mL $CH_2Cl_2$ maintained at −78° C. was bubbled $O_3$ gas until the reaction mixture turn blue.

The reaction mixture was then purged with nitrogen until it became colorless. TBAI (412 mg, 1.11 mmol) was then added and the reaction mixture was stirred at 20° C. for 2 h. The reaction mixture was diluted with diethyl ether, washed with saturated aqueous $Na_2S_2O_3$, water and brine, and the dried and concentrated. The resulting residue was dissolved in EtOH (22 mL) and NaOAc (262.7 mg, 3.2 mmol) and hydroxylamine hydrochloride salt (222 mg, 3.2 mmol) were added, and the mixture was stirred overnight. The reaction mixture was then concentrated and the residue was partitioned between 20 mL EtOAc and water. The organic layer was dried and concentrated. The crude intermediate was dissolved in toluene (6.8 mL) followed by the addition of 1,1'-oxallyldiimidazole (165 mg, 1.8 mmol) and the mixture was heated at 80° C. for 2 h. After cooling the reaction mixture to 23° C., the toluene solution was loaded to a silica gel column and eluted with 20-100% EtOAc/hexanes to give product Compound 38a. MS [M+1]$^+$ 688.1.

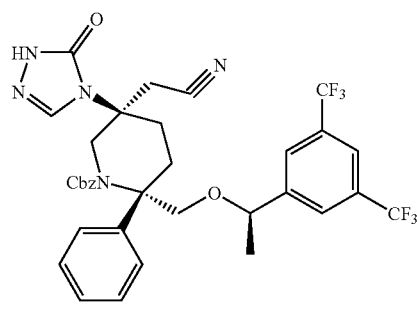

38a

Pd(OH)$_2$/C, H2

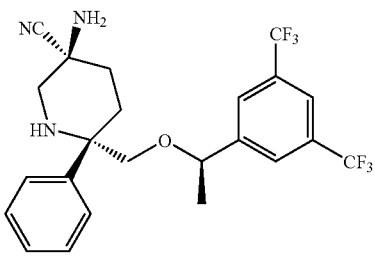

Compound 42b

+

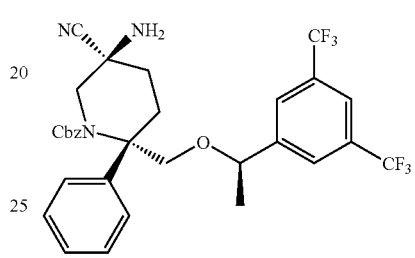

Compound 42c

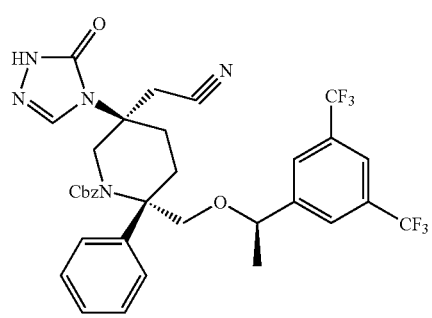

Compound 38

Step 2:

Using a procedure similar to that of Example 31, Step 6, Compound 38a was hydrogenated to give Compound 38. MS [M+1]$^+$ 554.1.

Preparative Example 39 and 40

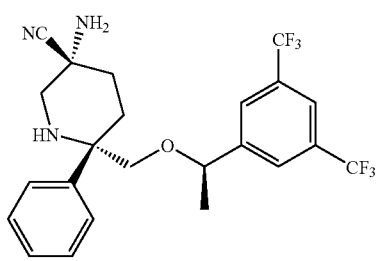

Compound 39

-continued

Compound 40

Step A:

H$_2$, Pd(OH)$_2$
MeOH

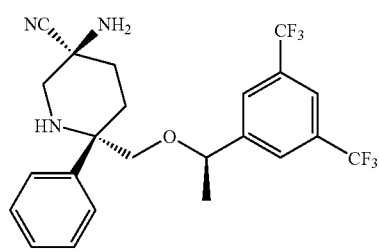

Compound 40

+

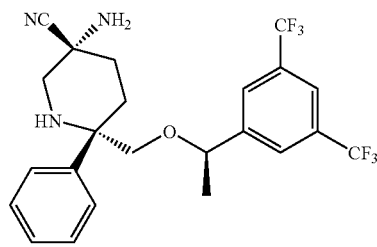

Compound 39

Compounds 39 and 40 were prepared using a procedure similar to the procedure for preparing Compound 38. HRMS calculated for $C_{23}H_{23}F_6N_3O$ (M+H) 472.1824. found 472.1820.

Preparative Example 41

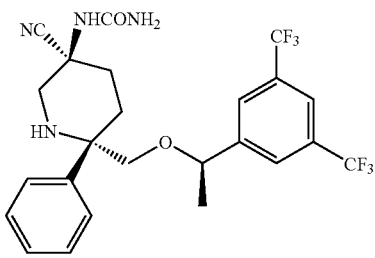

Compound 41

Step A:

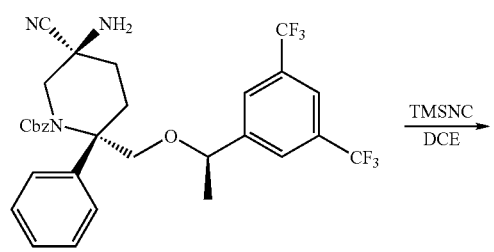

Compound 42b

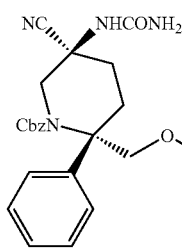

Compound 41a

In a 25 mL round-bottomed flask Compound 42b (0.15 g, 0.248 mmol, 1.0 equiv) was dissolved in 6 mL of DCE. Trimethylsilyl isocyanate (0.51 mL, 3.72 mmol, 15.0 equiv) was added and the reaction mixture was refluxed at 80° C. overnight. The reaction mixture was cooled and quenched with saturated $NaHCO_3$ (10 mL). The aqueous phase was extracted with EtOAc (2 ×10 mL). The organic layers were washed with brine (5 mL), dried over $MgSO_4$, and concentrated. The crude product was purified by preparative TLC (1:1 EtOAc:hexanes) to yield 0.060 g (37%) of Compound 41a.

Step B:

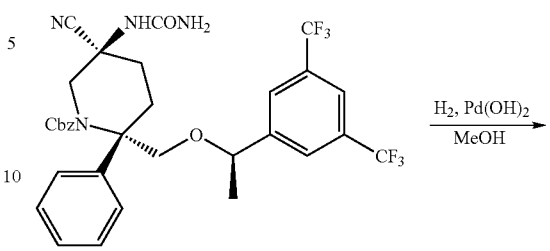

Compound 41a

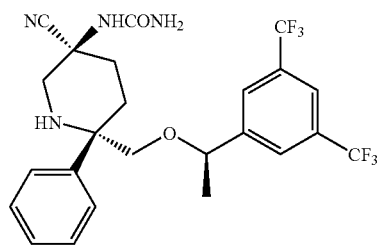

Compound 41

Compound 41 was prepared by a procedure similar to procedure for preparing Compound 23 in Example 23. HRMS calculated for $C_{24}H_{24}F_6N_4O_2$ (M+H) 515.1882. found 515.1874.

Preparative Example 42

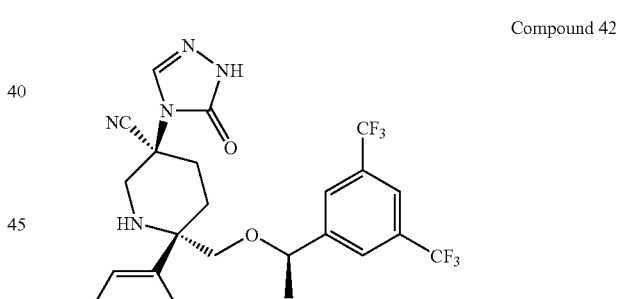

Compound 42

Step A:

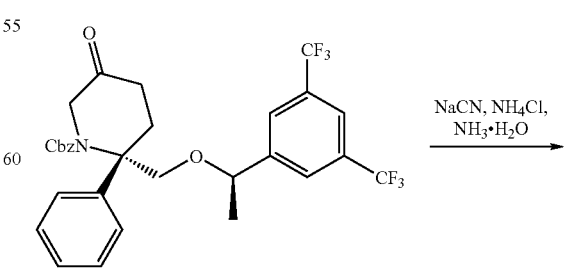

Compound 41a

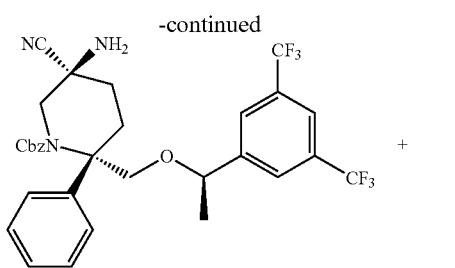

Compound 42c

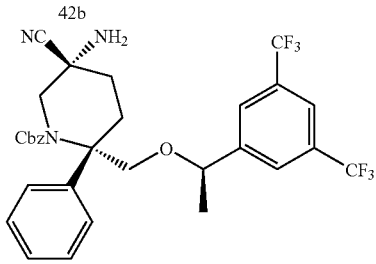

Compound 41a (6.87 g, 11.86 mmol) in EtOH (7 mL) was added to a solution of NaCN (0.767 g), NH₄Cl (0.889 g) and NH₃·H₂O (3.84 mL) in EtOH (7.0 mL) and water (7.0 mL) at room temperature in a sealed tube. The seated tube was then heated at 60° C. for 12 hours before it was cooled down to room temperature. The reaction mixture was diluted with EtOAc (200 mL) and washed with water (50 mL). The aqueous phase was extracted with EtOAc (3×30 mL). The combined organic layers were washed with brine (30 mL), and dried over MgSO₄. After filtration and concentration, the crude product was purified using BIOTAGE chromatography (hexane/EtOAc, v/v=7/2 to 5/2) to give Compound 42b (2.6 g, 36%) and Compound 42c (1.8 g, 25%).

Step B:

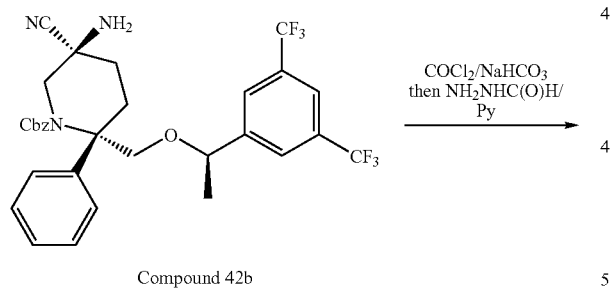

Compound 42d

Phosgene (6.67 mL, 12.4 mmol, 20% in toluene) was added dropwise to a vigorously stirred mixture of Compound 42b (1.5 g, 2.48 mmol) in CH₂Cl₂ (30 mL) and a saturated NaHCO₃ solution (30 mL) at 0° C. The mixture was stirred at 0° C. for 3 hours before it was diluted with CH₂Cl₂ (50 mL) and the aqueous phase was separated from the organic phase. The organic phase was washed with a cold aqueous NH₄Cl solution, brine, and dried over MgSO₄. The solvent was reduced to a volume of about 5 mL under reduced pressure, at room temperature, to remove excess phosgene. The residue was dissolved in CH₂Cl₂ (15 mL) and treated with NH₂NHC(O)H (0.446 g, 7.44 mmol) and pyridine (1.2 mL, 14.88 mmol) at room temperature. The resulting solution was stirred at room temperature for 12 hours. The reaction mixture was then diluted with EtOAc (200 mL) and washed with HCl (50 mL, 0.5 N). The aqueous phase was extracted with EtOAc (3×30 mL). The combined organic layers were washed with brine (30 mL), and dried over MgSO₄. After filtration and concentration, the crude product was purified using BIOTAGE chromatography eluted with hexane/EtOAc (v/v=1/2 to 1/7) to give Compound 42d (1.1 g, 64%).

Step C:

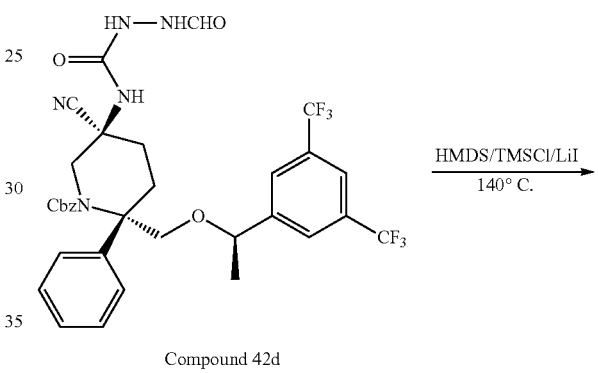

Compound 42d

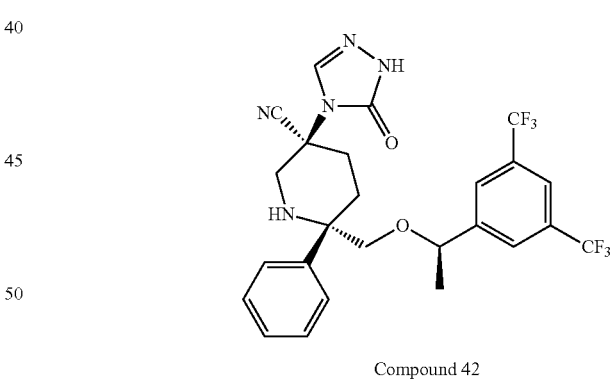

Compound 42

TMSCl (50 µL) was added to a stirring mixture of Compound 42d (15 mg, 0.0217 mmol) and LiI (2.9 mg, 0.0217 mmol) in HMDS (0.5 mL) at room temperature. The resulting reaction mixture was heated at 140° C. (bath temperature) for 30 hours before it was cooled down to room temperature. The reaction mixture was diluted with EtOAc (25 mL) and washed with HCl (5 mL, 1.0 N). The aqueous phase was extracted with EtOAc (3×10 mL). The combined organic layers were washed with brine (10 mL), and dried over MgSO₄. After filtration and concentration, the crude product was purified using preparative TLC (hexane/EtOAc, v/v=6/4) to give Compound 42 (4 mg, 34%).

Alternate Procedure for Example 42

Alternatively, Compound 42 can also be prepared from Compound 23g as follows

Step A:

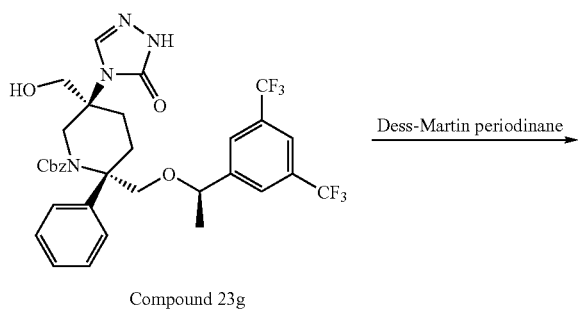

Compound 23g

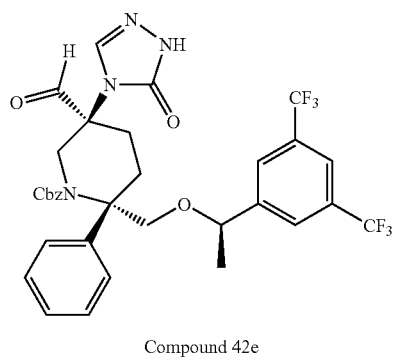

Compound 42e

In a 10 mL round-bottomed flask, Compound 23g (0.02 g, 0.037 mmol, 1.0 equiv) was dissolved in DCM (3 mL) and the reaction mixture was cooled to 0° C. Dess-Martin periodinane (0.02 g, 0.048 mmol, 1.3 equiv) was added and the reaction mixture was stirred under nitrogen at room temperature for 45 minutes. The progress of the reaction was monitored by TLC (9/1 EtOAC/MeOH eluent), and the reaction was quenched after 1.5 hrs, by pouring the reaction mixture into separatory funnel containing saturated $Na_2S_2O_3$/$NaHCO_3$ solution (1:1) (5 mL). The mixture in the separatory funnel was shaken vigorously, and the aqueous layer was extracted with $Et_2O$ (2×5) and dried over $MgSO_4$ and concentrated to give crude Compound 42e (0.02 g), which was used in the next step without further purification.

Step B:

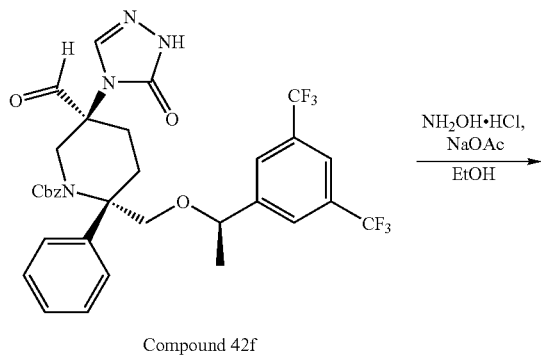

Compound 42f

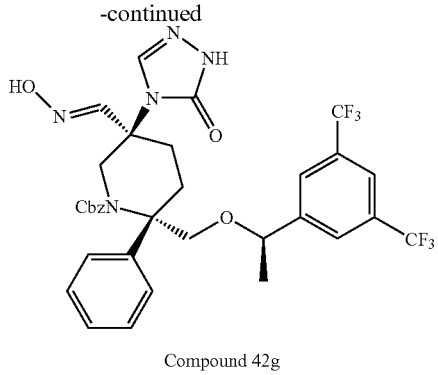

Compound 42g

In a 25 mL round-bottomed flask, Compound 42f (0.09 g, 0.13 mmol, 1.0 equiv) and sodium acetate (0.032 g, 0.39 mmol, 3.0 equiv) were dissolved in EtOH (6 mL), to which hydroxylamine hydrochloride (0.056 g, 0.080 mmol, 6.0 equiv) was added. The reaction mixture was stirred under nitrogen at room temperature overnight. The reaction mixture was then diluted with EtOAc (15 mL), quenched with saturated $NaHCO_3$ (5 mL), and the organic layer was washed using brine (5 mL) and dried over $MgSO_4$ to give crude Compound 42g (0.95 g), which was used in the next step without further purification.

Step C:

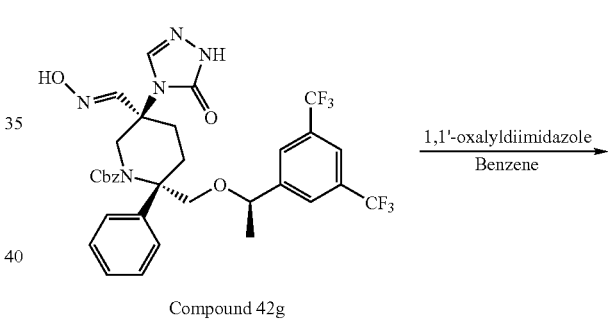

Compound 42g

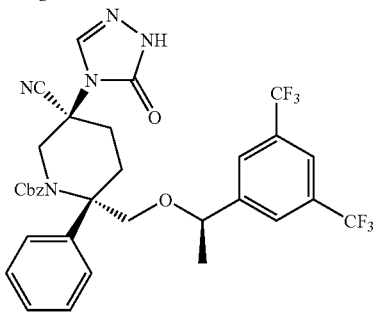

Compound 42h

In a 50 mL round-bottomed flask, Compound 42g (1.1 g, 0.59 mmol, 1.0 equiv) was dissolved in benzene (25 mL). 1,1'-oxalyldiimidazole (0.302 g, 1.89 mmol, 1.5 equiv) was added to the solution, and the reaction mixture was heated to 75° C. under nitrogen for 4 hrs. The reaction mixture was then quenched with water (20 mL), diluted with EtOAc (30 mL), dried over $MgSO_4$ and concentrated to give a crude product. The crude product was purified using BIOTAGE chromatography (1/1 EtOAc/hexanes) to give Compound 42h (0.7 g, 66% over three steps).

Step D:

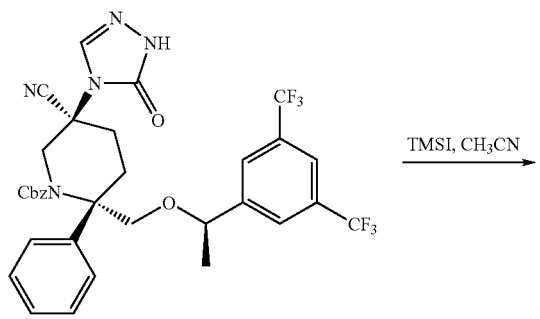

Compound 42i

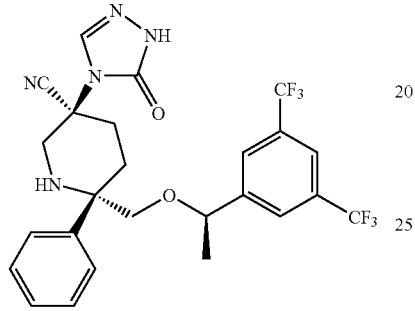

Compound 42

In a 50 mL round-bottomed flask, Compound 42i (0.5 g, 0.742 mmol, 1.0 equiv) was taken up in acetonitrile (9 mL). The reaction mixture was cooled to 0° C., and TMSI (0.742 mL, 5.19 mmol, 7.0 equiv) was added dropwise via syringe. The reaction mixture was stirred overnight at room temperature. The progress of the reaction was monitored by MS, which indicated some starting material was still present. The reaction mixture was quenched using saturated $Na_2S_2O_3$/$NaHCO_3$ (1:1) (10 mL) and diluted with EtOAc (20 mL). The organic layer was washed with brine (10 mL), dried over $MgSO_4$, and concentrated to yield a crude product. The crude product was purified using BIOTAGE chromatography (60/40 EtOAc/hexanes) to give Compound 42 (0.4 g). HRMS calculated for $C_{25}H_{23}F_6N_5O_2$ (M+H) 540.1834. found 540.1813.

Preparative Example 43

Compound 43

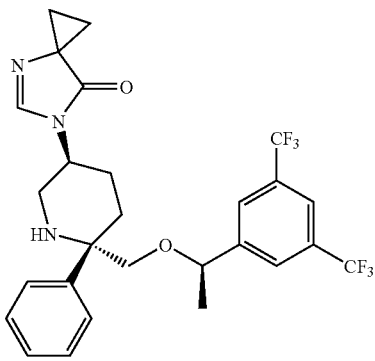

Step A:

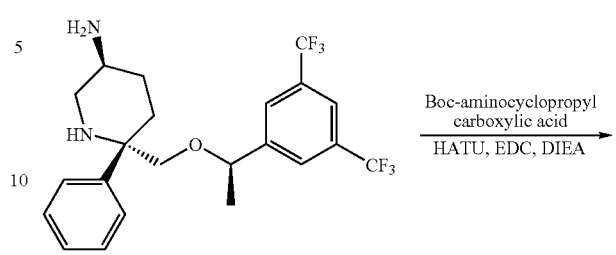

Compound 44b

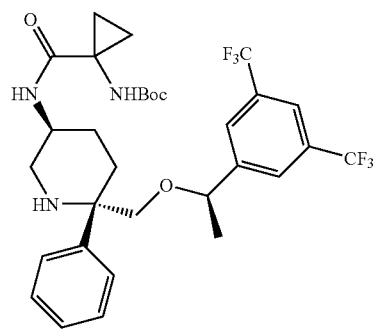

Compound 43a

Compound 43a was prepared by a procedure similar to the procedure for preparing Compound 28a.

Step B:

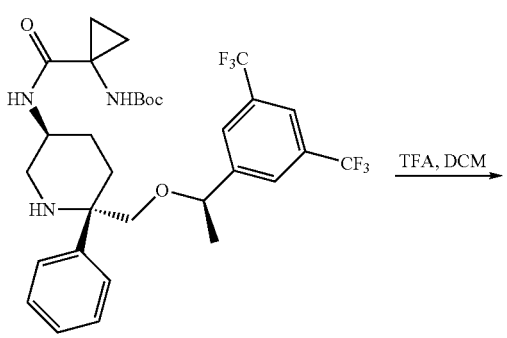

Compound 43a

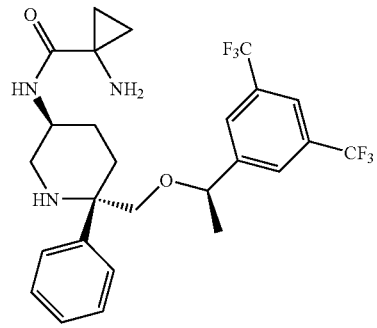

Compound 43b

Compound 43b was prepared by a procedure similar to the procedure for preparing Compound 45c.

Step C:

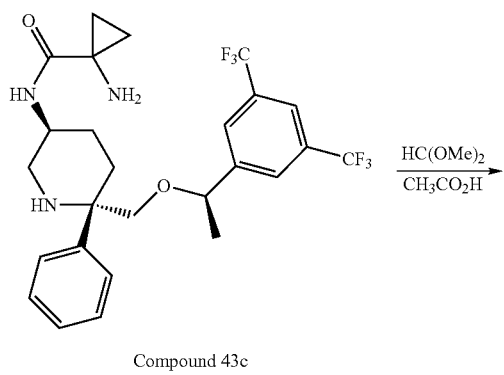

Compound 43c

HC(OMe)₂ / CH₃CO₂H

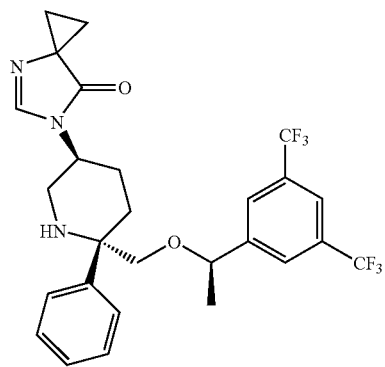

Compound 43

Compound 43 was prepared by a procedure similar to the procedure for preparing Compound 28 (step c).

Preparative Example 44

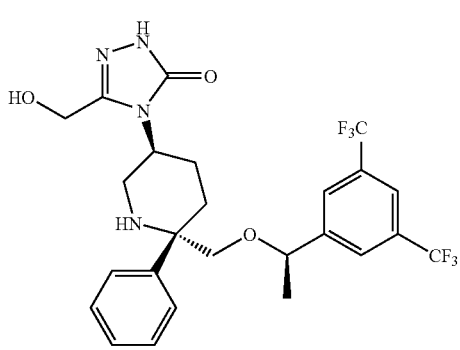

Compound 44

Step A:

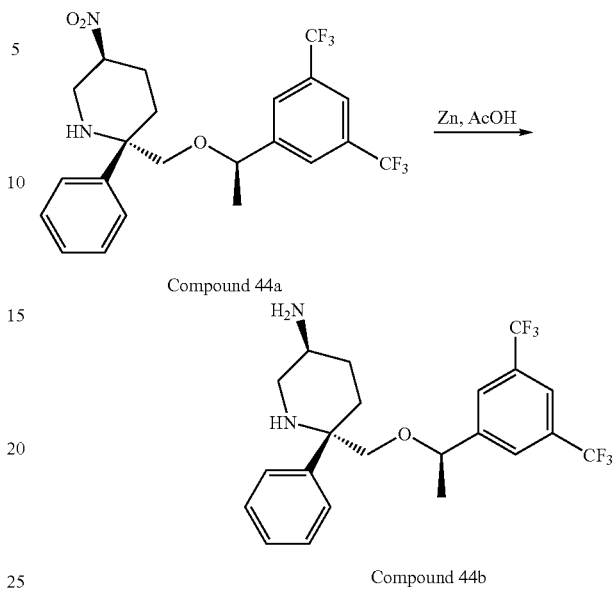

Compound 44a

Zn, AcOH

Compound 44b

In a 50 mL round-bottomed flask, Compound 44a (1.1 g, 2.31 mmol, 1.0 equiv) was dissolved in acetic acid (20 mL), and the resulting reaction mixture was cooled to 0° C. Zn powder (1.51 g, 23.1 mmol, 10.0 equiv) was added and the mixture was refluxed for 2.5 hr. The reaction mixture was then filtered through CELITE, concentrated, diluted with EtOAc (30 mL), and neutralized with saturated NaHCO₃ (30 mL). The aqueous phase was extracted with EtOAc (2×10 mL), washed with brine (20 mL), dried over MgSO₄ and concentrated. The crude product was purified using a filter column to yield 1.0 g (99%) of Compound 44b.

Step B:

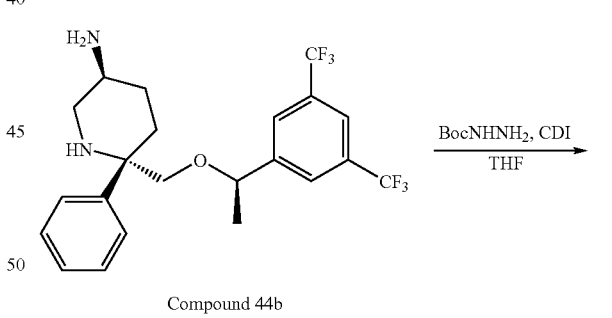

Compound 44b

BocNHNH₂, CDI / THF

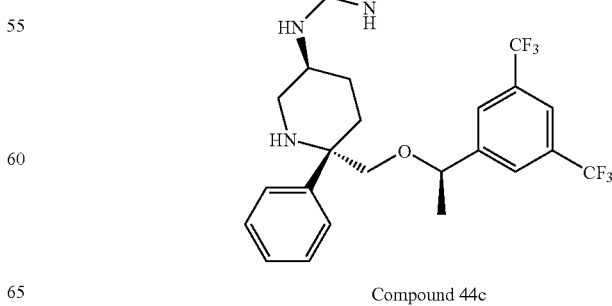

Compound 44c

Compound 44c was prepared by a procedure similar to the procedure for preparing Compound 45b.

Step C:

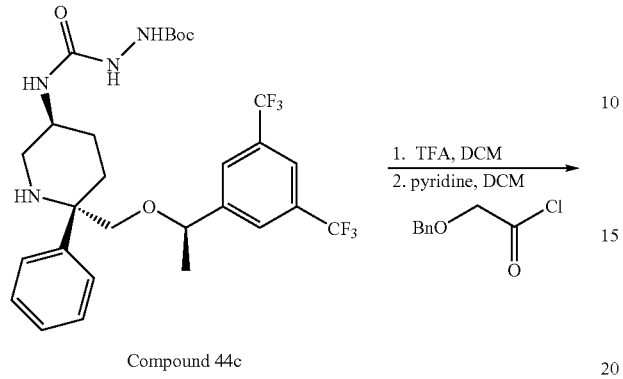

Compound 44c

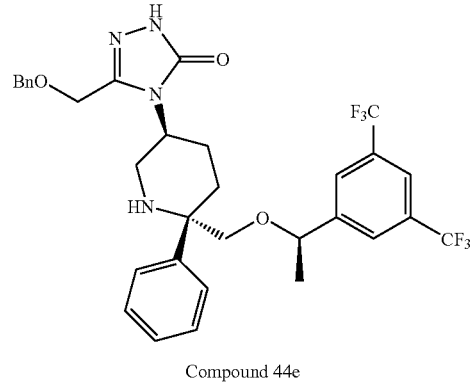

Compound 44e

Compound 44e was prepared by a procedure similar to the procedure for preparing Compound 45d.

Step E:

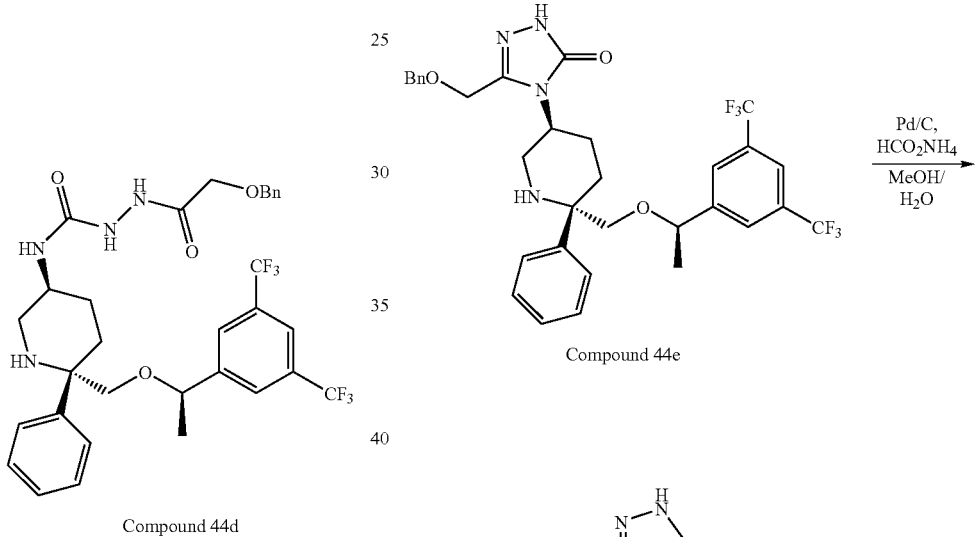

Compound 44d was prepared by a procedure similar to the procedure for preparing Compound 45c.

Step D:

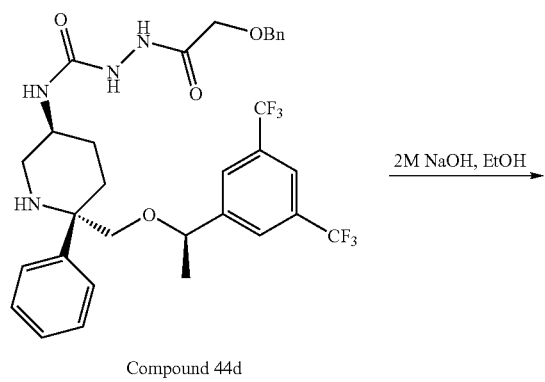

Compound 44d

In a 10 mL round-bottomed flask, Compound 44e (0.34 g, 0.54 mmol, 1.0 equiv) was taken up in 5.5 mL of MeOH/H$_2$O (10:1). The round-bottomed flask was degassed, and Pd/C (10 wt %, 0.18 g) was added followed by HCO$_2$NH$_4$ (0.174 g, 2.68 mmol, 5.0 equiv). The resulting heterogeneous mixture was refluxed overnight, cooled, filtered through CELITE, concentrated, diluted with EtOAc (10 mL), washed with saturated NaHCO$_3$ (10 mL), and dried over Na$_2$SO$_4$. The crude product was purified by BIOTAGE chromatography (9:1

EtOAc:MeOH) to yield 0.11 g (38%) of Compound 44. HRMS calculated for $C_{25}H_{26}F_5N_4O_3$ (M+H) 545.1987. found 545.1988.

Preparative Example 45 and 46

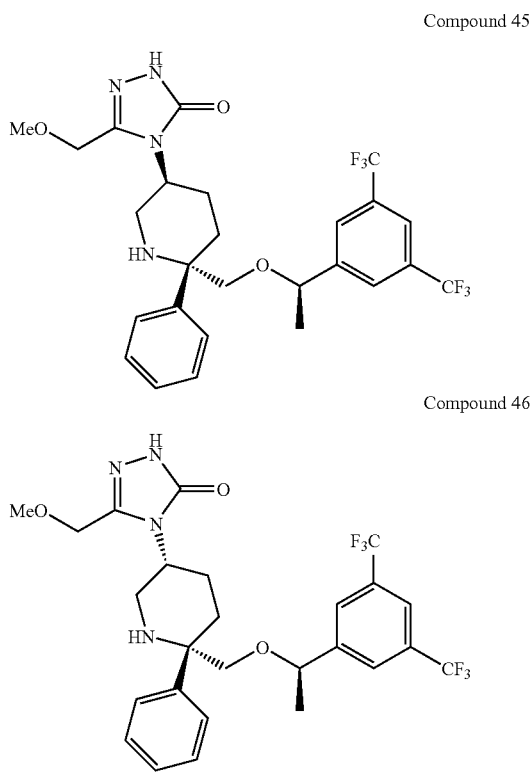

Compound 45

Compound 46

Step A:

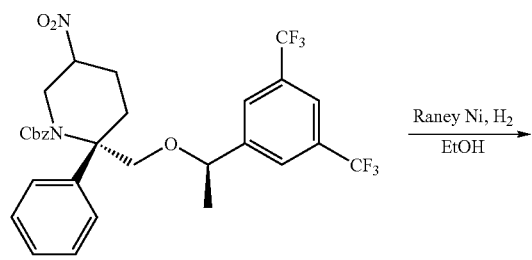

Compound 41a

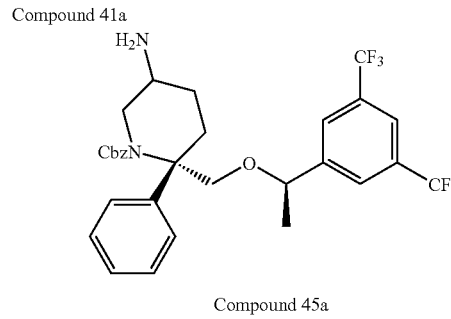

Compound 45a

Compound 41a (2.8 g, 4.59 mmol, 1.0 equiv) was taken up in ethanol (15 mL). Raney nickel was added to the solution, and the reaction mixture was hydrogenated in a Parr shaker at 60 psi. The progress of the hydrogenation was monitored by TLC (4/1 EtOAc/hexanes). After 3 hours, the reaction mixture was then filtered through CELITE, washed with ethanol (30 mL) and concentrated. The crude product was purified by BIOTAGE chromatography (4/1 EtOAc/hexanes), to give Compound 45a (1.75 g, 65%).

Step B:

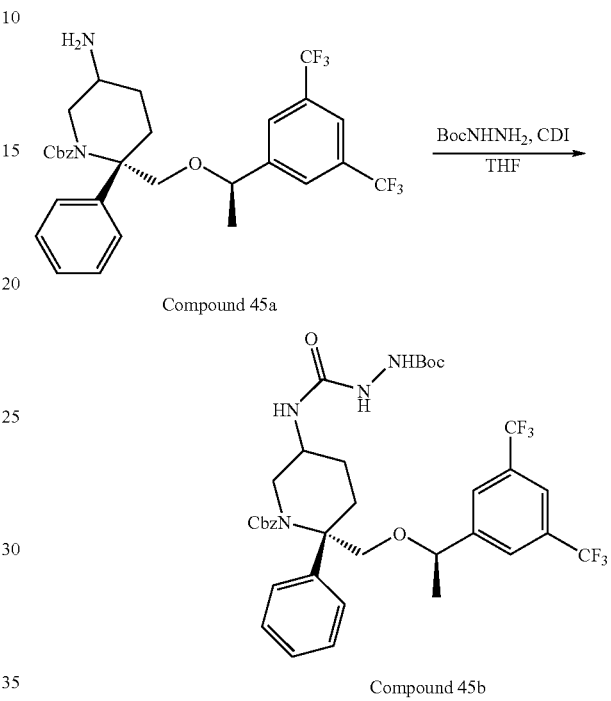

Compound 45a

Compound 45b

In a 50 mL round-bottomed flask, Compound 45a (1.0 g, 1.72 mmol, 1.0 equiv) was dissolved in dry THF (20 mL) and cooled to 0° C. A solution of tert-butyl carbazate (0.228 g, 1.72 mmol, 1.0 equiv) and carbonyl diimidazole (0.335 g, 2.06 mmol, 1.2 equiv), which was previously stirred in dry THF (10 mL), was added to the above cooled solution via cannula. The reaction mixture was allowed to warm to room temperature and was stirred overnight. The reaction mixture was then concentrated and purified by BIOTAGE chromatography (1/1 EtOAc/hexanes) to give Compound 45b (0.85 g, 67%).

Step C:

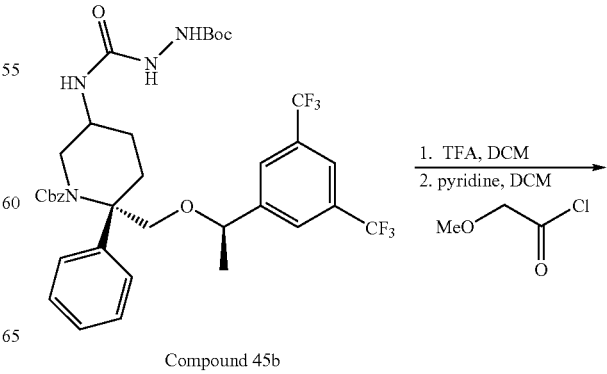

Compound 45b

-continued

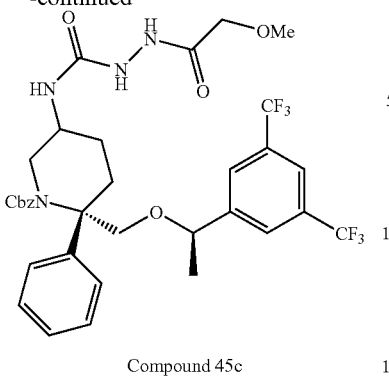

Compound 45c

In a 50 mL round-bottomed flask, Compound 45b (0.39 g, 0.53 mmol, 1.0 equiv) was dissolved in CH$_2$Cl$_2$ (10.0 mL) and cooled to 0° C. Trifluoroacetic acid (1.02 mL, 13.2 mmol, 25.0 equiv) was added to the solution, and the reaction mixture was allowed to stir at room temperature. The progress of the reaction was monitored by MS (i.e., disappearance of starting material). The reaction mixture was concentrated after 7 h, and was used in the next step without any further purification. The crude intermediate was dissolved in THF (5 mL) and cooled to 0° C. A 20% aqueous solution of NaOH (5.0 mL) was added, followed by methoxyacetyl chloride (0.096 mL, 1.06 mmol, 2.0 equiv). The reaction mixture was allowed to stir at room temperature overnight, and was then diluted with H$_2$O (10 mL), extracted with Et$_2$O (2×10 mL), washed with brine (10 mL), dried over MgSO$_4$ and concentrated to yield crude Compound 45c (0.35 g, 95%), which was used in the next step without any further purification.

Step D:

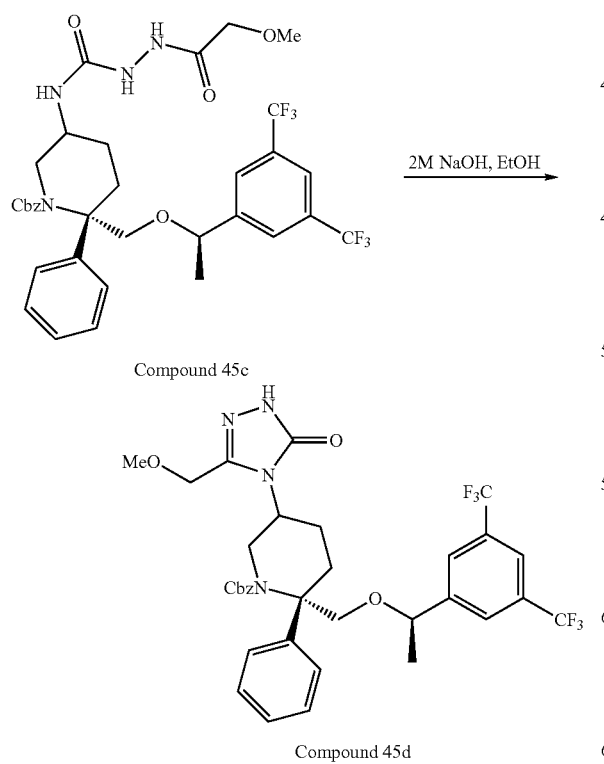

Compound 45d

In a 25 mL round-bottomed flask, Compound 45c (0.35 g, 0.49 mmol, 1.0 equiv) was dissolved in EtOH (3.0 mL). 3.0 mL of a 6 M solution of NaOH was added and the reaction mixture was refluxed overnight. The reaction mixture was then concentrated and purified by preparative TLC (EtOAc) to give 0.145 g (42%) of Compound 45d.

Step E:

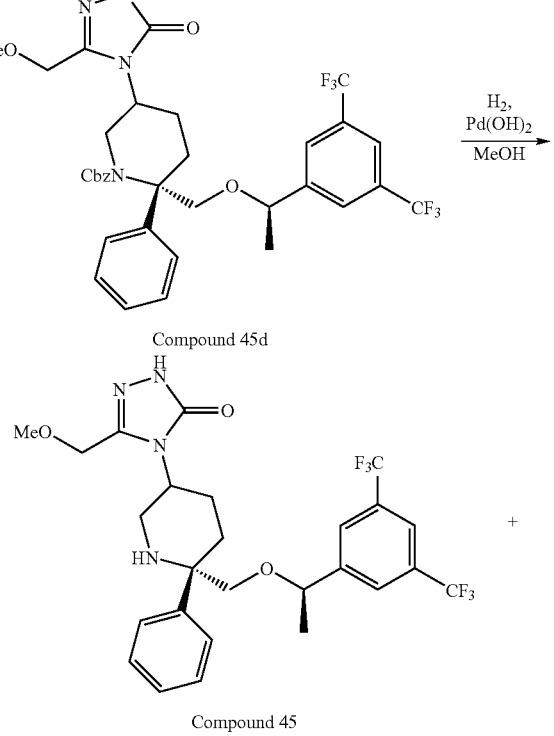

Compound 45

Compound 46

In a 10 mL round-bottomed flask, Compound 45d (0.125 g, 0.18 mmol, 1.0 equiv) was dissolved in 3 mL MeOH. Pd(OH)$_2$ (0.010 g, 0.072 mmol, 40 wt %) was added, and the heterogeneous mixture was hydrogenated at room temperature. The progress of the hydrogenation was monitored by MS. The reaction mixture was filtered through CELITE, concentrated and purified by preparative TLC (EtOAc) affording a mixture of Compounds 45 and 46 (0.008 g, 8%). HRMS calculated for C$_{26}$H$_{28}$F$_6$N$_4$O$_3$ (M+H) 559.2144. found 559.2146.

Preparative Example 47 and 48
Compound 47
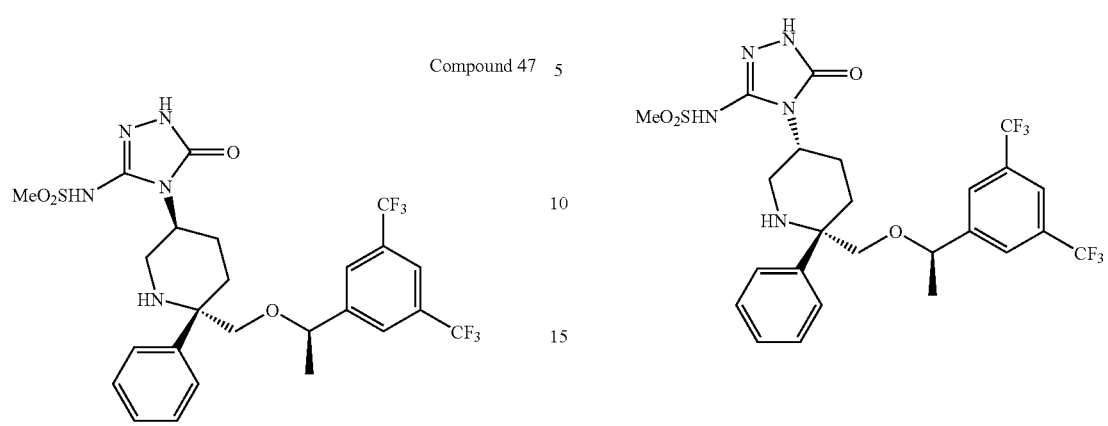
Compound 48
Step A:
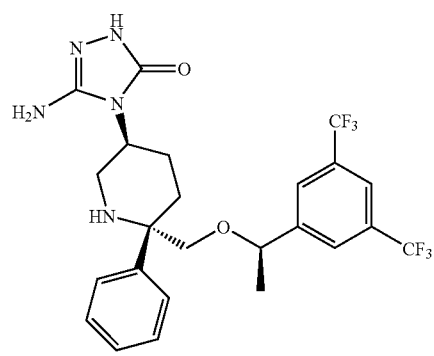
Compound 49
+
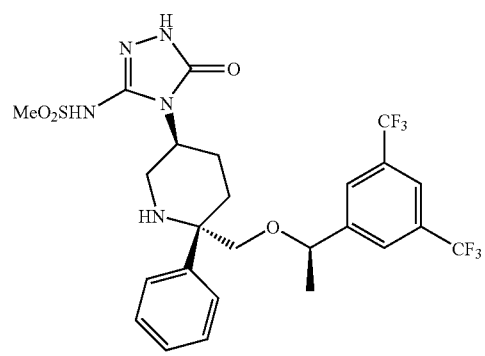
Compound 47
+
→ MsCl, TEA
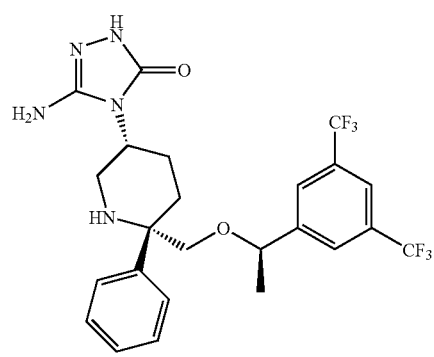
Compound 50
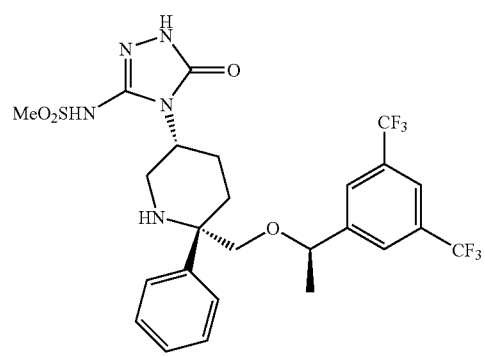
Compound 48

In a 10 mL round-bottomed flask, a mixture of Compounds 49 and 50 (0.025 g, 0.047 mmol, 1.0 equiv) was dissolved in 2 mL of DCM and cooled to 0° C. Triethylamine (0.0073 mL, 0.052 mmol, 1.1 equiv) was added, followed by MeSO$_2$Cl (0.004 mL, 0.052 mmol, 1.1 equiv). The reaction mixture was allowed to stir overnight. The reaction mixture was then diluted with EtOAc (10 mL) and quenched with saturated NaHCO$_3$ (5 mL). The aqueous phase was extracted with EtOAc (2×5 mL), dried over Na$_2$SO$_4$, and concentrated. The crude product was purified by preparative TLC (4:1 EtOAc/hexanes) to give 0.028 g (100%) of a mixture of Compounds 47 and 48. HAMS calculated for C$_{25}$H$_{27}$F$_6$N$_5$O$_4$S (M+H) 608.1766. found 608.1785.

Preparative Example 49 and 50

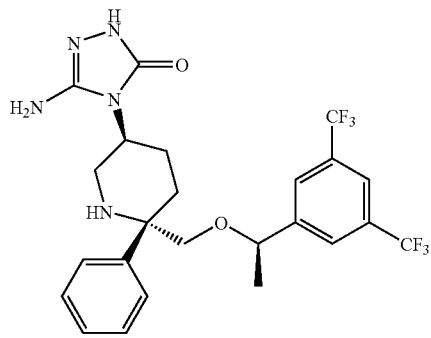

Compound 49

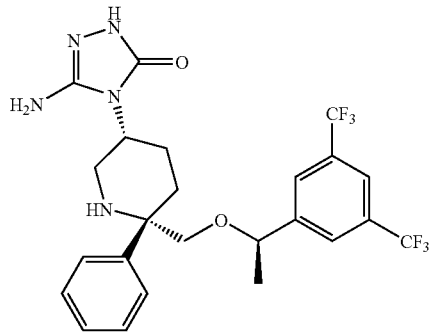

Compound 50

Step A:

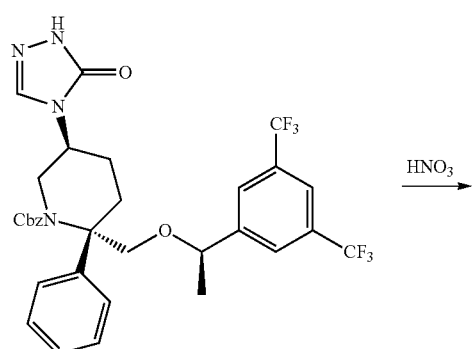

Compound 49a

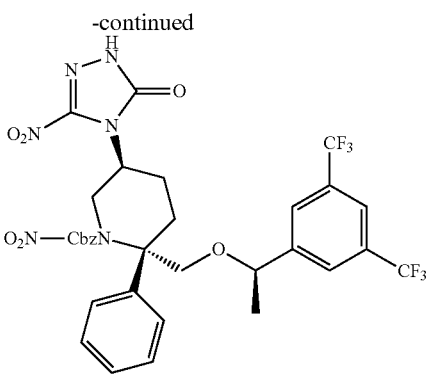

Compound 49b

Compound 49a (0.50 g, 0.77 mmol, 1.0 equiv) was added to a 50 mL round-bottomed flask. Fuming HNO$_3$ (3 mL) was then added to the flask, and the resulting reaction mixture was allowed to stand for 1 h. After the reaction was complete, ice (10 g) was added. The reaction mixture was diluted with EtOAc (25 mL) and neutralized with saturated NaOH (3 mL). The aqueous phase was extracted with EtOAc (2×10 mL). The organic layers were washed with brine (10 mL), dried over MgSO$_4$, and concentrated. The crude product was purified by BIOTAGE Chromatography (7:3 EtOAc:hexanes) to give 0.45 g (79%) of Compound 49b.

Step B:

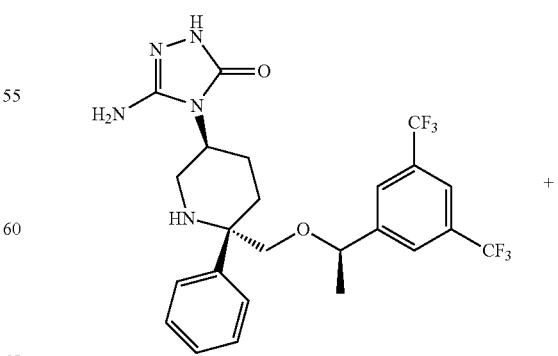

Compound 49b

Compound 49

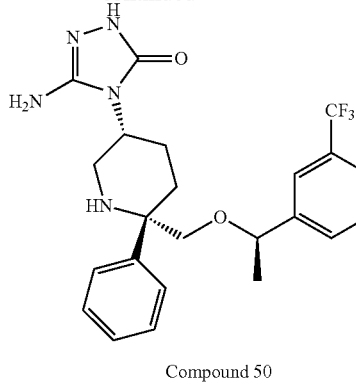

Compound 50

Compounds 49 and 50 were prepared by a procedure similar to the procedure for preparing Compound 44b. HRMS calculated for $C_{24}H_{25}F_6N_5O_2$ (M+H) 530.1991. found 530.1977.

Preparative Example 51

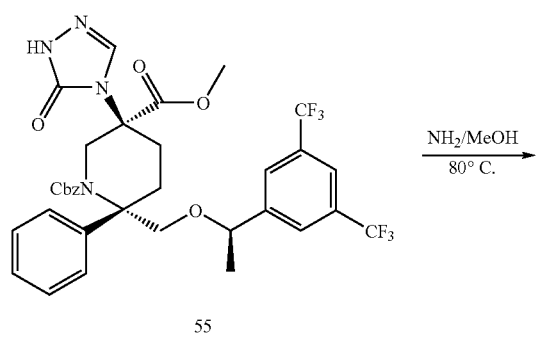

55

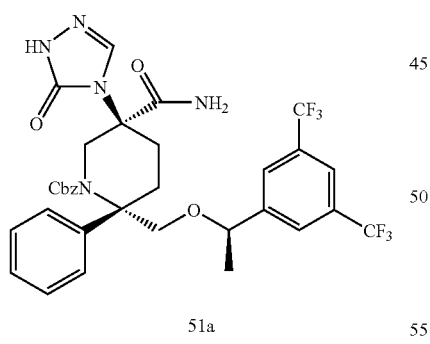

51a

Compound 55 (0.078 g, 0.11 mmol, 1.0 equiv) was dissolved in 7 M ammonia in MeOH (3.0 mL) and was added to a small Parr bomb, which was heated to 80° C. for 2 days. The progress of the reaction was monitored by TLC (9/1 $CH_2Cl_2$/MeOH). Upon completion of the reaction, the reaction mixture was concentrated to give a crude product in the form of a white solid. The crude product was purified using BIOTAGE chromatography (2:1 to 4:1 EtOAc/Hexane) to give Compound 51a as a white solid (0.48 g).

Electrospray MS [M+1] 692.2.

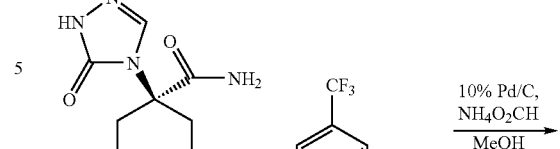

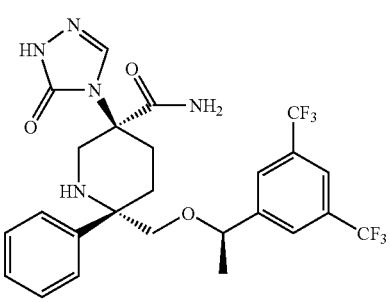

Compound 51

Compound 51a (0.045 g, 0.065 mmol, 1.0 equiv.) was dissolved in dry MeOH (2.0 mL) and was treated with 10% Pd/C (40% wt.) followed by ammonium formate (0.02 g, 0.03 mmol, 5.0 equiv.) under an inert atmosphere. The reaction mixture was heated to reflux and the progress of the reaction was monitored by TLC (100% EtOAc). The reaction was completed in 1 hr. The reaction mixture was filtered through CELITE, washed with EtOAc and concentrated under vacuum. The resulting residue was taken up in EtOAc, washed with saturated $NaHCO_3$, followed by brine and $H_2O$ to give the desired product, Compound 51 in the form of a white solid, which was converted to its HCl salt (0.034 g, 94%).

HRMS (FAB) calculated for $C_{26}H_{28}F_6N_3O_2$ (M+1) 558.19242. found 558.19398.

Preparative Example 52

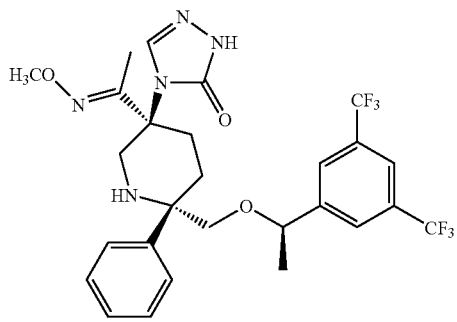

Compound 52

Step A:

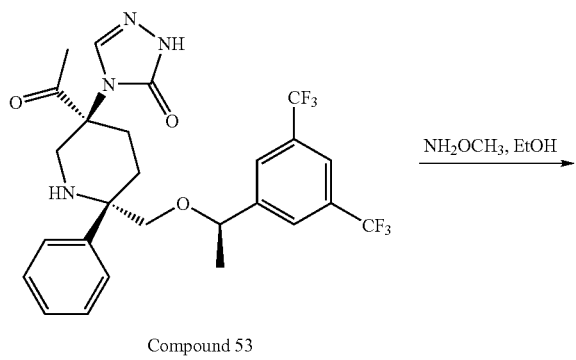

Compound 53

NH₂OCH₃, EtOH
→

Compound 52

Compound 53 (18.1 mg, 0.0325 mmol) in EtOH (2.5 mL) was treated with MeONH₂.HCl (24.4 mg, 0.292 mmol) and NaOAc (12.0 mg, 0.146 mmol) at room temperature. The reaction mixture was stirred at 60° C. for 12 hr, then diluted with EtOAc (20 mL) and washed with aqueous NaHCO₃. The aqueous phase was extracted with EtOAc (3×10 mL). The combined organic layers were washed with water (10 mL), brine (10 mL), and dried over MgSO₄. After filtration and concentration, the cruse product was purified using preparative TLC (hexane/EtOAc, v/v=1/1 to 1/9) to give Compound 52 (16 mg, 84%). Electrospray MS [M+1]⁺ 586.1.

Preparative Example 53

Compound 53

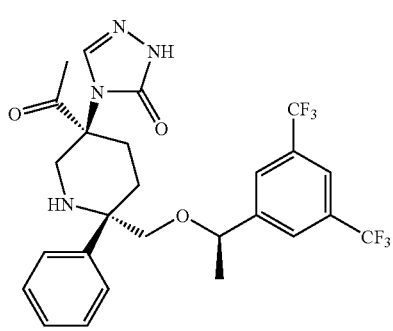

Step A:

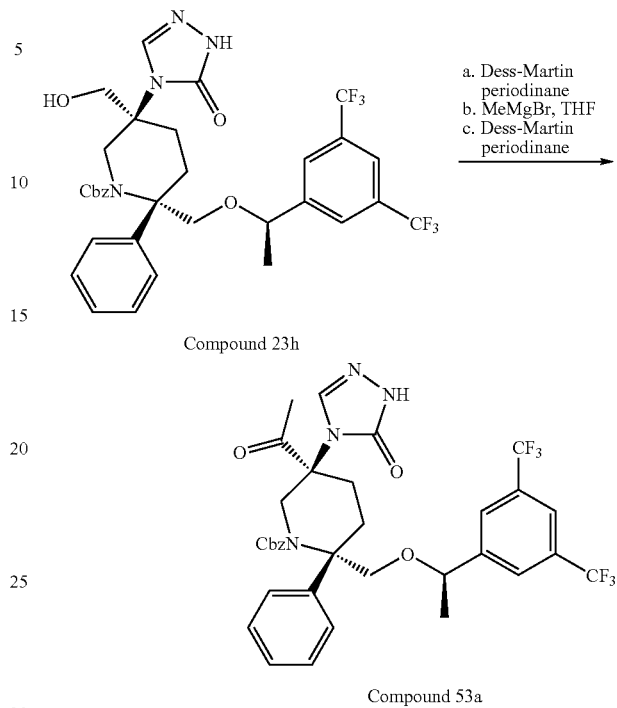

Dess-Martin periodinane (0.234 g, 0.553 mmol) was added to a mixture of Compound 23h (0.25 g, 0.369 mmol) and NaHCO₃ (0.232 g, 2.76 mmol) in CH₂Cl₂ (5.0 mL) at room temperature. The reaction mixture was stirred for 1 hour before it was diluted with EtOAc (50 mL) and water (10 mL). The organic phase was washed with saturated Na₂S₂O₃ solution (3×15 mL). The combined aqueous phases were extracted with EtOAc (3×15 mL). The combined organic layers were washed with NaOH solution (15 mL, 1.0 N), water (10 mL), brine (15 mL), and dried over MgSO₄. After filtration and concentration, the crude aldehyde (0.25 g) was taken up in anhydrous THF (4.0 mL) and was treated with MeMgBr (0.49 mL, 1.48 mmol, 3.0 M in Et₂O) at −78° C. The reaction temperature was slowly increased to room temperature and the reaction was quenched in 2 hours with the slow addition of saturated aqueous NH₄Cl solution (10 mL). The reaction mixture was then diluted with EtOAc (50 mL) and neutralized with 0.5 N HCl until the aqueous phase was slightly acidic. The aqueous phase was extracted with EtOAc (3×15 mL). The combined organic layers were washed with water (10 mL), brine (10 mL), and dried over MgSO₄. After filtration and concentration, the crude secondary alcohol (0.26 g) was taken up in CH₂Cl₂ (5.0 mL) and treated with Dess-Martin periodinane (0.468 g, 1.11 mmol) and NaHCO₃ (0.466 g, 5.55 mmol) at room temperature. The reaction mixture was stirred for 1 hour before it was diluted with EtOAc (50 mL) and water (10 mL). The organic phase was washed with saturated Na₂S₂O₃ solution (3×15 mL). The combined aqueous phases were extracted with EtOAc (3×15 mL). The combined organic layers were washed with NaOH solution (15 mL, 1.0 N), water (10 mL), brine (15 mL), and dried over MgSO₄. After filtration and concentration, the crude produce was purified using BIOTAGE chromatography (hexane/EtOAc, v/v=1/1) to give Compound 53a (0.11 g, 43% for 3 steps).

Step B:

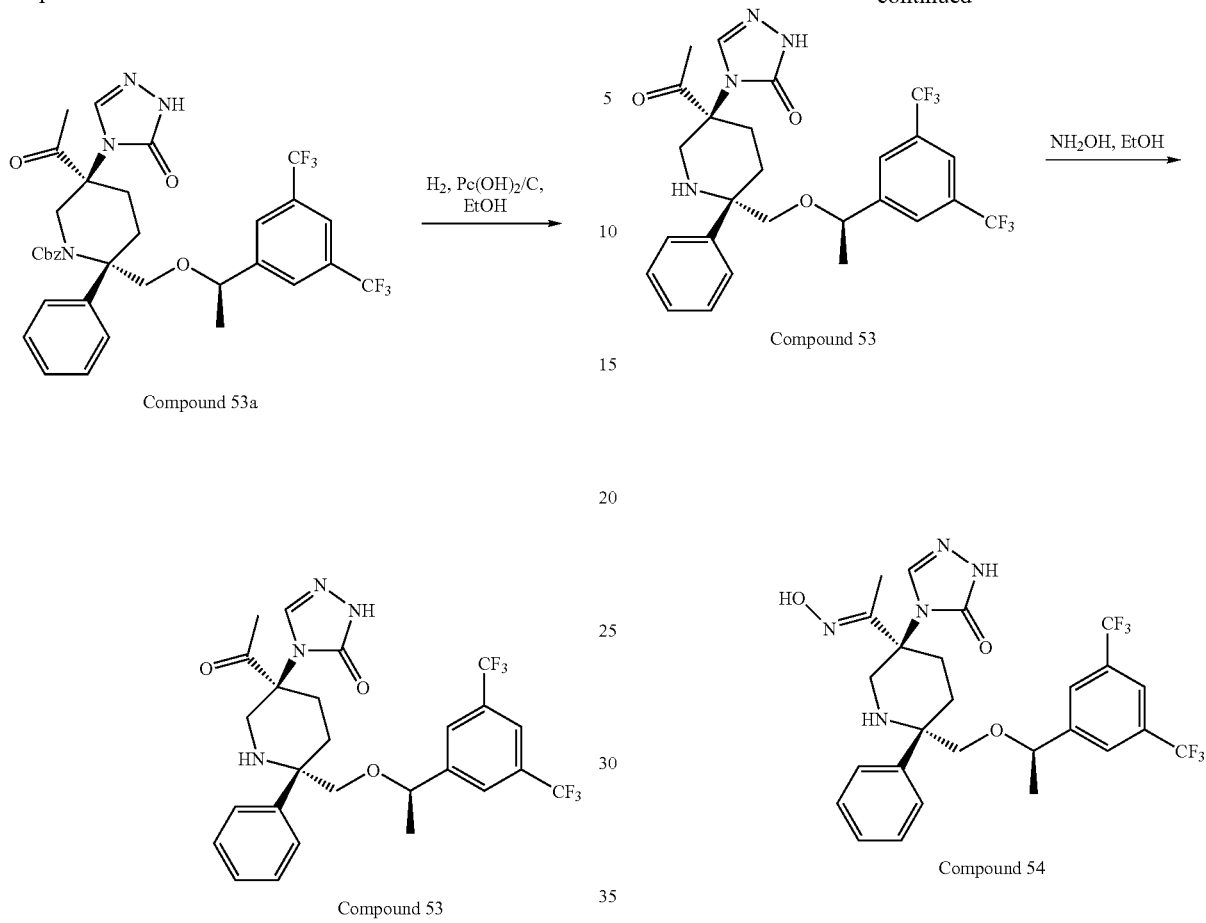

Compound 53a (107 mg, 0.155 mmol) in EtOH (5.0 mL) was treated at room temperature with Pd(OH)₂/C (21.5 mg, 10 wt %) and was hydrogenated with a H₂ balloon for 30 minutes. The reaction solution was filtered through a short pad of CELITE and the residue was washed with EtOH (15 mL). The solvent was removed under reduced pressure and the crude product was purified using BIOTAGE chromatography (hexane/EtOAc, v/v=1/3 to 1/9) to give Compound 53 (66 mg, 76%). Electrospray MS [M+1]⁺ 557.3.

Compound 53 (14.3 mg, 0.0257 mmol) in EtOH (2.5 mL) was treated with HONH₂.HCl (10.7 mg, 0.154 mmol) and NaOAc (6.3 mg, 0.077 mmol) at room temperature. The reaction mixture was stirred at 60° C. for 12 hr, then diluted with EtOAc (20 mL) and washed with aqueous NaHCO₃. The aqueous phase was extracted with EtOAc (3×10 mL). The combined organic layers were washed with water (10 mL), brine (10 mL), and dried over MgSO₄. After filtration and concentration, the crude product was purified using preparative TLC (hexane/EtOAc, v/v=1/2) to give Compound 54 (11 mg, 75%). Electrospray MS [M+1]⁺ 572.1.

Preparative Example 54

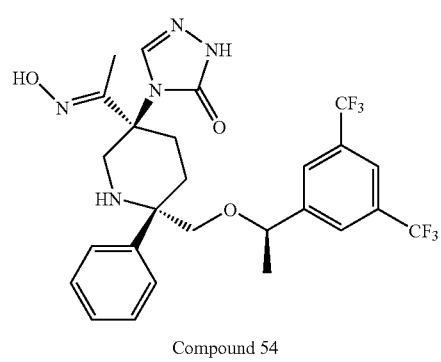

Compound 54

Preparative Example 55

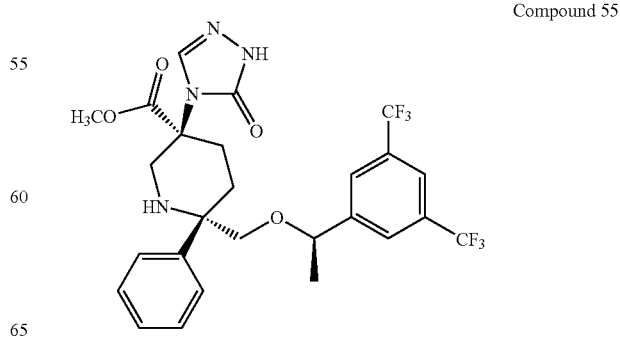

Compound 55

Step A:

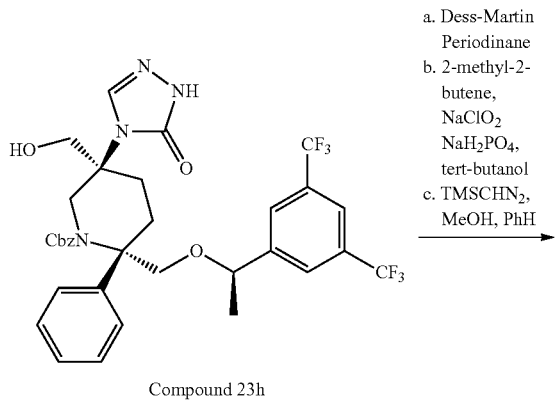

Compound 23h

Step B:

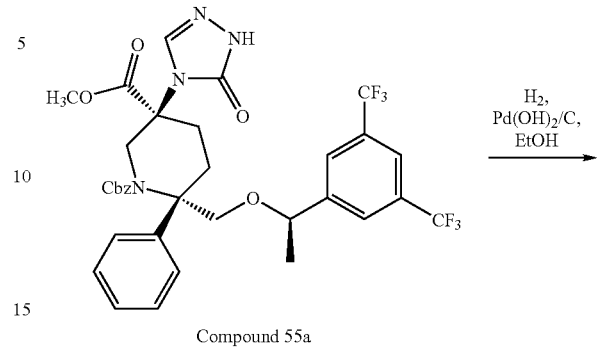

Compound 55a

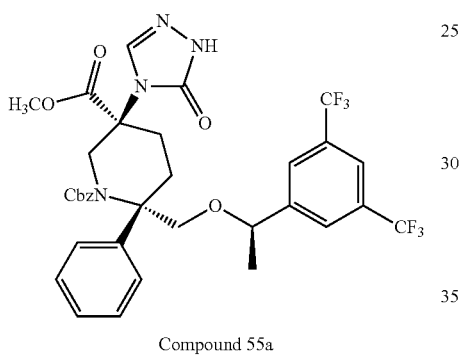

Compound 55a

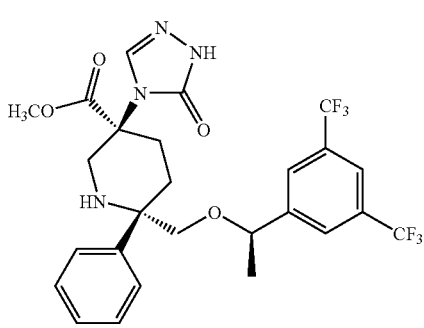

Compound 55

Dess-Martin Periodinane (0.12 g, 0.284 mmol) was added to a mixture of Compound 23h (96.3 mg, 0.142 mmol) and NaHCO$_3$ (0.12 g, 1.42 mmol) in CH$_2$Cl$_2$ (3.0 mL) at room temperature. The reaction mixture was stirred for 1 hour before it was diluted with addition of EtOAc (50 mL) and water (10 mL). The organic phase was washed with saturated Na$_2$S$_2$O$_3$ solution (3×15 mL). The combined aqueous phases were extracted with EtOAc (3×15 mL). The combined organic layers were washed with NaOH solution (15 mL, 1.0 N), water (10 mL), brine (15 mL), and dried over MgSO$_4$. After filtration and concentration, the crude aldehyde (96.3 mg) was taken up in tert-butanol (2.0 mL) and water (0.5 mL) and treated with NaH$_2$PO$_4$.H$_2$O (39.2 mg, 0.284 mmol), NaClO$_2$ (44.9 mg, 0.497 mmol) and 2-methyl-2-butene (0.105 mL, 0.994 mmol) successively. The reaction mixture was stirred for 2 hours and then diluted with EtOAc (20 mL) and washed with aqueous NH$_4$Cl. The aqueous phase was extracted with EtOAc (3×10 mL). The combined organic layers were washed with water (10 mL), brine (10 mL), and dried over MgSO$_4$. After filtration and concentration, the crude acid (95 mg) was dissolved in benzene (2.8 mL) and MeOH (0.7 mL). The resulting solution was treated with TMSCHN$_2$ (82.2 µL, 0.164 mmol) at room temperature and stirred for 20 minutes. The solvent was removed under reduced pressure and the crude product was purified using BIOTAGE chromatography (hexane/EtOAc, v/v=2/3) to give Compound 55a (70 mg, 35% for 3 steps).

Compound 55a (38 mg, 0.0537 mmol) in EtOH (3.0 mL) was treated at room temperature with Pd(OH)$_2$/C (7.6 mg, 10 wt %) and was hydrogenated with a H$_2$ balloon for 30 minutes. The reaction solution was filtered through a short pad of CELITE and the residue was washed with EtOH (15 mL). The solvent was removed under reduced pressure and the crude product was purified using preparative TLC (hexane/EtOAc, v/v=2/3) to give Compound 55 (24 mg, 78%). Electrospray MS [M+1]$^+$ 573.1.

Preparative Example 56

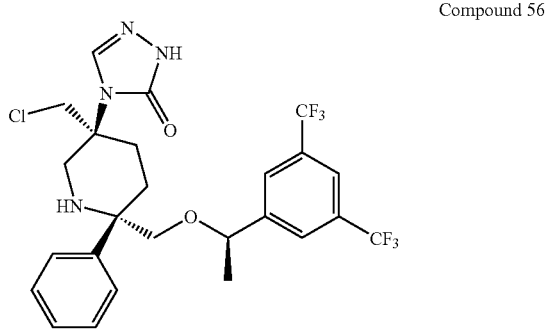

Compound 56

Step A:

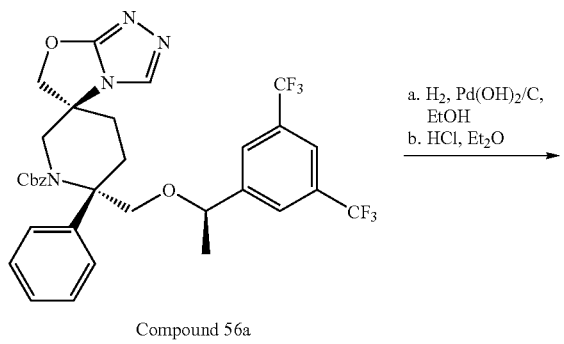

Compound 56a

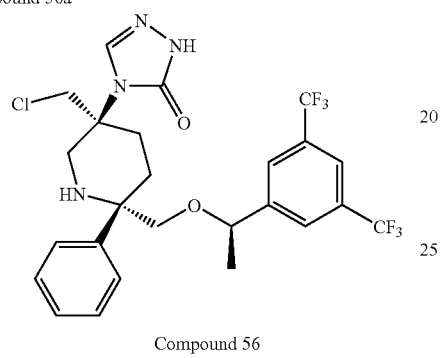

Compound 56

Compound 56a (15 mg, 0.0227 mmol) in EtOH (2.0 mL) was treated at room temperature with Pd(OH)$_2$/C (3.6 mg, 10 wt %) and was hydrogenated with a H$_2$ balloon for 30 minutes. The reaction solution was filtered through a short pad of CELITE and the residue was washed with EtOH (15 mL). The solvent was removed under reduced pressure and the crude product was taken up in Et$_2$O (0.5 mL) and treated with HCl in ether (0.23 mL, 0.23 mmol, 1.0 M in ether). The mixture was stirred at room temperature for 12 hours. The mixture was then diluted with EtOAc (20 mL) and washed with aqueous NaOH (5 mL, 0.5 N). The aqueous phase was extracted with EtOAc (3×10 mL). The combined organic layers were washed with water (10 mL), brine (10 mL), and dried over MgSO$_4$. After filtration and concentration, the crude product was purified using preparative TLC (hexane/EtOAc, v/v=1/1) to give Compound 56 (8.5 mg, 67%). Electrospray MS [M+1]$^+$ 563.1.

Preparative Example 57

Compound 57

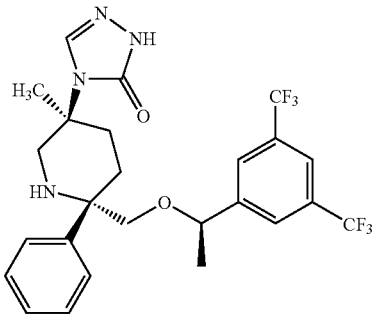

Step A:

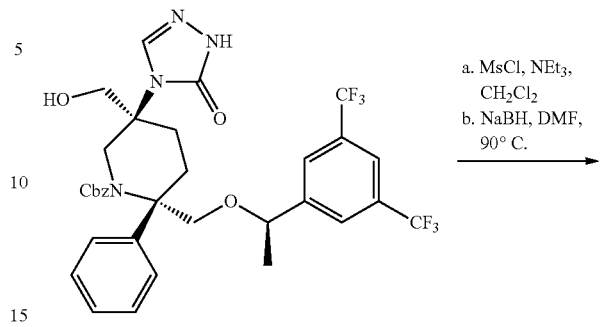

Compound 23h

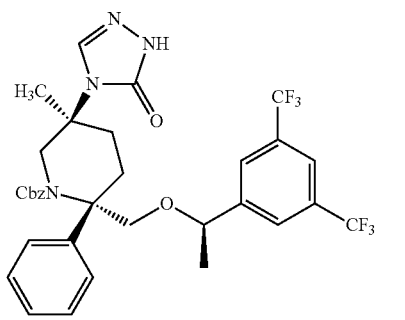

Compound 57a

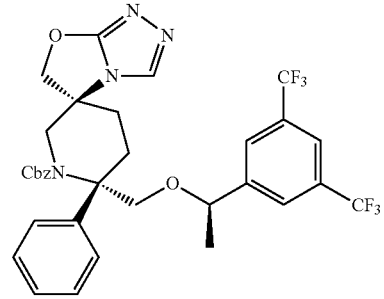

Compound 56a

MsCl (11.7 µL, 0.151 mmol) was added to a solution of Compound 23h (42.8 mg, 0.063 mmol) and Et$_3$N (26.4 µL, 0.189 mmol) in CH$_2$Cl$_2$ (1.0 mL) at room temperature. The reaction mixture was quenched with water (5.0 mL) after 30 minutes and diluted with CH$_2$Cl$_2$ (15 mL). The aqueous phase was extracted with CH$_2$Cl$_2$ (3×10 mL). The combined organic layers were washed with water (10 mL), brine (10 mL), and dried over MgSO$_4$. After filtration and concentration, the crude mesylate (44 mg, 0.0582 mmol) was taken up in anhydrous DMF (2.0 mL) and treated with NaBH$_4$ (11.0 mg, 0.291 mmol). The reaction mixture was heated at 90° C. for 1 hour before it was cooled down to room temperature. The reaction mixture was then diluted with EtOAc (20 mL) and washed with aqueous HCl (5 mL, 1.0 M). The aqueous phase was extracted with EtOAc (3×10 mL). The combined organic layers were washed with water (3×10 ml), brine (10 mL), and dried over MgSO$_4$. After filtration and concentration, the crude product was purified using preparative TLC (hexane/EtOAc, v/v=3/2) to give Compound 57a (18 mg, 43%) and Compound 56a (15 mg, 36%).

Step B:

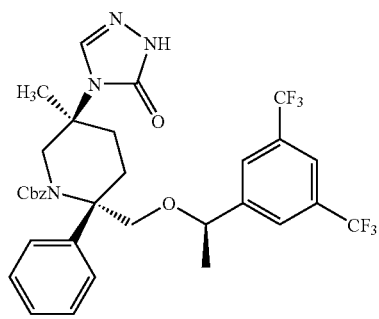

Compound 57a

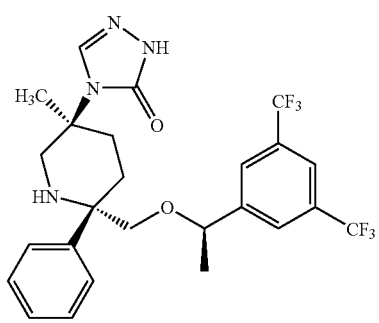

Compound 57

Compound 57a (18 mg, 0.027 mmol) in EtOH (3.0 mL) was treated at room temperature with Pd(OH)$_2$/C (3.6 mg, 10 wt %) and was hydrogenated with a H$_2$ balloon for 30 minutes. The reaction solution was filtered through a short pad of CELITE and the residue was washed with EtOH (15 mL). The solvent was removed under reduced pressure and the crude product was purified using preparative TLC (hexane/EtOAc, v/v=1/1) to give Compound 57 (10 mg, 70%). Electrospray MS [M+1]$^+$ 529.1.

Preparative Example 58

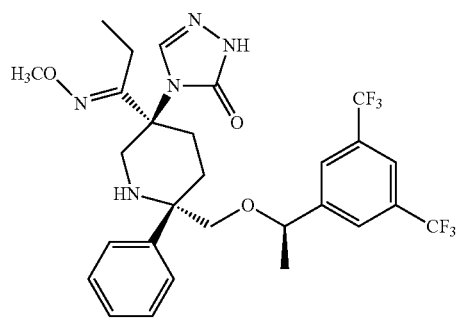

Compound 58

-continued

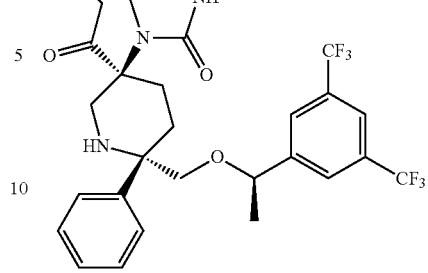

Compound 19

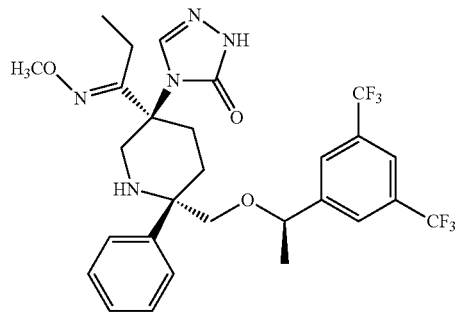

Compound 58

Compound 19 (10.0 mg, 0.0175 mmol) in EtOH (1.5 mL) was treated with MeONH$_2$.HCl (14.6 mg, 0.175 mmol) and NaOAc (7.2 mg, 0.0876 mmol) at room temperature. The reaction mixture was stirred at 60° C. for 12 hr, and was then diluted with EtOAc (20 mL) and washed with aqueous NaHCO$_3$. The aqueous phase was extracted with EtOAc (3×10 mL). The combined organic layers were washed with water (10 mL), brine (10 mL), and dried over MgSO$_4$. After filtration and concentration, the crude product was purified using preparative TLC (hexane/EtOAc, v/v=2/3) to give Compound 58 (10.5 mg, 100%). Electrospray MS [M+1]$^+$ 600.1.

Preparative Example 59

Compound 59

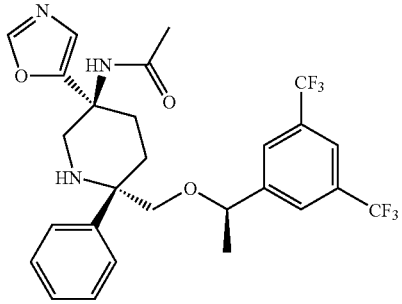

Step A:

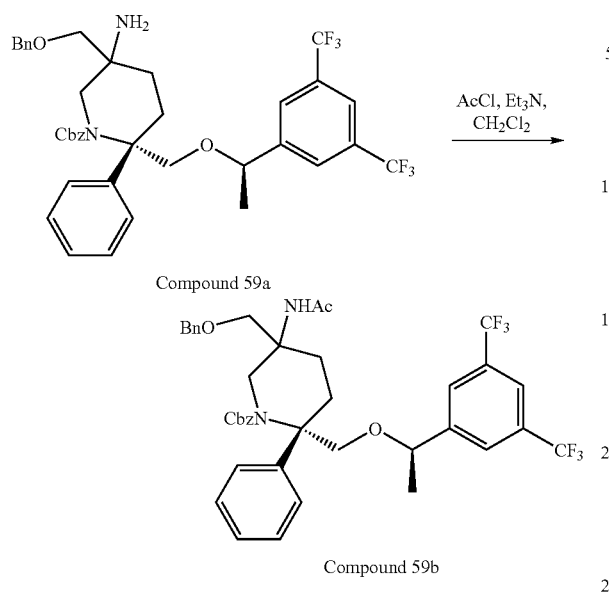

To a solution of Compound 59a (0.53 g, 0.76 mmol) in CH₂Cl₂ (4 mL) was added Et₃N (0.14 mL, 0.98 mmol). The reaction mixture was cooled to −78° C. and acetyl chloride (0.065 mL, 0.91 mmol) was added. The reaction mixture was slowly warmed to room temperature and stirred for 72 hours. Additional Et₃N (0.068 mL) and acetyl chloride (0.033 mL) was added to the reaction mixture, which was then stirred at room temperature for 4 hours. The reaction mixture was concentrated and purified with BIOTAGE chromatography (hexane/EtOAc, v/v=3/2) to give Compound 59b (0.5 g).

Step B:

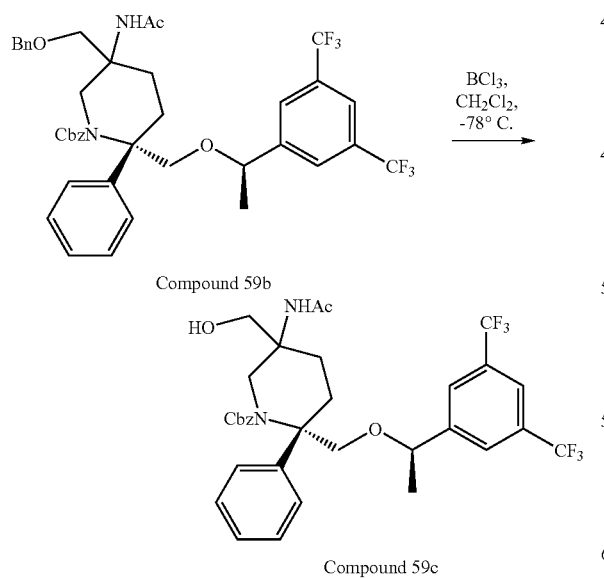

BCl₃ (3.7 mL, 3.7 mmol, 1.0 M in hexane) was added dropwise to a stirring solution of Compound 59b (0.55 g, 0.74 mmol) in CH₂Cl₂ (9 mL) at −78° C. The reaction was quenched in 1 hour by the addition of aqueous NaHCO₃ solution (50 mL) at −78° C. The reaction mixture was diluted with EtOAc (200 mL) and washed with saturated aqueous NaHCO₃ (100 mL), and dried over Na₂SO₄. The mixture was filtered and concentrated to give crude Compound 59c (0.4 g), which was used in the next reaction without further purification.

Step C:

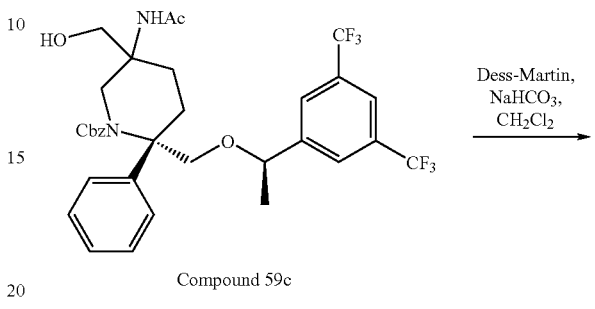

Dess-Martin periodinane (0.12 g, 0.28 mmol) was added to a mixture of Compound 59c (0.12 g, 0.18 mmol) and NaHCO₃ (0.17 g, 2.0 mmol) in CH₂Cl₂ (5.0 mL) at room temperature and stirred for 45 minutes. Additional Dess-Martin periodinane (50 mg) was added to the reaction mixture and stirred at room temperature for 2 hours. The reaction mixture was then concentrated and purified with BIOTAGE chromatography (hexane/EtOAc, v/v =1/1) to give Compound 59d (0.1 g).

Step D:

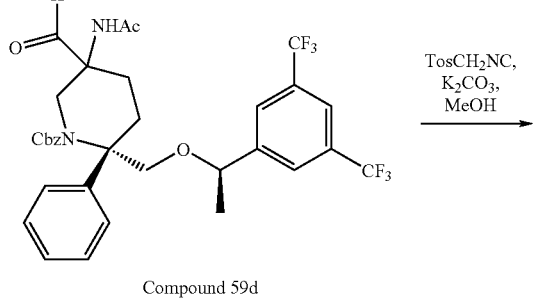

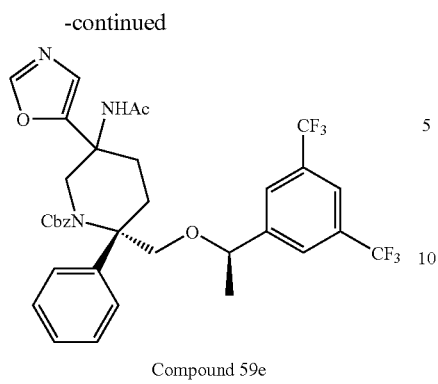

Compound 59e

A mixture of Compound 59d (0.11 g, 0.17 mmol), potassium bicarbonate (26 mg, 0.19 mmol), tosylmethyl isocyanide (36 mg, 0.19 mmol) and methanol (3 mL) was heated at 80° C. for 48 hours. The reaction mixture was then concentrated and diluted with EtOAc (200 mL) and washed with saturated aqueous NaHCO$_3$ (2×100 mL). The organic layer was dried over Na$_2$SO$_4$, filtered and concentrated. The crude product was purified with BIOTAGE chromatography (hexane/EtOAc, v/v=2/3 to 0/100) to give Compound 59e (50 mg).

Step E:

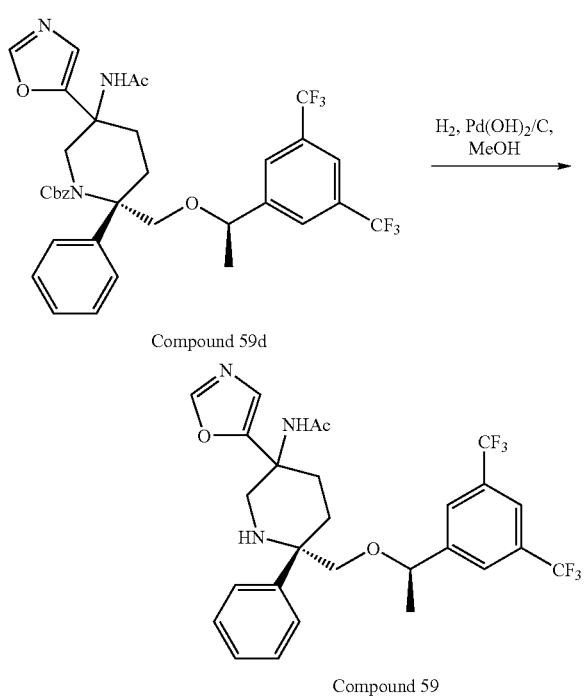

Compound 59d (0.31 mg, 0.45 mmol) in MeOH (10.0 mL) was treated at room temperature with Pd(OH)$_2$/C (0.2 g, 20 wt %) and was hydrogenated with a H$_2$ balloon for 2 hours. The reaction solution was filtered through a short pad of CELITE and the residue was washed with MeOH (30 mL). The solvent was removed under reduced pressure and the crude product was purified with BIOTAGE chromatography (EtOAc/MeOH, v/v=9/1) to give mixture of two isomers (190 mg), which were further purified by HPLC (chiral OD column) with hexane/IPA (v/v=9/1) to give Compound 59 (90 mg).

Preparative Example 60

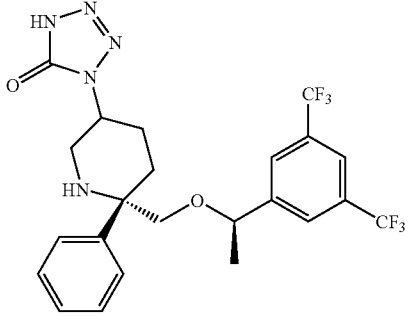

Compound 60

Step A:

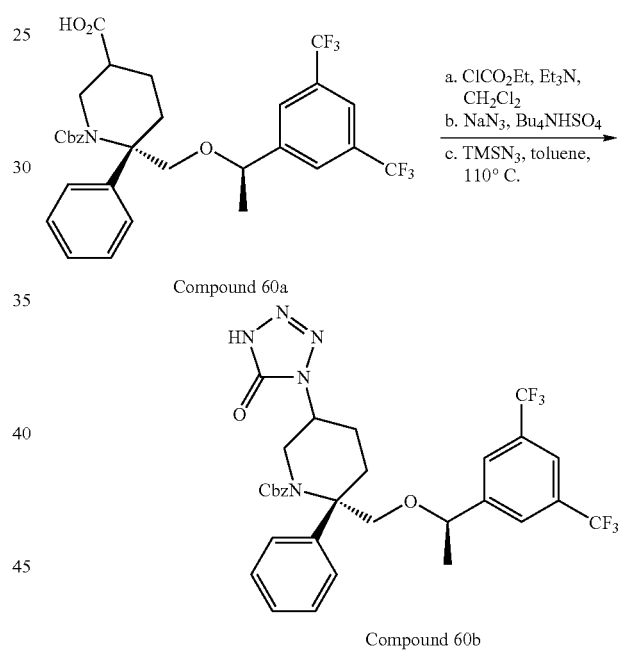

To a solution of Compound 60a (0.26 g, 0.43 mmol) in CH$_2$Cl$_2$ (4 mL) at 0° C. was added Et$_3$N (0.071 mL, 0.51 mmol) followed by ethylchloroformate (0.052 mL, 0.56 mmol), and the reaction mixture was stirred for 1 hour. To the reaction mixture was then added sodium azide (64 mg, 0.98 mmol) and tetrabutylammonium hydrogen sulfate (43 mg, 0.13 mmol) and stirring was continued for 1 hour. The reaction mixture was then diluted with CH$_2$Cl$_2$ (100 ml) and washed with water (1×100 mL) and brine (1×100 mL). The organic layer was dried over Na$_2$SO$_4$, filtered and concentrated. The residue was dissolved in dry toluene (4 ml) and heated to 80° C. for 2 hours and then cooled to room temperature. TMSN$_3$ (0.13 mL, 0.94 mmol) was added and the reaction mixture was heated to −110° C. for 18 hours. The reaction mixture was then cooled to room temperature, concentrated and purified by BIOTAGE chromatography (hexane/EtOAc, v/v=2/1, followed by MeOH/EtOAc, v/v=1/99) to give Compound 60b (0.17 g).

Step B:

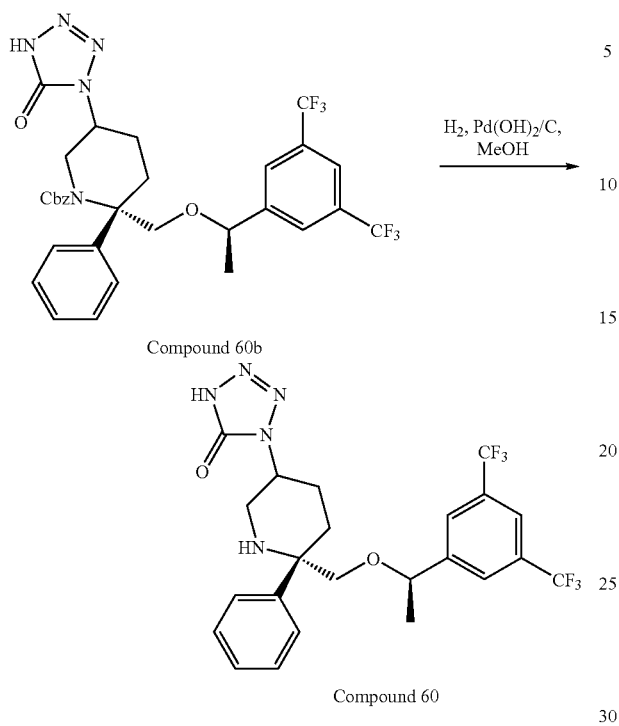

Compound 60b (0.17 mg, 0.26 mmol) in MeOH (10.0 mL) was treated at room temperature with Pd(OH)$_2$/C (15 mg, 20 wt %) and was hydrogenated with a H$_2$ balloon for 2 hours. The reaction solution was filtered through a short pad of CELITE and the residue was washed with MeOH (30 mL). The solvent was removed under reduced pressure and the crude product was purified by BIOTAGE chromatography (EtOAc/MeOH, v/v=98/2) to give Compound 60 (20 mg).

While the present invention has been described in conjunction with the specific embodiments set forth above, many alternatives, modifications and variations thereof will be apparent to those of ordinary skill in the art. All such alternatives, medications and variations are intended to fall within the spirit and scope of the present invention.

What is claimed is:

1. A method of treating a physiological disorder, symptom or disease, selected from cough, emesis, nausea and vomiting, comprising:
   administering to a patient in need thereof an effective amount of at least one compound of formula I:

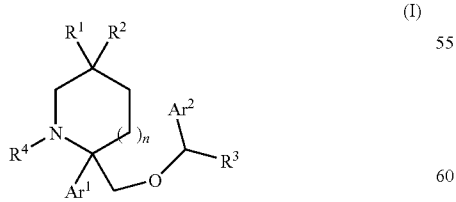

(I)

or a pharmaceutically acceptable salt thereof,
wherein:
R$^1$ and R$^2$ are selected from the group consisting of alkyl, haloalkyl, alkyl substituted with one or more hydroxyl groups, —CN alkynyl, —N(R$^6$)$_2$, —N(R$^6$)—S(O$_2$)-alkyl, —N(R$^6$)—C(O)—N(R$^9$)$_2$, -alkylene-CN, -cycloalkylene-CN, -alkylene-O-alkyl, —C(O)-alkyl, —C(=N—OR$^5$)-alkyl, —C(O)—O-alkyl, -alkylene-C(O)-alkyl, -alkylene-C(O)—O-alkyl, -alkylene-C(O)—N(R$^9$)$_2$,

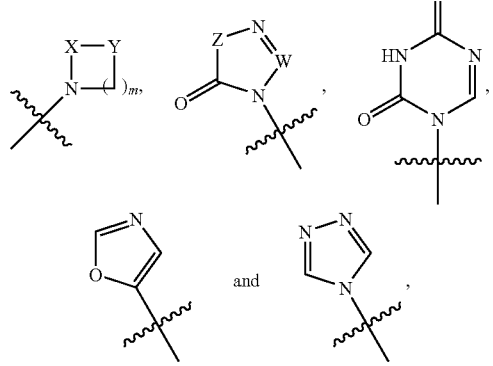

with the proviso that at least one of R$^1$ and R$^2$ is —CN,

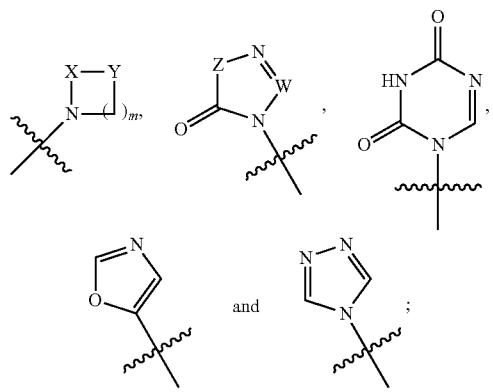

W is =C(R$^8$)— or =N—;
X is —C(O)— or —S(O$_2$)—;
Y is selected from the group consisting of —CH$_2$—, —O—, and —N(R$^6$)—C(O)—, with the proviso that:
  (a) The nitrogen atom of —N(R$^6$)—C(O)— is bonded to X, and
  (b) if R$^1$ and/or R$^2$ is

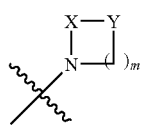

and Y is —O—, X is not —S(O$_2$)—;
Z is —C(R$^7$)$_2$, —N(R$^6$)—, or —O—;
R$^3$ is selected from the group consisting of H, and unsubstituted alkyl;
R$^4$ is H;
R$^5$ is H or alkyl;
R$^6$ is selected from the group consisting of H, alkyl, cycloalkyl, and aryl;
each R$^7$ is independently H or alkyl; or
  each R$^7$, together with the ring carbon to which they are shown attached, form a cycloalkylene ring;

R[8] is selected from the group consisting of H, alkyl, alkyl substituted with one or more hydroxyl groups, —N(R[6])$_2$, —N(R[6])—S(O$_2$)-alkyl, —N(R[6])—S(O$_2$)-aryl, —N(R[6])—C(O)-alkyl, —N(R[6])—C(O)-aryl, alkylene-O-alkyl, and —CN;

R[9] is selected from the group consisting of H, alkyl, and aryl, or each R[9], together with the nitrogen to which they are shown attached, form a heterocycloalkyl ring;

Ar[1] is unsubstituted phenyl;

Ar[2] is phenyl substituted with 0-3 substituents selected from the group consisting of haloalkyl;

n is 0, 1, or 2; and m is 1, 2 or 3.

2. The method of claim 1, wherein the physiological disorder, symptom or disease is emesis.

3. The method of claim 1, wherein the physiological disorder, symptom or disease is vomiting.

4. The method of claim 1, wherein the physiological disorder, symptom or disease is nausea and vomiting.

5. The method of claim 1, wherein the physiological disorder, symptom or disease is cough.

6. The method of claim 1, further comprising administering to the patient an effective amount of at least one antidepressant agent and/or at least one anti-anxiety agent.

7. The method of claim 6, wherein the at least one antidepressant agent and/or at least one anti-anxiety agent is a selective serotonin reuptake inhibitor.

8. A method for antagonizing an effect of a Substance P at a Neurokinin-1 receptor site or for blocking at least one neurokinin-1 receptor, in a patient in need of such treatment, comprising administering to a patient an effective amount of at least one compound of claim 1 or a pharmaceutically acceptable salt thereof.

9. The method according to claim 1, further comprising:
administering an effective amount of at least one active ingredient selected from the group consisting of serotonin 5-HT$_3$ receptor antagonists and glucocorticoids.

10. The method of claim 9, wherein the serotonin 5-HT$_3$ receptor antagonist is ondansetron and the glucocorticoid is dexamethasone.

11. The method according to claim 1 wherein the compound of formula I has the structure:

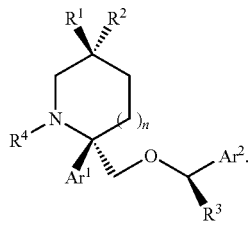

12. The method according to claim 1 wherein, in the compound of formula I,
R[3] is unsubstituted alkyl;
Ar[2] is substituted phenyl; and
n is 1,
or a pharmaceutically acceptable salt thereof.

13. The method according to claim 1 wherein, in the compound of formula I,
R[3] is unsubstituted alkyl;
Ar[2] is substituted phenyl; and
n is 1,
or a pharmaceutically acceptable salt thereof.

14. The method according to claim 1 wherein, in the compound of formula I,
Ar[2] is 3,5-bis(trifluoromethyl)phenyl,
or a pharmaceutically acceptable salt thereof.

15. The method according to claim 1 wherein, in the compound of formula I,
R[3] is —CH$_3$,
or a pharmaceutically acceptable salt thereof.

16. The method according to claim 1 wherein, in the compound of formula I,
one of R[1] or R[2] is

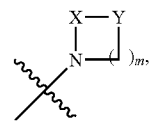

or a pharmaceutically acceptable salt thereof.

17. The method according to claim 1 wherein, in the compound of formula I,
one of R[1] or R[2] is

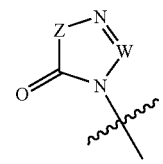

wherein W is =C(R[8])—
or a pharmaceutically acceptable salt thereof.

18. The method according to claim 1 wherein, in the compound of formula I,
one of R[1] and R[2] is

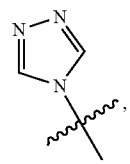

or a pharmaceutically acceptable salt thereof.

19. The method according to claim 1 wherein, in the compound of formula I,
one of R[1] or R[2] is —CN,
or a pharmaceutically acceptable salt thereof.

20. The method according to claim 1 wherein, in the compound of formula I,
X is —S(O$_2$)—;
Y is —CH$_2$—; and
m is 2,
or a pharmaceutically acceptable salt thereof.

21. The method according to claim 1 wherein, in the compound of formula I,
X is —C(O)—;
Y is —CH$_2$—; and
m is 2,
or a pharmaceutically acceptable salt thereof.

22. The method according to claim 1 wherein, in the compound of formula I,
X is —C(O)—;
Y is —CH₂—; and
m is 3,
or a pharmaceutically acceptable salt thereof.

23. The method according to claim 1 wherein, in the compound of formula I,
X is —C(O)—;
Y is —O—; and
m is 2,
or a pharmaceutically acceptable salt thereof.

24. The method according to claim 1 wherein, in the compound of formula I,
X is —C(O)—;
Y is —CH₂—; and
m is 1,
or a pharmaceutically acceptable salt thereof.

25. The method according to claim 1 wherein, in the compound of formula I,
X is —C(O)—;
Y is —NH—C(O)—;
m is 1,
or a pharmaceutically acceptable salt thereof.

26. The method according to claim 1 wherein, in the compound of formula I,
Z is —NH—; and
R⁸ is H,
or a pharmaceutically acceptable salt thereof.

27. The method according to claim 1 wherein, in the compound of formula I,
Z is —NH—; and
R⁸ is —NH—S(O₂)—CH₃,
or a pharmaceutically acceptable salt thereof.

28. The method according to claim 1 wherein, in the compound of formula I,
Z is —NH—;
R⁸ is —CH₂—OH,
or a pharmaceutically acceptable salt thereof.

29. The method according to claim 1 wherein, in the compound of formula I,
Z is —NH—;
R⁸ is —CH₂—O—CH₃,
or a pharmaceutically acceptable salt thereof.

30. The method according to claim 1 wherein, in the compound of formula I,
Z is —NH—;
R⁸ is —NH₂,
or a pharmaceutically acceptable salt thereof.

31. The method according to claim 1 wherein, in the compound of formula I,
Z is

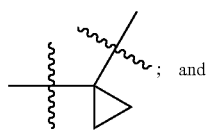

; and

R⁸ is H,
or a pharmaceutically acceptable salt thereof.

32. The method according to claim 1 wherein, in the compound of formula I,
Z is —C(CH₃)₂—; and
R⁸ is H,
or a pharmaceutically acceptable salt thereof.

33. The method according to claim 1, having the formula IB

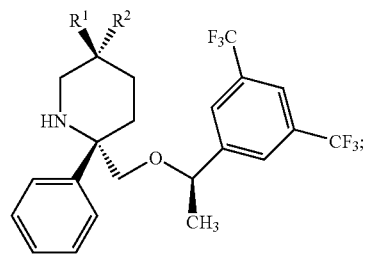

IB wherein R¹ and R² are selected from the group consisting of:

| Compound | R¹ | R² |
|---|---|---|
| 1 | ![piperidinone] | —CN |
| 2 | ![oxazolidinone] | —CN |
| 5 | ![triazole] | —CH₂CN |
| 6 | —CH₃ | ![triazole] |
| 7 | —CN | ![triazole] |
| 8 | —C(O)—O—CH₃ | ![triazole] |
| 9 | ![azetidinone] | —CN |

-continued

| Compound | R¹ | R² |
|---|---|---|
| 12 | —CH₂OH | [1,2,4-triazol-4-yl] |
| 13 | [1,2,4-triazol-1-yl] | —CH₂OCH₃ |
| 14 | —CH₂OCH₃ | [1,2,4-triazol-1-yl] |
| 32 | [isothiazolidine-1,1-dioxide-2-yl] | —CN |
| 33 | [2-oxopyrrolidin-1-yl] | —CN |
| 34 | —CN | [2-oxopyrrolidin-1-yl] |
| 35 | —CN | [3-oxo-2,3-dihydro-1H-1,2,4-triazol-4-yl] |
| 36 | —NH—S(O₂)—CH₃ | —CN |
| 37 | —CN | —NH—S(O₂)—CH₃ |
| 38 | [3-oxo-2,3-dihydro-1H-1,2,4-triazol-1-yl] | —CH₂CN |
| 39 | —CN | —NH₂ |
| 40 | —NH₂ | —CN |
| 41 | —NH—C(O)—NH₂ | —CN |
| 42 | [3-oxo-2,3-dihydro-1H-1,2,4-triazol-1-yl] | —CN | or a pharmaceutically acceptable salt thereof.

34. The method according to claim 1 wherein the compound of formula I is

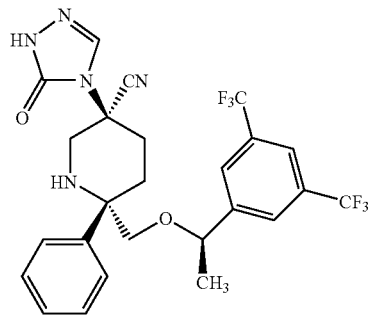

or a pharmaceutically acceptable salt thereof.

35. The method according to claim 1 wherein the compound of formula I is

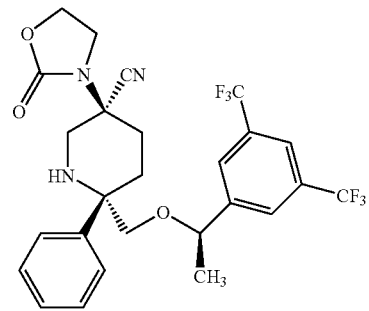

or a pharmaceutically acceptable salt thereof.

36. The method according to claim 1 wherein the compound of formula I is

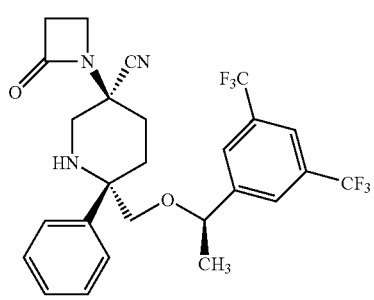

or a pharmaceutically acceptable salt thereof.

37. The method according to claim 2 wherein the emesis is chemotherapy induced emesis.

38. The method according to claim 2 wherein the emesis is radiation induced emesis.

39. The method according to claim 4 wherein the nausea and vomiting is post operative nausea and vomiting.

* * * * *

UNITED STATES PATENT AND TRADEMARK OFFICE
CERTIFICATE OF CORRECTION

Page 1 of 1

PATENT NO. : 8,026,364 B2
APPLICATION NO. : 12/750420
DATED : September 27, 2011
INVENTOR(S) : Sapna S. Shah et al.

It is certified that error appears in the above-identified patent and that said Letters Patent is hereby corrected as shown below:

In Column 157, Line 67, please delete "-CN alkynyl" and insert --CN, alkynyl--

In Column 158, Lines 35-40, please delete:

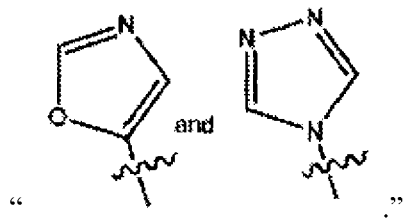

"           and           "

and replace with:

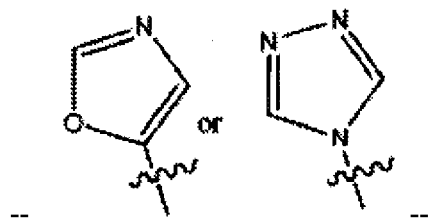

--           or           --

In Column 158, Line 46, please delete "(a) The nitrogen" and insert --(a) the nitrogen--

Signed and Sealed this
Fifteenth Day of November, 2011

David J. Kappos
*Director of the United States Patent and Trademark Office*